United States Patent
Hetz Flores et al.

(10) Patent No.: US 11,400,166 B2
(45) Date of Patent: Aug. 2, 2022

(54) AAV/XBP1S-HA VIRUS, GENE THERAPY METHOD AND USE THEREOF IN THE OPTIMISATION AND IMPROVEMENT OF LEARNING, MEMORY AND COGNITIVE CAPACITIES

(71) Applicant: UNIVERSIDAD DE CHILE, Santiago (CL)

(72) Inventors: Claudio Andres Hetz Flores, Santiago (CL); Gabriela Raquel Elena Martinez Bravo, Santiago (CL)

(73) Assignee: Universidad de Chile, Santiago (CL)

( * ) Notice: Subject to any disclaimer, the term of this patent is extended or adjusted under 35 U.S.C. 154(b) by 306 days.

(21) Appl. No.: 15/539,826

(22) PCT Filed: Dec. 24, 2015

(86) PCT No.: PCT/CL2015/000069
§ 371 (c)(1),
(2) Date: Aug. 15, 2017

(87) PCT Pub. No.: WO2016/106458
PCT Pub. Date: Jul. 7, 2016

(65) Prior Publication Data
US 2017/0360961 A1  Dec. 21, 2017

(30) Foreign Application Priority Data
Dec. 30, 2014  (CL) .................................... 3590-2014

(51) Int. Cl.
*A61K 48/00* (2006.01)
*C07K 14/47* (2006.01)
*C12N 15/86* (2006.01)

(52) U.S. Cl.
CPC ...... *A61K 48/0058* (2013.01); *A61K 48/0075* (2013.01); *C07K 14/4702* (2013.01); *C12N 15/86* (2013.01); *A61K 48/00* (2013.01); *C12N 2750/14143* (2013.01); *C12N 2750/14151* (2013.01); *C12N 2830/008* (2013.01)

(58) Field of Classification Search
CPC ................................................ A61K 48/0058
See application file for complete search history.

(56) References Cited

U.S. PATENT DOCUMENTS
7,090,836 B2  8/2006  Desmaris et al.

FOREIGN PATENT DOCUMENTS
WO  WO-2009/034127  3/2009
WO  WO-2009034127 A1 *  3/2009  ............. C12N 15/86

OTHER PUBLICATIONS

He et al. (2010, Gene Expression, vol. 15, pp. 13-25). (Year: 2010).*
Valenzuela et al. (2012, Cell Death and Disease, vol. 3, pp. 1-9) (Year: 2012).*
Delzoretal (2012, Human Gene Therapy Methods, vol. 23, pp. 242-254) (Year: 2012).*
Halbert et al. (2001, J. Virology, vol. 75(14), pp. 6615-6624). (Year: 2001).*
Guggenhuber et al. (2010, PLOS One, vol. 5(12), pp. 1-8). (Year: 2010).*
Yu et al. (2013, PLOS One, vol. 8(4), pp. 1-14). (Year: 2013).*
Duran-Aniotz et al., Memory loss in Alzheimer's disease: are the alterations in the UPR network involved in the cognitive impairment, Frontiers in Aging Neuroscience, Jan. 2014, vol. 6, Article 8.
Martinez, et al., Regulation of memory formation by the transcription factor XBP1, Neurodegener Dis 2015; 15(suppl 1): 352-1969, p. 1739.
Valdes, et al., Control of dopaminergic neuron survival by the unfolded protein response transcription factor XBP1,6804-6809, PNAS, May 6, 2014, vol. 111, No. 18, www.pnas.org.
Valenzuela et al., Activation of the unfolded protein response enhances motor recovery after spinal cord injury, Cell Death and Disease (2012).
Zuleta et al., AAV-mediated delivery of the transcription factor XBP1s into the striatum reduces mutant Huntingtin aggregation in a mouse model of Huntington's disease, Biochemical and Biophysical Research Communications 420 (2012) 558-563, journal homepage: www.elsevier.com/locate/ybbrc.
Bourdenx, Mathieu et al., "Systemic gene delivery to the central nervous system using Adeno-associated virus," Frontiers in Molecular Neuroscience vol. 7, Article 50, pp. 1-8 (2014).
Daily, Jennifer L. et al., "Adeno-Associated Virus-Mediated Rescue of the Cognitive Defects in a Mouse Model for Angelman Syndrome," PLoS One 6(12):e27221, pp. 1-7 (2011).
Ryan, Deborah A. et al., "Aβ-directed Single-chain Antibody Delivery Via a Serotype-1 AAV Vector improves Learning Behavior and Pathology in Alzheimer's Disease Mice," Molecular Therapy 18(8):1471-1481 (2010).
Yang, Bin et al., "Global CNS Transduction of Adult Mice by Intravenously Delivered rAAVrh.8 and rAAVrh.10 and Nonhuman Primates by rAAVrh.10," Molecular Therapy 22(7)1299-1309 (2014).

(Continued)

*Primary Examiner* — Thaian N. Ton
*Assistant Examiner* — David A Montanari
(74) *Attorney, Agent, or Firm* — Medler Ferro Woodhouse & Mills

(57) ABSTRACT

This invention presents a sequence of the virus AAV/XBP1s-HA, method and its use in the improvement of cognitive functions, of memory and of learning, as presented in the in vivo studies in FIG. 12/17 right panel.

14 Claims, 17 Drawing Sheets

Specification includes a Sequence Listing.

(56) References Cited

OTHER PUBLICATIONS

Acosta-Alvear, Diego et al., "XBP1 controls diverse cell type- and condition-specific transcriptional regulatory networks," Molecular Cell 27(1):53-66 (2007).
Cirulli, Francesca et al., "Intrahippocampal administration of BDNF in adult rats affects short-term behavioral plasticity in the Morris water maze and performance in the elevated plus-maze," Hippocampus 14(7):802-807 (2004).
Constantini, L C et al., "Gene therapy in the CNS," Gene Therapy 7(2):93-109 (2000).
Costa-Mattioli, Mauro et al., "Translational Control of Long-Lasting Synaptic Plasticity and Memory," Neuron 61 (1): 1-34 (2009).
Cao, Guangping et al., "Clades of Adeno-associated viruses are widely disseminated in human tissues," Journal of Virology 78(12):6381-6388 (2004).
Graff, Candace et al., "Nasal Drug Administration: Potential for Targeted Central Nervous System Delivery," Journal of Pharmaceutical Sciences 94(6):1187-1195 (2005).
Hall, Jeremy et al., "Rapid and selective induction of BDNF expression in the hippocampus during contextual earning," Nature Neuroscience 3(6):533-535 (2000).
Hetz, Claudio et al., "Unfolded protein response transcription factor XBP-1 does not influence prion replication or pathogenesis," Proceedings of the National Academy of Sciences of the United States of America 105(2):757-762 (2008).
Lee, Ann-Hwee et al., "XBP-1 regulates a subset of endoplasmic reticulum resident chaperone genes in the unfolded protein response," Molecular and Cellular Biology 23(21):7448-7459 (2003).
Mizuno, Makoto et al., "Involvement of Brain-Derived Neurotrophic Factor in Spatial Memory Formation and Maintenance in a Radial Arm Maze Test in Rats," The Journal of Neuroscience 20(18):7116-7121 (2000).
Mu, Jun-Shan et al., "Deprivation of endogenous brain-derived neurotrophic factor results in impairment of spatial earning and memory in adult rats," Brain Research 835(2):259-265 (1999).
Park, Hyungju et al., "Neurotrophin regulation of neural circuit development and function," Nature Reviews Neuroscience 14(1):7-23(2013).
Patterson, Susan L. et al., "Recombinant BDNF rescues deficits in basal synaptic transmission and hippocampal LTP in BDNF knock-out mice," Neuron 16(6):1137-1145 (1996).
Rattiner, Lisa M. et al., "Differential regulation of brain-derived neurotrophic factor transcripts during the consolidation of fear learning," Learning & Memory 11(6):727-731 (2004).
Shintani, Asae et al., "Characterization of the 5'—flanking region of the human brain-derived neurotrophic factor gene," Biochemical and Biophysical Research Communications 182(1):325-332 (1992).
Tao, Xu et al., "Ca2+ influx regulates BDNF transcription by a CREB family transcription factor dependent mechanism," Neuron 20(4):709-726 (1998).
Tao, Xu et al., "A calcium responsive transcription factor, CaRF, that regulates neuronal activity-dependent expression of BDNF," Neuron 33(3):383-395 (2002).
Ulusoy, Ayse et al., "Dose Optimization for Long-term rAAV-mediated RNA Interference in the Nigrostriatal Projection Neurons," Molecular Therapy 17(9): 1574-1584 (2009).
Product Data Sheet, "pAAV-MCS Expression vector," Catalog No. VPK-410, Cell Biolabs, Inc. (Copyright 2010-2021).

* cited by examiner

SEQUENCE LISTING

<160> NUMBER OF SEQ ID NOS: 103

<210> SEQ ID NO 1
<211> LENGTH: 20
<212> TYPE: DNA
<213> ORGANISM: Mus musculus
<220> FEATURE:
<223> OTHER INFORMATION: XBP1 primer s

<400> SEQUENCE: 1
acacgcttgg gaatggacac                                            20

<210> SEQ ID NO 2
<211> LENGTH: 20
<212> TYPE: DNA
<213> ORGANISM: Mus musculus
<220> FEATURE:
<223> OTHER INFORMATION: XBP1 primer as

<400> SEQUENCE: 2
cccagaacat cttcccatgg                                              20

<210> SEQ ID NO 3
<211> LENGTH: 37
<212> TYPE: DNA
<213> ORGANISM: Mus musculus
<220> FEATURE:
<223> OTHER INFORMATION: XBP1s-HA-Chimeric primer S

<400> SEQUENCE: 3
agctatcgat gagatgatgg tggtggtggc agcggcg                            37

<210> SEQ ID NO 4
<211> LENGTH: 63
<212> TYPE: DNA
<213> ORGANISM: Mus musculus
<220> FEATURE:
<223> OTHER INFORMATION: XBP1s-HA-primer AS

<400> SEQUENCE: 4 ttttcccccca gctgattagt gtcttcccat acgatgttcc agattacgtc taaagatcta  60
cgt                                                                63

<210> SEQ ID NO 5
<211> LENGTH: 19
<212> TYPE: DNA
<213> ORGANISM: Rattus norvegicus
<220> FEATURE:
<223> OTHER INFORMATION: Ttr primer S

<400> SEQUENCE: 5
ttgcctcgct ggactggta                                               19

<210> SEQ ID NO 6
<211> LENGTH: 21
<212> TYPE: DNA
<213> ORGANISM: Rattus norvegicus
<220> FEATURE:
<223> OTHER INFORMATION: Ttr primer AS

<400> SEQUENCE: 6
ctgctgtaga cgtggctgta a                                            21

<210> SEQ ID NO 7
<211> LENGTH: 21
<212> TYPE: DNA
<213> ORGANISM: Rattus norvegicus
<220> FEATURE:
<223> OTHER INFORMATION: Reln primer S

<400> SEQUENCE: 7
ctgtgtcata cgccaagaac a                                            21

<210> SEQ ID NO 8
<211> LENGTH: 21
<212> TYPE: DNA

```
<213> ORGANISM: Rattus norvegicus
<220> FEATURE:
<223> OTHER INFORMATION: Reln primer AS

<400> SEQUENCE: 8
atccacatcc tgtacctccc c                                              21

<210> SEQ ID NO 9
<211> LENGTH: 20
<212> TYPE: DNA
<213> ORGANISM: Rattus norvegicus
<220> FEATURE:
<223> OTHER INFORMATION: Gria1 primer S

<400> SEQUENCE: 9
gtccgccctg agaaatccag                                                20

<210> SEQ ID NO 10
<211> LENGTH: 19
<212> TYPE: DNA
<213> ORGANISM: Rattus norvegicus
<220> FEATURE:
<223> OTHER INFORMATION: Gria1 Primer AS

<400> SEQUENCE: 10
gtggtacgac aagggcgag                                                 19

<210> SEQ ID NO 11
<211> LENGTH: 19
<212> TYPE: DNA
<213> ORGANISM: Rattus norvegicus
<220> FEATURE:
<223> OTHER INFORMATION: Gria2 primer S

<400> SEQUENCE: 11
gccgaggcga acgaatga                                                  19

<210> SEQ ID NO 12
<211> LENGTH: 23
<212> TYPE: DNA
<213> ORGANISM: Rattus norvegicus
<220> FEATURE:
<223> OTHER INFORMATION: Gria2 primer AS

<400> SEQUENCE: 12
caacgtatat ggcatcgaca gtg                                            23

<210> SEQ ID NO 13
<211> LENGTH: 21
<212> TYPE: DNA
<213> ORGANISM: Rattus norvegicus
<220> FEATURE:
<223> OTHER INFORMATION: Gria3 primer S

<400> SEQUENCE: 13
accatcagca taggtggact t                                              21

<210> SEQ ID NO 14
<211> LENGTH: 22
<212> TYPE: DNA
<213> ORGANISM: Rattus norvegicus
<220> FEATURE:
<223> OTHER INFORMATION: Gria3 primer AS

<400> SEQUENCE: 14
ccttccattt gaactaccac gt                                             22
```

<210> SEQ ID NO 15
<211> LENGTH: 21
<212> TYPE: DNA
<213> ORGANISM: Rattus norvegicus
<220> FEATURE:
<223> OTHER INFORMATION: Gria4 primer S

<400> SEQUENCE: 15
accatcagca taggtggact t                                        21

<210> SEQ ID NO 16
<211> LENGTH: 21
<212> TYPE: DNA
<213> ORGANISM: Rattus norvegicus
<220> FEATURE:
<223> OTHER INFORMATION: Gria4 primer AS

<400> SEQUENCE: 16
agccaggtta tccatcactg g                                        21

<210> SEQ ID NO 17
<211> LENGTH: 20
<212> TYPE: DNA
<213> ORGANISM: Rattus norvegicus
<220> FEATURE:
<223> OTHER INFORMATION: Myo5b primer S

<400> SEQUENCE: 17
cagcaagtgg tcaatgcacg                                          20

<210> SEQ ID NO 18
<211> LENGTH: 23
<212> TYPE: DNA
<213> ORGANISM: Rattus norvegicus
<220> FEATURE:
<223> OTHER INFORMATION: Myo5b primer AS

<400> SEQUENCE: 18
acagttttgt atcaactacg cca                                      23

<210> SEQ ID NO 19
<211> LENGTH: 21
<212> TYPE: DNA
<213> ORGANISM: Rattus norvegicus
<220> FEATURE:
<223> OTHER INFORMATION: Creb primer S

<400> SEQUENCE: 19
agccgggtac taccattcta c                                        21

<210> SEQ ID NO 20
<211> LENGTH: 21
<212> TYPE: DNA
<213> ORGANISM: Rattus norvegicus
<220> FEATURE:
<223> OTHER INFORMATION: Creb primer AS

<400> SEQUENCE: 20
ccaagttgtt gttcaagctg c                                        21

<210> SEQ ID NO 21
<211> LENGTH: 21
<212> TYPE: DNA
<213> ORGANISM: Rattus norvegicus
<220> FEATURE:

<223> OTHER INFORMATION: Bdnf primer S

<400> SEQUENCE: 21
caggttcgag aggtctgacg a                                              21

<210> SEQ ID NO 22
<211> LENGTH: 22
<212> TYPE: DNA
<213> ORGANISM: Rattus norvegicus
<220> FEATURE:
<223> OTHER INFORMATION: Bdnf primer AS

<400> SEQUENCE: 22
cgaacaaaac cataaggacg cg                                             22

<210> SEQ ID NO 23
<211> LENGTH: 19
<212> TYPE: DNA
<213> ORGANISM: Rattus norvegicus
<220> FEATURE:
<223> OTHER INFORMATION: CamkII primer S

<400> SEQUENCE: 23
tgcctggtgt tgctaaccc                                                 19

<210> SEQ ID NO 24
<211> LENGTH: 22
<212> TYPE: DNA
<213> ORGANISM: Rattus norvegicus
<220> FEATURE:
<223> OTHER INFORMATION: CamkII primer AS

<400> SEQUENCE: 24
agttccagcg ttcagttaat gg                                             22

<210> SEQ ID NO 25
<211> LENGTH: 21
<212> TYPE: DNA
<213> ORGANISM: Rattus norvegicus
<220> FEATURE:
<223> OTHER INFORMATION: Ryr1

<400> SEQUENCE: 25 cagttttgc ggacggatga t                                               21

<210> SEQ ID NO 26
<211> LENGTH: 20
<212> TYPE: DNA
<213> ORGANISM: Rattus norvegicus
<220> FEATURE:
<223> OTHER INFORMATION: Ryr1 primer AS

<400> SEQUENCE: 26
caatactgtg gaggccggtg                                                20

<210> SEQ ID NO 27
<211> LENGTH: 19
<212> TYPE: DNA
<213> ORGANISM: Rattus norvegicus
<220> FEATURE:
<223> OTHER INFORMATION: Ryr2 primer S

<400> SEQUENCE: 27
atggctttaa ggcacagcg                                                 19

```
<210> SEQ ID NO 28
<211> LENGTH: 20
<212> TYPE: DNA
<213> ORGANISM: Rattus norvegicus
<220> FEATURE:
<223> OTHER INFORMATION: Ryr2 primer AS

<400> SEQUENCE: 28
gctggatgat tcgggctctg                                               20

<210> SEQ ID NO 29
<211> LENGTH: 19
<212> TYPE: DNA
<213> ORGANISM: Rattus norvegicus
<220> FEATURE:
<223> OTHER INFORMATION: Ryr3 primer S

<400> SEQUENCE: 29
accaccagga gcaagtacg                                                19

<210> SEQ ID NO 30
<211> LENGTH: 21
<212> TYPE: DNA
<213> ORGANISM: Rattus norvegicus
<220> FEATURE:
<223> OTHER INFORMATION: Ryr3 primer AS

<400> SEQUENCE: 30
tgactacttt gacacgaccc c                                             21

<210> SEQ ID NO 31
<211> LENGTH: 20
<212> TYPE: DNA
<213> ORGANISM: Rattus norvegicus
<220> FEATURE:
<223> OTHER INFORMATION: Nr2a primer S

<400> SEQUENCE: 31
acgtgacaga acgcgaactt                                               20

<210> SEQ ID NO 32
<211> LENGTH: 22
<212> TYPE: DNA
<213> ORGANISM: Rattus norvegicus
<220> FEATURE:
<223> OTHER INFORMATION: Nr2a primer AS

<400> SEQUENCE: 32
cgttattgat gaaccgcact ga                                            22

<210> SEQ ID NO 33
<211> LENGTH: 20
<212> TYPE: DNA
<213> ORGANISM: Rattus norvegicus
<220> FEATURE:
<223> OTHER INFORMATION: Nr2b primer S

<400> SEQUENCE: 33
gccatgaacg agactgaccc                                               20

<210> SEQ ID NO 34
<211> LENGTH: 20
<212> TYPE: DNA
<213> ORGANISM: Rattus norvegicus
<220> FEATURE:
<223> OTHER INFORMATION: Nr2b primer AS
```

<400> SEQUENCE: 34
gatgacacgg accaggaagc                                                20

<210> SEQ ID NO 35
<211> LENGTH: 21
<212> TYPE: DNA
<213> ORGANISM: Rattus norvegicus
<220> FEATURE:
<223> OTHER INFORMATION: Pp2b/Caln primer S

<400> SEQUENCE: 35
aaatgaggcc agctaccaaa c                                              21

<210> SEQ ID NO 36
<211> LENGTH: 20
<212> TYPE: DNA
<213> ORGANISM: Rattus norvegicus
<220> FEATURE:
<223> OTHER INFORMATION: Pp2b/Caln primer AS

<400> SEQUENCE: 36
ctggacttgg acaaatcggg                                                20

<210> SEQ ID NO 37
<211> LENGTH: 19
<212> TYPE: DNA
<213> ORGANISM: Rattus norvegicus
<220> FEATURE:
<223> OTHER INFORMATION: Kif17 primer S

<400> SEQUENCE: 37
ggggcatcat tcccagagc                                                 19

<210> SEQ ID NO 38
<211> LENGTH: 21
<212> TYPE: DNA
<213> ORGANISM: Rattus norvegicus
<220> FEATURE:
<223> OTHER INFORMATION: Kif17 primer AS

<400> SEQUENCE: 38
gtccatgcac acggtacaca a                                              21

<210> SEQ ID NO 39
<211> LENGTH: 21
<212> TYPE: DNA
<213> ORGANISM: Rattus norvegicus
<220> FEATURE:
<223> OTHER INFORMATION: Stx17 primer S

<400> SEQUENCE: 39
tcaaagtggc aggaattgca g                                              21

<210> SEQ ID NO 40
<211> LENGTH: 23
<212> TYPE: DNA
<213> ORGANISM: Rattus norvegicus
<220> FEATURE:
<223> OTHER INFORMATION: Stx17 primer AS

<400> SEQUENCE: 40
ttaggcttca caggtggaaa att                                            23

<210> SEQ ID NO 41
<211> LENGTH: 20

<212> TYPE: DNA
<213> ORGANISM: Rattus norvegicus
<220> FEATURE:
<223> OTHER INFORMATION: Kcnk1 primer S

<400> SEQUENCE: 41
gaggagctgc cttagaggac                                              20

<210> SEQ ID NO 42
<211> LENGTH: 21
<212> TYPE: DNA
<213> ORGANISM: Rattus norvegicus
<220> FEATURE:
<223> OTHER INFORMATION: Kcnk1 primer AS

<400> SEQUENCE: 42
ctcgggaaat tggaattggg a                                            21

<210> SEQ ID NO 43
<211> LENGTH: 19
<212> TYPE: DNA
<213> ORGANISM: Rattus norvegicus
<220> FEATURE:
<223> OTHER INFORMATION: Xpo4 primer S

<400> SEQUENCE: 43
cccccagaag tgatcgctc                                               19

<210> SEQ ID NO 44
<211> LENGTH: 23
<212> TYPE: DNA
<213> ORGANISM: Rattus norvegicus
<220> FEATURE:
<223> OTHER INFORMATION: Xpo4 primer AS

<400> SEQUENCE: 44
ttgcaggcat attttggaaa cca                                          23

<210> SEQ ID NO 45
<211> LENGTH: 21
<212> TYPE: DNA
<213> ORGANISM: Rattus norvegicus
<220> FEATURE:
<223> OTHER INFORMATION: Csnk2a primer S

<400> SEQUENCE: 45
aggatagcca aggttctggg a                                            21

<210> SEQ ID NO 46
<211> LENGTH: 20
<212> TYPE: DNA
<213> ORGANISM: Rattus norvegicus
<220> FEATURE:
<223> OTHER INFORMATION: Csnk2A primer AS

<400> SEQUENCE: 46
gacactcccg taagcgatgg                                              20

<210> SEQ ID NO 47
<211> LENGTH: 20
<212> TYPE: DNA
<213> ORGANISM: Rattus norvegicus
<220> FEATURE:
<223> OTHER INFORMATION: Adrb1 primer S

<400> SEQUENCE: 47
gaaccctgca acctgtcgtc                                                  20

<210> SEQ ID NO 48
<211> LENGTH: 19
<212> TYPE: DNA
<213> ORGANISM: Rattus norvegicus
<220> FEATURE:
<223> OTHER INFORMATION: Adrb1 primer AS

<400> SEQUENCE: 48
ggtatgggcc tactcgtgg                                                   19

<210> SEQ ID NO 49
<211> LENGTH: 23
<212> TYPE: DNA
<213> ORGANISM: Rattus norvegicus
<220> FEATURE:
<223> OTHER INFORMATION: Pten primer S

<400> SEQUENCE: 49
tggattcgac ttagacttga cct                                              23

<210> SEQ ID NO 50
<211> LENGTH: 22
<212> TYPE: DNA
<213> ORGANISM: Rattus norvegicus
<220> FEATURE:
<223> OTHER INFORMATION: Pten primer AS

<400> SEQUENCE: 50
ctgagagaca ttatgacacc gc                                               22

<210> SEQ ID NO 51
<211> LENGTH: 22
<212> TYPE: DNA
<213> ORGANISM: Rattus norvegicus
<220> FEATURE:
<223> OTHER INFORMATION: Map2k3 primer S

<400> SEQUENCE: 51
gcctcagacc aaaggaaaat cc                                               22

<210> SEQ ID NO 52
<211> LENGTH: 19
<212> TYPE: DNA
<213> ORGANISM: Rattus norvegicus
<220> FEATURE:
<223> OTHER INFORMATION: Map2k3 primer AS

<400> SEQUENCE: 52
ctgtgtccaa ccccacacc                                                   19

<210> SEQ ID NO 53
<211> LENGTH: 19
<212> TYPE: DNA
<213> ORGANISM: Rattus norvegicus
<220> FEATURE:
<223> OTHER INFORMATION: Ucqr10 primer S

<400> SEQUENCE: 53
atcccttcgc gcctgtact                                                   19

<210> SEQ ID NO 54
<211> LENGTH: 19
<212> TYPE: DNA
<213> ORGANISM: Rattus norvegicus
<220> FEATURE:
<223> OTHER INFORMATION: Ucqr10 primer AS

<400> SEQUENCE: 54
agacgcgatc tacgagcac                                              19

<210> SEQ ID NO 55
<211> LENGTH: 19
<212> TYPE: DNA
<213> ORGANISM: Rattus norvegicus
<220> FEATURE:
<223> OTHER INFORMATION: Nipsnap1 primer S

<400> SEQUENCE: 55
cacggcggct attcacgaa                                              19

<210> SEQ ID NO 56
<211> LENGTH: 21
<212> TYPE: DNA
<213> ORGANISM: Rattus norvegicus
<220> FEATURE:
<223> OTHER INFORMATION: Nipsnap1 primer AS

<400> SEQUENCE: 56
tgaaggaagc tggttccgtt c                                           21

<210> SEQ ID NO 57
<211> LENGTH: 18
<212> TYPE: DNA
<213> ORGANISM: Rattus norvegicus
<220> FEATURE:
<223> OTHER INFORMATION: Xbp1(Del) primer S

<400> SEQUENCE: 57
cctgagcccg gaggagaa                                               18

<210> SEQ ID NO 58
<211> LENGTH: 18
<212> TYPE: DNA
<213> ORGANISM: Rattus norvegicus
<220> FEATURE:
<223> OTHER INFORMATION: Xbp1(Del) primer AS

<400> SEQUENCE: 58
cagcgcagac tgctcgag                                               18

<210> SEQ ID NO 59
<211> LENGTH: 20
<212> TYPE: DNA
<213> ORGANISM: Rattus norvegicus
<220> FEATURE:
<223> OTHER INFORMATION: Ws1 primer S

<400> SEQUENCE: 59
ccatcaacat gctcccgttc                                             20

<210> SEQ ID NO 60
<211> LENGTH: 16
<212> TYPE: DNA
<213> ORGANISM: Rattus norvegicus
<220> FEATURE:
<223> OTHER INFORMATION: Ws1 primer AS

<400> SEQUENCE: 60
atggcgaggc ctaccc                                                 16

```
<210> SEQ ID NO 61
<211> LENGTH: 19
<212> TYPE: DNA
<213> ORGANISM: Rattus norvegicus
<220> FEATURE:
<223> OTHER INFORMATION: Edem primer S

<400> SEQUENCE: 61
aacccaatgg cctgtctgg                                                  19

<210> SEQ ID NO 62
<211> LENGTH: 19
<212> TYPE: DNA
<213> ORGANISM: Rattus norvegicus
<220> FEATURE:
<223> OTHER INFORMATION: Edem primer AS

<400> SEQUENCE: 62
cgcaagttcc agagggctt                                                  19

<210> SEQ ID NO 63
<211> LENGTH: 19
<212> TYPE: DNA
<213> ORGANISM: Rattus norvegicus
<220> FEATURE:
<223> OTHER INFORMATION: Bip primer S

<400> SEQUENCE: 63
tcatcggacg cacttggaa                                                  19

<210> SEQ ID NO 64
<211> LENGTH: 21
<212> TYPE: DNA
<213> ORGANISM: Rattus norvegicus
<220> FEATURE:
<223> OTHER INFORMATION: Bip primer AS

<400> SEQUENCE: 64
tcttgccatt caaggtggtt g                                               21

<210> SEQ ID NO 65
<211> LENGTH: 24
<212> TYPE: DNA
<213> ORGANISM: Rattus norvegicus
<220> FEATURE:
<223> OTHER INFORMATION: Actin primer S

<400> SEQUENCE: 65
ctcaggagga gcaatgatct tgat                                            24

<210> SEQ ID NO 66
<211> LENGTH: 20
<212> TYPE: DNA
<213> ORGANISM: Rattus norvegicus
<220> FEATURE:
<223> OTHER INFORMATION: Actin primer AS

<400> SEQUENCE: 66
tgcctgggta catggtggta                                                 20

<210> SEQ ID NO 67
<211> LENGTH: 20
<212> TYPE: DNA
<213> ORGANISM: Mus musculus

<400> SEQUENCE: 67
```

```
ccatgggaag atgttctggg                                              20
```

<210> SEQ ID NO 68
<211> LENGTH: 63
<212> TYPE: DNA
<213> ORGANISM: Mus musculus

<400> SEQUENCE: 68

```
acgtagatct ttagacgtaa tctggaacat cgtatgggta gacactaatc agctggggga  60
aaa                                                                63
```

<210> SEQ ID NO 69
<211> LENGTH: 141
<212> TYPE: PRT
<213> ORGANISM: Woodchuck hepatitis virus

<400> SEQUENCE: 69

```
Met Ala Ala Arg Leu Cys Cys His Leu Asp Ser Ala Arg Asp Val Leu
1               5                   10                  15

Leu Leu Arg Pro Phe Gly Pro Gln Ser Ser Gly Pro Pro Phe Pro Arg
                20                  25                  30

Pro Ser Ala Gly Ser Ala Ala Ser Pro Ala Ser Ser Leu Ser Thr Ser
            35                  40                  45

Asp Glu Ser Asp Phe Pro Leu Gly Arg Leu Pro Ala Cys Phe Ala Ser
    50                  55                  60

Ala Ser Gly Pro Cys Cys Leu Val Phe Thr Cys Ala Glu Leu Arg Thr
65                  70                  75                  80

Met Asp Ser Thr Val Asn Phe Val Ser Trp His Ala Asn Arg Gln Leu
                85                  90                  95

Gly Met Pro Ser Lys Asp Leu Trp Thr Pro Tyr Ile Lys Asp Gln Leu
            100                 105                 110

Leu Thr Lys Trp Glu Glu Gly Ser Ile Asp Pro Arg Leu Ser Ile Phe
        115                 120                 125

Val Leu Gly Gly Cys Arg His Lys Cys Met Arg Leu Leu
    130                 135                 140
```

<210> SEQ ID NO 70
<211> LENGTH: 20
<212> TYPE: DNA
<213> ORGANISM: Rattus norvegicus
<220> FEATURE:
<223> OTHER INFORMATION: Gria4 primer

<400> SEQUENCE: 70

```
gggaggtgac tccaaggaca                                              20
```

<210> SEQ ID NO 71
<211> LENGTH: 19
<212> TYPE: DNA
<213> ORGANISM: Rattus norvegicus
<220> FEATURE:
<223> OTHER INFORMATION: Ryr3 primer

<400> SEQUENCE: 71

```
accagcagga gcaagtacg                                               19
```

<210> SEQ ID NO 72
<211> LENGTH: 21
<212> TYPE: DNA
<213> ORGANISM: Rattus norvegicus

```
<220> FEATURE:
<223> OTHER INFORMATION: Kcnk1 primer

<400> SEQUENCE: 72
gaggagctgc cttatgagga c                                           21

<210> SEQ ID NO 73
<211> LENGTH: 21
<212> TYPE: DNA
<213> ORGANISM: Rattus norvegicus
<220> FEATURE:
<223> OTHER INFORMATION: Ttr primer

<400> SEQUENCE: 73
ttacagccac gtctacagca g                                           21

<210> SEQ ID NO 74
<211> LENGTH: 21
<212> TYPE: DNA
<213> ORGANISM: Rattus norvegicus
<220> FEATURE:
<223> OTHER INFORMATION: Reln primer

<400> SEQUENCE: 74
ggggaggtac aggatgtgga t                                           21

<210> SEQ ID NO 75
<211> LENGTH: 19
<212> TYPE: DNA
<213> ORGANISM: Rattus norvegicus
<220> FEATURE:
<223> OTHER INFORMATION: Gria1 Primer

<400> SEQUENCE: 75
ctcgcccttg tcgtaccac                                              19

<210> SEQ ID NO 76
<211> LENGTH: 23
<212> TYPE: DNA
<213> ORGANISM: Rattus norvegicus
<220> FEATURE:
<223> OTHER INFORMATION: Gria2 primer

<400> SEQUENCE: 76
cactctcgat gccatatacg ttg                                         23

<210> SEQ ID NO 77
<211> LENGTH: 22
<212> TYPE: DNA
<213> ORGANISM: Rattus norvegicus
<220> FEATURE:
<223> OTHER INFORMATION: Gria3 primer

<400> SEQUENCE: 77
acgtggtagt tcaaatggaa gg                                          22

<210> SEQ ID NO 78
<211> LENGTH: 21
<212> TYPE: DNA
<213> ORGANISM: Rattus norvegicus
<220> FEATURE:
<223> OTHER INFORMATION: Gria4 primer

<400> SEQUENCE: 78
ccagtgatgg ataacctggc t                                           21
```

<210> SEQ ID NO 79
<211> LENGTH: 23
<212> TYPE: DNA
<213> ORGANISM: Rattus norvegicus
<220> FEATURE:
<223> OTHER INFORMATION: Myo5b primer

<400> SEQUENCE: 79
tggcgtagtt gatacaaaac tgt                                          23

<210> SEQ ID NO 80
<211> LENGTH: 21
<212> TYPE: DNA
<213> ORGANISM: Rattus norvegicus
<220> FEATURE:
<223> OTHER INFORMATION: Creb primer

<400> SEQUENCE: 80
gcagcttgaa caacaacttg g                                            21

<210> SEQ ID NO 81
<211> LENGTH: 22
<212> TYPE: DNA
<213> ORGANISM: Rattus norvegicus
<220> FEATURE:
<223> OTHER INFORMATION: Bdnf primer

<400> SEQUENCE: 81
cgcgtcctta tggttttctt cg                                           22

<210> SEQ ID NO 82
<211> LENGTH: 22
<212> TYPE: DNA
<213> ORGANISM: Rattus norvegicus
<220> FEATURE:
<223> OTHER INFORMATION: CamkII primer

<400> SEQUENCE: 82
ccattaactg aacgctggaa ct                                           22

<210> SEQ ID NO 83
<211> LENGTH: 20
<212> TYPE: DNA
<213> ORGANISM: Rattus norvegicus
<220> FEATURE:
<223> OTHER INFORMATION: Ryr1 primer

<400> SEQUENCE: 83
caccggcctc cacagtattg                                              20

<210> SEQ ID NO 84
<211> LENGTH: 20
<212> TYPE: DNA
<213> ORGANISM: Rattus norvegicus
<220> FEATURE:
<223> OTHER INFORMATION: Ryr2 primer

<400> SEQUENCE: 84
cagagcccga atcatccagc                                              20

<210> SEQ ID NO 85
<211> LENGTH: 21
<212> TYPE: DNA
<213> ORGANISM: Rattus norvegicus
<220> FEATURE:
<223> OTHER INFORMATION: Ryr3 primer

<400> SEQUENCE: 85
ggggtcgtgt caaagtagtc a                                              21

<210> SEQ ID NO 86
<211> LENGTH: 22
<212> TYPE: DNA
<213> ORGANISM: Rattus norvegicus
<220> FEATURE:
<223> OTHER INFORMATION: Nr2a primer

<400> SEQUENCE: 86
tcagtgcggt tcatcaataa cg                                             22

<210> SEQ ID NO 87
<211> LENGTH: 20
<212> TYPE: DNA
<213> ORGANISM: Rattus norvegicus
<220> FEATURE:
<223> OTHER INFORMATION: Nr2b primer

<400> SEQUENCE: 87
gcttcctggt ccgtgtcatc                                                20

<210> SEQ ID NO 88
<211> LENGTH: 20
<212> TYPE: DNA
<213> ORGANISM: Rattus norvegicus
<220> FEATURE:
<223> OTHER INFORMATION: Pp2b/Caln primer

<400> SEQUENCE: 88
cccgatttgt ccaagtccag                                                20

<210> SEQ ID NO 89
<211> LENGTH: 21
<212> TYPE: DNA
<213> ORGANISM: Rattus norvegicus
<220> FEATURE:
<223> OTHER INFORMATION: Kif17 primer

<400> SEQUENCE: 89
ttgtgtaccg tgtgcatgga c                                              21

<210> SEQ ID NO 90
<211> LENGTH: 23
<212> TYPE: DNA
<213> ORGANISM: Rattus norvegicus
<220> FEATURE:
<223> OTHER INFORMATION: Stx17 primer

<400> SEQUENCE: 90
aattttccac ctgtgaagcc taa                                            23

<210> SEQ ID NO 91
<211> LENGTH: 21
<212> TYPE: DNA
<213> ORGANISM: Rattus norvegicus
<220> FEATURE:
<223> OTHER INFORMATION: Kcnk1 primer

<400> SEQUENCE: 91
tcccaattcc aatttcccga g                                              21

<210> SEQ ID NO 92

```
<211> LENGTH: 23
<212> TYPE: DNA
<213> ORGANISM: Rattus norvegicus
<220> FEATURE:
<223> OTHER INFORMATION: Xpo4 primer

<400> SEQUENCE: 92
tggtttccaa aatatgcctg caa                                              23

<210> SEQ ID NO 93
<211> LENGTH: 20
<212> TYPE: DNA
<213> ORGANISM: Rattus norvegicus
<220> FEATURE:
<223> OTHER INFORMATION: Csnk2A primer

<400> SEQUENCE: 93
ccatcgctta cgggagtgtc                                                  20

<210> SEQ ID NO 94
<211> LENGTH: 19
<212> TYPE: DNA
<213> ORGANISM: Rattus norvegicus
<220> FEATURE:
<223> OTHER INFORMATION: Adrb1 primer

<400> SEQUENCE: 94
ccacgagtag gcccatacc                                                   19

<210> SEQ ID NO 95
<211> LENGTH: 22
<212> TYPE: DNA
<213> ORGANISM: Rattus norvegicus
<220> FEATURE:
<223> OTHER INFORMATION: Pten primer

<400> SEQUENCE: 95
gcggtgtcat aatgtctctc ag                                               22

<210> SEQ ID NO 96
<211> LENGTH: 19
<212> TYPE: DNA
<213> ORGANISM: Rattus norvegicus
<220> FEATURE:
<223> OTHER INFORMATION: Map2k3 primer

<400> SEQUENCE: 96
ggtgtggggt tggacacag                                                   19

<210> SEQ ID NO 97
<211> LENGTH: 19
<212> TYPE: DNA
<213> ORGANISM: Rattus norvegicus
<220> FEATURE:
<223> OTHER INFORMATION: Ucqr10 primer

<400> SEQUENCE: 97
gtgctcgtag atcgcgtct                                                   19

<210> SEQ ID NO 98
<211> LENGTH: 21
<212> TYPE: DNA
```

```
<213> ORGANISM: Rattus norvegicus
<220> FEATURE:
<223> OTHER INFORMATION: Nipsnap1 primer

<400> SEQUENCE: 98
gaacggaacc agcttccttc a                                             21

<210> SEQ ID NO 99
<211> LENGTH: 18
<212> TYPE: DNA
<213> ORGANISM: Rattus norvegicus
<220> FEATURE:
<223> OTHER INFORMATION: Xbp1(Del) primer

<400> SEQUENCE: 99
ctcgagcagt ctgcgctg                                                 18

<210> SEQ ID NO 100
<211> LENGTH: 16
<212> TYPE: DNA
<213> ORGANISM: Rattus norvegicus
<220> FEATURE:
<223> OTHER INFORMATION: Ws1 primer

<400> SEQUENCE: 100
gggtaggcct cgccat                                                   16

<210> SEQ ID NO 101
<211> LENGTH: 19
<212> TYPE: DNA
<213> ORGANISM: Rattus norvegicus
<220> FEATURE:
<223> OTHER INFORMATION: Edem primer

<400> SEQUENCE: 101
aagccctctg gaacttgcg                                                19

<210> SEQ ID NO 102
<211> LENGTH: 21
<212> TYPE: DNA
<213> ORGANISM: Rattus norvegicus
<220> FEATURE:
<223> OTHER INFORMATION: Bip primer

<400> SEQUENCE: 102
caaccacctt gaatggcaag a                                             21

<210> SEQ ID NO 103
<211> LENGTH: 20
<212> TYPE: DNA
<213> ORGANISM: Rattus norvegicus
<220> FEATURE:
<223> OTHER INFORMATION: Actin primer

<400> SEQUENCE: 103
taccaccatg tacccaggca                                               20
```

AAV/XBP1S-HA VIRUS, GENE THERAPY METHOD AND USE THEREOF IN THE OPTIMISATION AND IMPROVEMENT OF LEARNING, MEMORY AND COGNITIVE CAPACITIES

"AAV/XBP1s-HA, virus, method of genetic treatment and its use in the optimitzation and improvement of cognitive abilities, memory and learning."

SEQUENCE LISTING

The instant application contains a Sequence Listing which has been submitted electronically in ASCII format and is hereby incorporated by reference in its entirety. Said ASCII copy, created on Dec. 28, 2021, is named 0412-0002US1_SL.txt 0412-0002US1_SL_7_Jan_2022.txt and is 19,885 bytes in size.

TECHNICAL FIELD OF THIS INVENTION

This invention is applied in the field of medicine, specifically in the learning process and formation of the memory, by using the adeno-associated viruses (AAV) that over-express the transcription factor XBP1 in neurons of the central nervous system (CNS), preferably in the hippocampus, recovering and improving the performance of the memory and learning.

BACKGROUND INFORMATION AND DESCRIPTION OF THE STATE OF THE ART

Scientific research on diseases of the CNS has been of great interest in recent years, above all the diseases related to cognitive alterations. The treatment of diseases related with the memory or learning do not have a therapeutic approach to reduce symptoms.

In the search for treatment of these cognitive diseases, the transcription factor known as XBP1 has been identified whose function is involved in the biological and molecular mechanisms of the memory and learning processes.

The pharmacological therapies that exist today are directed mainly to the endogenous decrease of XBP1 through the control of a sensor upstream, IRE1, as presented in patent US2013197023. The activation of IRE1 catalyzes the unconventional scission of an intron of 26 nucleotides expressed in the mARN of Xbp1, in a mechanical manner similar to a pre-tRNA splicing. The elimination of this intron causes a reading framework change in the codification sequence of XBP1 resulting in the translation of a protein of a larger size of 376 residues, of 54 kDa, named XBP1s. In the absence of the scission, the protein of 261 residues is translated, of 33 kDa, named as XBP1u from the English, unspliced. It has been described that the proportion XBP1s/XBP1u is correlated with the level of expression of the gene regulated by XBP1s increasing the folding capacity of the endoplasmic reticulum (ER) required to maintain the cellular homeostasis. The negative regulation of the expression XBP1, has been seen implied in the generation of neuroprotection in Huntington's disease and in amyotrophic lateral sclerosis (ELA), as presented in patent application WO2010/008860.

Another relevant patent with regard to the measuring of stress in ER, where the transcription factor XBP1 is implied, is the Japanese patent JP2007129970.

In general, this development refers to the memory process, to the consolidation and storage of new information in the brain. Short-term memory is defined as the retaining of information for short periods of time without generating neuronal connections or protein synthesis. On the other hand, the long-term memory is defined when new neuronal synapses are produced and the information compiled is stored for weeks, months, or even years with the dependence of the production of new mARN and proteins (1).

One of the many components implicated in neuronal development is the neurotrophic factor derived from the brain (BDNF), which is a neurotrophin that regulates neuronal development, the neuroplasticity and synaptogenesis in the CNS (2). Different studies have associated BNDF with learning mechanisms and the formation of the memory (3, 4, 5, 6, 7 and 8). The expression levels of BDNF are controlled dynamically by behavior; nevertheless, their transcriptional regulation is complex. Various transcription factors associated to the regulation of the BDNF have been described, such as the Calcium transcription response factor (CaRF) and the binding protein to the response element of cAMP (CREB; 9 and 10). Although for the time being the fine control mechanisms of the BDNF expression have been poorly studied.

SUMMARY OF THE INVENTION

The formation of memory and learning are based on the induction of the expression of new genes in different regions of the brain, although mainly in the hippocampus where BDNF has been indicated as one of the principle factors in mediating this function within a large number of other factors involved. In the search for different regulators of the BDNF expression, in its proximal promoter region, a functional binding site was identified for the transcription factor XBP1, a key component of the response to misfolded proteins (UPR). The analysis of the gene expression profile that regulates the XBP1 factor revealed that it also regulates a group of genes among which we can mention: GLIA3 (ionotropic glutamate receptor, AMPA 3 (alfa3)); BDNF (factor derived from cerebral neurotrophin); and KIF17 (family of the kinesins 17); therefore, XBP1 regulates genes implicated in learning and memory. The analysis of the behavior of mice deficient for the XBP1 transcription factor in their neurons, revealed a reduction in the formation of the contextual memory and the deterioration of the long-term empowerment (17).

Surprisingly, the increase of the expression of XBP1s either because of the overexpression in the CNS of XBP1s in transgenic mice or by means of the delivery via a virus directly in the hippocampus, manages to improve the performance of memory tasks. This result reveals a new unforeseen function for XBP1 in the cognitive processes. The above, endorsed by the recent discovery of polymorphisms in the promotor of XBP1, as a risk factor for Alzheimer's disease and bipolar disorders, have caused the strategies to improve the activity of XBP1s in the brain to be translated in beneficial effects for the treatment of memory, cognitive and learning disorders.

A relevant data in this invention is the homology level in the XBP1 sequences in mice and humans, which is over 75%, preferably 83%. The sequences XBP1s and XBP1u human can be seen in tables number VIII and IX respectively.

A first aspect of this invention is related with a method to improve and optimize the long-term memory, the cognitive processes and memory in mammals, preferably in humans, utilizing a virus that induces the neuronal overexpression of XBP1s in the brain, preferably in the hippocampus.

A second aspect of this invention provides a therapeutic treatment method to improve and optimize the long-term memory and its cognitive and learning capacities. The method consists of the intravenous and/or intraperitoneal and/or intracranial and/or intramedular and/or intranasal and/or intraneural and/or any means that introduces the virus into the brain passing the hematoencephalic barrier of a patient or subject. The virus induces the neural overexpression of XBP1s in a dose range of $1^6$ to $1^{30}$ viral units per individual.

A third aspect of this invention is a form of intravenous pharmaceutical composition and/or intraperitoneal and/or intracranial and/or intramedular and/or intranasal and/or intraneural and/or any form that conducts the virus that induces the neuronal overexpression of XBP1s to the brain, preferably to the hippocampus, passing the hematoencephalic barrier, with dose ranges such as those presented previously and a pharmaceutically acceptable vehicle for its use in the optimization and improvement of the long-term memory, cognitive and learning capacities of a human patient.

A fourth aspect of this invention is the use of a virus that induces the neuronal overexpression of XBP1s and its protein derivative compounds because it can be used to prepare a medicine useful in improving the memory, cognitive processes and learning.

A fifth aspect of this invention is a virus of the adeno-associated type (AAV) that presents the same sequence of the virus and an insert with a nucleotide sequence described in Table III or any of its variants, contained in the plasmid deposited in the international agency of biologic deposits, American Type Culture Collection (ATCC), with deposit number PTA-121708, where the neuronal transcription factor XBP1 is overexpressed, preferably XBP1s in the brain, principally in the hippocampus.

A sixth aspect of this invention is the plasmid with the fragment of nucleic acid of the virus and an insert with a nucleotide sequence described in Table III contained in the plasmid deposited in the international agency of biological deposits, American Type Culture Collection (ATCC), with deposit number PTA-121708, or any variant of this fragment, that codifies and overexpresses the neuronal transcription factor XBP1, preferably XBP1s.

This patent also presents the sequence of the plasmid with the fragment of nucleic acid of the virus and an insert with a nucleotide sequence described in Table X or any variable of this fragment, that codifies and overexpresses the neuronal transcription factor XBP1, preferably human XBP1s.

Deposit of Microorganisms

The plasmid pAAV-XBP1s-HA was deposited on 5 Nov. 2014 under terms of the Budapest Treaty with the American Type Culture Collection (ATCC), 10801 University Boulevard Manassas, Va. 20110-2209, under the deposit number PTA-121708.

DETAILED DESCRIPTION OF THE INVENTION

It must be understood that this invention is not limited to the particular methodology, compounds, materials, manufacturing techniques, uses and applications described here, because these can vary. It must also be understood that the terminology employed here is used with the only purpose of describing a particular representation and does not attempt to limit the perspective and potential of this invention.

It must be noted that the use and method, here, in the list of claims and in the entire text that the singular does not exclude the plural, except when the context clearly implies it. Then, for example, the reference to a "use or method" is a reference to one or more uses or methods and includes equivalents known to those who are knowledgeable in the matter (the art). Similarly, as another example, the reference to "a step", "a stage" or to "a mode" is a reference to one or more steps, stages or modes and can include sub steps, stages or modes, implied and/or supervening.

All the conjunctions used must be understood in their less restrictive sense and most inclusive possible. So, for example, the conjunction "or" must be understood in its orthodox logical sense, and not as an "excluding or", unless the context or the text specifically needs or indicates it. The structures, materials and/or elements described must be understood to refer also to those equivalents functionally and thus avoid interminable exhaustive enumerations.

The expressions used to indicate approximations or conceptualizations must be understood thus, unless the context demands a different interpretation.

All the names and technical and/or scientific terms employed here have the common meaning they are given by a common person, qualified in these matters, unless specifically indicated otherwise.

The methods, techniques, elements, compounds and compositions are described, although methods, techniques, compounds and compositions, similar and/or equivalent to those described, can be used or preferred in practice and/or in tests of this invention.

The patents and other publications are incorporated as references, with the purpose of describing and/or informing, for example, the methodologies described in those publications, that may be useful in relation to this invention.

These publications are included only for their information prior to the registration date of this patent application.

In this respect, nothing must be considered as an admission or acceptance, rejection or exclusion, that the authors and/or inventors are not entitled to do so, or that these publications are predated in virtue of other previous ones, or for any other reason.

This invention describes vectors based on the serotypes AAV6, AAV7, AAV8, AAV9 and adeno-associated viruses capable of efficiently mediating the transferences of genes to the brain, preferably to the hippocampus when administered locally (FIG. 12/17, left panel).

The systemic administration of these vectors also leads to an efficient supply of genes both to the brain and the hippocampus. Although the delivery of genes mediated by the vector AAV6 is more efficient, the delivery, in the case of systemic administration, is not restricted only to the brain or hippocampus. This invention presents that the vector of AAV6 with proximal regions of the promoter of the XBP1 transcription factor, permits the generation of a response in a cluster of factors of unspecific interest in the brain and specifically in the hippocampus. In particular, the local administration of the AAV6 vector that includes an expression cassette in which a heterologous gen XBP1 is under the control of the PGK promoter, achieves an improvement in the memory and in the cognitive capacity in healthy individuals in vivo. (FIG. 12/17 right panel and FIG. 13/17).

I. Definition of General Terms and Expressions

The terms "adeno-associated virus", "AAV virus", "AAV virion", "AAV viral particle", and "particle of AAV", as used in this document are interchangeable, they refer to a viral particle made up of at least one protein of the capsid of AAV (preferably by all the proteins of the capsid of a serotype of AAV in particular) and a polynucleotide of the encapsidated genome of AAV. If the particle includes a heterologous polynucleotide (that is, a polynucleotide other than a native type genome of AAV like a transgene to be delivered to a mammal cell) flanked by the inverted terminal repetitions of the AAV, that is known typically as a "vector of particles of AAV" or "vector of AAV". AAV refers to a virus that belongs to the Dependovirus of the Parvoviridae family. The genome of AAV is approximately 4.7 kilobases long and is made up of deoxyribonucleic acid of simple chain (ssDNA) that can be censored as positive or negative. The genome includes inverted terminal repetitions (ITR) at both ends of the DNA chain, and two open reading frames (ORFs): REP and CAP (Replicase and Capsid). The Rep frame is formed by four superimposed genes that codify for REP proteins (REP 78, REP 68, REP 52 and REP 40) required for the life cycle of the AAV. The CAP frame contains overlap nucleotides of 20 sequences of proteins of the capsid: VP1, VP2 and VP3, that interact with each other to form a capsid with an icosahedral symmetry (11), as shown in FIG. 15/17.

The term "adeno-associated virus IRT" or AAV ITR" as it is used here, refers to the inverted terminal that is repeated and is present at both ends of the DNA chain of the genome in an adeno-associated virus. The ITR sequences are required for the efficient multiplication of the AAV genome. Another characteristic of these sequences is their capacity to form a fork. This characteristic contributes to its auto-copy that permits the independent primary synthesis of the second DNA chain. The IRTs also proved to be necessary for both the integration of the DNA of the native type AAV in the genome of the host cell and its rescue, as well as for the efficient encapsidation of the DNA of the AAV combined with the generation of its complete assembly.

The term "AAV6", as used in this invention, refers to the serotype 6 of the adeno-associated virus with a sequence of the genome as defined in GenBank access number AF028704.1, that is found in the webpage: http://www.ncbi.nlm.nih.gov/

The term "vector of AAV", as used in this invention, also refers to a vector that includes one or more polynucleotides of interest (or transgenes) that are flanked by sequences of terminal repetition of AAV (ITR). These vectors of AAV can be replicated and packed in infectious viral particles when they are present in a host cell that has been transfected with a vector that codifies and expresses the genes REP and CAP (that is, the proteins AAV REP and CAP), and where the host cell has been transfected with a vector that codifies and expresses a protein of the reading frame of the adenovirus E4orf6. When a vector of AAV is incorporated in a larger polynucleotide (for example, in a chromosome or in another vector such as a plasmid used for cloning or transfection), then the vector of AAV is named typically as a "pro-vector". The pro-vector can be "rescued" by replication and encapsidation in the presence of the packaging functions of the AAV and the necessary auxiliary functions provided by E4orf6.

The term "specific binding site for the transcription regulating region of XBP1", as used in this invention, refers to a sequence of nucleic acids that serve as a promoter (that is, regulate the expression of a selected nucleic acid sequence, joined operatively to the promotor) and that affects the expression of a selected nucleic acid sequence in cells of specific tissues, such as the nerve cells. The specific binding site for the regulating region of the transcription of the neuronal tissue can be constitutive or inducible.

The term "CAP gene" or "CAP gene of AAV", as used in this invention, refers to a gene that codifies for a CAP protein. The term "CAP protein", as used here, refers to a polypeptide that has an activity of at least one functional activity of the CAP protein of a native AAV (VP1, VP2, VP3). Examples of functional activities of the VP1, VP2 and VP3 proteins include the capacity to induce the formation of a capsid, ease the accumulation of single strand DNA, ease the packaging of the DNA of AAV in the capsid (that is, the encapsidation), join cellular receptors and ease the entry of the virion to a host.

The term "capsid", as used in this invention, refers to the structure in which the viral genome is packaged. A capsid consists of an oligomeric structure with structural subunits of CAP proteins. For example, the AAV has an icosahedral capsid formed by the interaction of three proteins of the capsid: VP1, VP2 and VP3.

The term "composition of cells" as used in this document, refers to a compound type material that consists of the cells of the invention and at least another component. The composition may be formulated as a single formulation or can be presented as separate formulations of each one of the components, that can be combined for joint usage as a combined preparation. The composition can be a kit of parts, where each one of the components is formulated and packed individually.

The term "constituent promotor", as used in this invention, refers to a promotor whose activity is maintained at a relatively constant level in an entire organism, or during most of the experimental stages, with little or no consideration of the environmental and external conditions of the cell.

The term "enhancer", as used here, refers to an element of the DNA sequence to which the transcription factors are joined to increase the transcription of the genes.

The term "expression cassette", as used here, refers to a construction of nucleic acids, generated by recombination or synthetically, with a series of specific elements of the nucleic acids, that permit the transcription of a particular nucleic acid in a target cell.

The term "genes that provide help functions", as used here, refers to genes that codify polypeptides, that execute functions on which the AAV is dependent for the replication (i.e., "help functions"). The auxiliary functions include the functions necessary for the replication of AAV, including those fragments involved in the activation of the transcription of AAV genes, the specific stages of the splicing of mARN of AAV, the replication of the DNA of AAV, the synthesis of the products of CAP and the assembling of the capsid of AAV. Accessory viral functions can be derived from any of the known auxiliary virus such as adenovirus, herpes virus, lentivirus and the vaccinia virus. The auxiliary functions include, without limitation, lentivirus WHV.

The term "linked operatively", as described in this document, refers to the functional relationship and localization of a promotor sequence with regard to a polynucleotide of interest (for example, a promotor or enhancer is linked operatively to a codifying sequence that affects the transcription of this sequence). Generally, a promotor linked operatively is contiguous to the sequence of interest. Nevertheless, an enhancer does not have to be contiguous to the sequence of interest to control its expression.

The term "administered locally", as used here, means that the polynucleotides, vectors, polypeptides and/or pharmaceutical compositions of the invention are administered to the subject in or close to a specific site.

The terms "pharmaceutically acceptable carriers", "pharmaceutically acceptable solvents", "pharmaceutically acceptable excipient" or "Pharmaceutically acceptable vehicle", are interchangeable in this document, they refer to a nontoxic solid, semisolid or filling liquid, solvent or encapsulation material or an auxiliary formulation for any conventional type. A pharmaceutically acceptable carrier is essentially nontoxic for the containers employed in the dosages and concentrations and is compatible with other ingredients of the formulation. The number and nature of the pharmaceutically acceptable vehicles depends on the form of administration desired. The pharmaceutically acceptable vehicles are known and can be prepared by methods that are well known in the art (12).

The term "promotor", as used here, refers to a nucleic acid that functions to control the transcription of one or more polynucleotides, situated upstream of the sequence of the polynucleotide(s), and that is identified structurally by the presence of a binding site for DNA dependent of the ARN Polymerase, the initiation sites of the transcription, and any other sequence of DNA, including, but not limited to, the binding sites of transcription factors, repressor, and binding sites to activating protein, and any other sequences of nucleotides known in the technique to act directly or indirectly to regulate the amount of transcription based on the promotor. A "tissue-specific" promotor is only activated in specific types of cells or differentiated tissues.

The term "polynucleotide", as used here, refers to a molecule of nucleic acid, either DNA or ARN, that contains deoxyribonucleotides or ribonucleotides respectively. The nucleic acid can be double-chain, single-chain, or contain parts of both double or single chain. The term "polynucleotide" includes, but is not limited to, sequences of nucleic acids with the capacity to codify a polypeptide and sequences of nucleic acids partially or totally complementary to an endogenous polynucleotide of the cell or the subject treated with the same so that, after the transcription of the same, a molecule of ARN is generated (for example, microARN, shARN, siARN) capable of hybridizing and inhibiting the expression of the endogenous polynucleotide.

In this document, the term "strand" refers to a sequence of continuous nucleotides (including or not including natural modified or non-natural nucleotides). The two or more threads can be, or each one forms a part of separate molecules, or can be covalently interconnected, for example, by a hookup, for example, a linker such as polyethylene glycol to form a molecule. At least one of the strands can include a region that is sufficiently complementary to a target ARN.

A second strand of the agent of dsARN, that includes a region complementary to the antisense strand, is named the "sense strand". Nevertheless, a siARN agent can also be formed based on a single molecule of ARN that is at least partially auto-complementary, forming, for example, a fork or eyelet structure that includes a duplex region. In the future, the latter are named short fork ARN or shARNs. In this case, the term "strand" refers to one of the regions of the molecule of ARN that is complementary to another region of the same molecule of ARN.

The term "post-transcriptional regulating region" as used here, refers to any polynucleotide that facilitates the expression, stabilization or localization of the sequences contained in the cassette or the resulting gene product.

The term "recombinant viral genome", as used here, refers to a genome of AAV in which at least one polynucleotide cassette is inserted unrelated to the expression in the genome of native AAV.

The term "gene rep" or "gene rep of AAV", as used here, refers to a gene that codifies a Rep protein. The term "Rep protein", as used here, refers to a polypeptide that has at least one functional activity of a native rep protein of AAV (for example, Rep 40, 52, 68, 78). A "functional activity" of a Rep protein (for example, Rep 40, 52, 68, 78) is any activity associated to the physiological function of the protein, including the facilitating of the replication of the DNA through the recognition, linking and cutting of the origin of the replication of the DNA of AAV, as well as the DNA helicase activity. The additional functions include the modulation of the transcription of AAV (or other heterologous) promotors and the site-specific integration of the DNA of AAV in a chromosome of the host.

The term "subject" as used here, refers to an individual, plant, mammal or animal, such as a human, a nonhuman primate (for example, chimpanzee or other ape and species of monkeys), an animal (for example, birds, fish, cattle, sheep, pigs, goats and horses), a mammal (for example, dogs and cats), or a laboratory animal (for example, rodents, such as mice, rats, mice with silenced genes (knockout mice), mice that overexpress a gene (transgenic mice) and Guinea pigs). The term does not denote a particular age or sex. The term "subject" includes an embryo and a fetus.

The term "administrated systemically" and "systemic administration", as used in this document, means that the polynucleotides, vectors, polypeptides or pharmaceutical compositions of this invention are administrated to a subject in a non-localized manner. The systemic administration of the polynucleotides, vectors, polypeptides or pharmaceutical compositions of the invention can reach various organs or tissues of the subject's entire body, or can reach new specific organs or tissues of the subject. For example, the intravenous administration of a pharmaceutical composition of the invention could give rise to transduction in more than one tissue or organ in a subject.

The term "regulatory transcriptional region", as used here, refers to a fragment of nucleic acid capable of regulating the expression of one or more genes. The regulating regions of the polynucleotides of the invention include a promotor and optionally, an enhancer.

The term "transduction", as used here, refers to the process whereby a sequence of foreign nucleotides is introduced within the cell in a viral vector.

The term "transfection", as used in this document, refers to the introduction of DNA in the eukaryotic target cells.

The term "vector", as used here, refers to a construct capable of delivering, and optionally express, one or more polynucleotides of interest in a host cell. The examples of vectors include, but are not limited to viral vectors, DNA or nude ARN expression vectors, cosmid or phage vectors, ARN or DNA expression vectors associated with agents of cationic condensation, vectors of DNA or ARN expression vectors encapsulated in liposomes, and certain eukaryote cells, such as producing cells. The vectors can be stable and can be self-replicating. There are no limitations regarding the type of vector that can be used. The vector can be a cloning vector, adequate for the propagation and for the obtaining of polynucleotides, gene constructions or expression vectors incorporated into various heterologous organisms. The adequate vectors include prokaryote expression vectors, phage and shuttle vectors and eukaryote expression vectors based on viral vectors (for example, adenovirus, adeno-associated virus like the retrovirus and lentivirus), such as non-viral vectors such as pSilencer 4,1-CMV.

The term "BDNF", as used here, is a neurotrophin that regulates cerebral development, neuroplasticity and synaptogenesis in the CNS (2).

The term "Regulators of the expression of BDNF" also includes the members of the ATF/CREB family that join the CRE sequences, in addition to the one described in this patent called UPRE's (response elements to badly folded proteins).

The methods and compositions of the invention, for example, the methods and compositions of the AAV virus with the insert XBP1s-HA, can be used with any dosage and/or formulation described in this invention, as well as with any administration route described in this invention.

The "siARN agents or siARN" are a term used to describe duplex fragments of ARN from among 15 and 25 base pairs, preferably 19 to 21 base pairs in length.

For the term "optimization and improvement of the memory, cognitive capacities and learning", we refer to the cognitive tests carried out on different species and/or subjects as defined in this invention.

The term "cDNA" or "complementary DNA" refers to a DNA sequence that is totally complementary to a ARN, from which it is synthetized by RT-PCR.

The words "silencing of a target gene" refers to the process whereby a cell that contains and/or expresses a specific product of the target gene when it is not in contact with the agent, will contain and/or express, at least 10%, 20%, 30%, 40%, 50%, 60%, 70%, 80%, 90% or less of that product of the gene when it comes into contact with the agent, in comparison with a similar cell that has not been in contact with the agent. That product of the target gene can, for example, be a ARN messenger (mARN), a protein or a regulating element.

The term "complementary", as used in this document, is used to indicate a sufficient degree of complementarity that a stable and specific union takes place between a compound and a molecule of target ARN, the specific union requires a sufficient degree of complementarity to avoid the nonspecific union of the oligomeric compound to non-objective sequences in conditions in which the specific union is desired, that is, in physiological conditions in the case of in vivo tests or therapeutic treatment, or in the case of in vitro tests under conditions in which the tests have been carried out.

Ligands

The characteristics of a virus, including its pharmacological characteristics, can be influenced and made to measure, for example, by the introduction of ligands. Additionally, the pharmacological characteristics of a viral agent can be improved by the incorporation of a ligand in a formulation of the agent and a virus.

The ligands can be joined to a wide variety of entities, for example, ligands that are joined to a viral agent, or they can be used as a conjugate or additive of formulation, for example, with the vehicle of a monomeric subunit conjugated with the ligand. The examples are described later in the context of a monomeric subunit conjugated with ligand but that is only the preferred, and the entities can be attached at other points with a virus.

A ligand alters the distribution, direction or time of life of a viral agent into which it is incorporated. In the preferred modalities, a ligand provides a better affinity for a selected objective, for example, a molecule, cell or type of cell, a compartment, for example, a cellular compartment or organ, a tissue, or region of the body, for example, as compared with a species in which this ligand is absent.

The ligands can improve the characteristics of transport, hybridization and specificity of the target molecule, for this invention, of the virus.

In general, the ligands can include therapeutic modifiers, for example, to improve the absorption of the molecule in the individual; diagnostic compounds or reporter groups, for example, to monitor the distribution; crosslinking agents; fractions that confer resistance to immune reactions; and natural or unusual nucleobases.

The general examples include lipophilic molecules, lipids, lectins (for example, hecogenin, diosgenin), terpens (for example, triterpenes, for example, sarsasapogenin, friedelin, lithocholic acid derived from epifriedelanol), vitamins, carbohydrates (for example, a dextran, pullulan, chitin, chitosan, synthetic polymers (for example, oligo-lactate 15-mer) and natural polymers (for example, of low and medium molecular weight), inulin, cyclodextrin or hyaluronic acid), proteins, protein binding agents, integrin targeting molecules, polycations, peptides, polyamines and mimetics of peptides. Other examples include the ligands that receive epithelial cells or folic acid cells, such as transferrin.

The ligand can be a molecule that is present naturally or recombining or synthetically, such as a synthetic polymer, for example, a synthetic poly-amino acid. The examples of the poly-amino-acids include polylysine (PLL), poly-acid L-aspartic, poly-acid L-glutamic, copolymer of styrene-anhydride of maleic acid, copolymer of poly-(lactic-co-glycolic), copolymer of N-(2-hydroxi-propyl) methacrylamide (HMPA), polyethyleneglicol (PEG), polyvinylvinylic alcohol (PVA), polyurethane, poly-(acid 2-ethyl-acrylic), polymers of N-isopropyl-acryl-amide or polyphosphazine. The examples of the polyamines include: polyethyleneimine, polylysine (PLL), spermine, spermidine, polyamine, pseudo-peptidic polyamine, peptidomimetic, dendrimer polyamine, arginine, amidine, protamine, cationic fractions, for example, cationic lipid, cationic prophyrin, quaternary salt of a polyamine, or an alfa-helicoidal peptide.

The ligands can also include steering groups, for example, a steering agent to a cell or tissue, for example, a thyrotropin, melanotropin, surfactant protein A, mucin carbohydrate a glycosylated polyaminoacid, bisphosphonate, polyglutamate, polyaspartate or a peptide of Arg-Gly-Asp (RGD), or a mimetic of peptide of RGD.

The ligands can be proteins, for example, glycoproteins, lipoproteins, for example, low density lipoprotein (LDL) or albumins, for example, serum albumin, or peptides, for example, molecules that have a specific affinity for a co-ligand, or antibodies, for example, an antibody that links with a type of cell specified. The ligands can also include hormones and hormone receptors. They can also include non-peptidic species such as cofactors, multivalent lactose, multivalent galactose, N-acetyl-galactosamine, N-acetyl-glucosamine, multivalent mannose or multivalent fucose.

The ligand can be a substance, for example, a pharmaceutical product that can increase the absorption of the viral agent in the cell, for example, by altering the cytoskeleton of the cell, for example, by altering microtubules, microfilaments and/or intermediate filaments of the cell.

In one aspect, the ligand is a lipid, or a molecule based on a lipid. This lipid or this molecule based on a lipid, preferably are linked with a serum protein, for example, albumin serum.

In an alternative modality, the viruses will be packed.

For the preparation of the injectable solutions of the virus, they are prepared diluting the necessary concentration of virus in PBS (phosphate buffered saline) that has the following formula

PBS 1×

1. Dissolve the viral dose in 800 ml of distilled water with:
8 g of NaCl
0.2 g of KCl
1.44 g of $Na_2HPO_4$
0.24 g of $KH_2PO_4$ 2. Adjust the pH to 7.4 with HCl.
3. Adjust the volume to 1 L with distilled water additional H$_2$O.
4. Sterilize and autoclave.

Design and Selection

The control of the protein synthesis and the induction of the expression of the gene is the key for the formation and maintaining of long-term memory.

In addition to requiring the modulation of the local synthesis of proteins, the formation of the memory implies other aspects in the secretory route including the synthesis and the traffic of diverse membrane receptors and ionic channels, increase in the calcium signaling, the synthesis of membranes and the assembly of protein complexes. Nevertheless, a singular function of XBP1 specifically in the hippocampus was discovered, independent of the control of the canonical genes associated to the UPR. Using the profit and loss of the function, it was proved that XBP1 is required for the optimum establishment of the long-term memory. This unexpected function could have an evolutive origin as XBP1 is a member of the superfamily of CREB. This transcription factor is known because of its importance in the storing of long-term memory. The application example, described here, provided the test that XBP1 modulates the expression of a group of genes with proven activity in learning and memory.

Analyzing the biomedical scope of the utilization as a therapy, an effective and innovative method was provided to improve the memory and learning, in which the use of this technology generates surprising results in its application.

To explore the participation of XBP1, specifically XBP1s in the cognitive, sensorial or motor functions of the CNS, a revision was made of the behavior in animals of neuron-specific knockout XBP1 (XBP1$^{Nes-/-}$) and no spontaneous motor abnormality was observed, obvious or of behavior in these animals nor were histological alterations detected in the brain of these animals. Nevertheless, the mutant animals showed a specific deterioration in the contextual fear conditioning test (FIG. 5/17).

On the other hand, the production of mARN was evaluated for a group of genes associated to memory and learning processes; it was determined that the genes Kif17, Ampa3 and Bdnf decrease in the deficiency of XBP1 (Table 1), in the hippocampus and not in the amygdala, brain regions involved in this task (FIGS. 1/17 and 2/17 respectively).

The learning capacity of the animals XBP1$^{Nes-/-}$ was also measured using the paradigm of the flexibility of the memory, a test depending on the hippocampus related with the episodic memory. The XBP1$^{Nes-/-}$ animals require more tests than the control animals to execute the task over time, which indicates a significant deterioration of the memory (FIG. 6/17). This phenotype was produced in absence of alterations in the memory of the cortex-dependent brain, in motor skills, in anxiety or in reflex control, according to the evaluation of these animals on the hot plate, in the recognition of new objects test, the rotarod and in the startle response test. For a more in-depth exploration of the effects of XBP1 on the synaptic plasticity and the memory, the glutamatergic transmission evoked by the stimulation of the collateral of Schaffer in hippocampal slices was measured and the field excitatory postsynaptic potential (fEPSP) was recorded in the CA1 region to evaluate the long-term potentiation (LTP) with a high frequency stimulation. The deficiency of XBP1 in the CNS reduces the induction and maintenance of the LTP evaluated by the amplitude of the fEPSP over time (FIG. 7/17).

In the ER stress response, XBP1 has been indicated as an important component of secretory cells, as it regulates transcriptionally a group of genes related to the folding and quality control of proteins (13, 14). To identify the effects of the deficiency of XBP1 on the genic expression in the hippocampus of animals, these were sacrificed after the training to the conditioning to the contextual fear and the levels of mARN of XBP1-dependent genes were evaluated (for example: Wfs1 and Edem1) and XBP1-independent genes (Bip gene). Surprisingly, no changes were observed in the expression of genes related to the UPR in the hippocampus of XBP1$^{Nes-/-}$ animals in comparison with control animals (XBP1$^{f/f}$) (FIG. 4/17)). Based on the cognitive defects identified in XBP1$^{Nes-/-}$ animals, the expression of a group of known genes related with learning and memory (Table I) was evaluated.

TABLE I

| | | XBP1$^{Nes-/-}$ v/s XBP1$^{WT}$ | |
|---|---|---|---|
| | Gene Name | Fold change | P-value |
| ttr | transthyretin | 0.81 | 0.74 |
| reln | reelin | 0.68 | 0.30 |
| gria1 | glutamate receptor, ionotropic, AMPA1 (alpha 1) | 0.75 | 0.22 |
| gria2 | glutamate receptor, ionotropic, AMPA2 (alpha 2) | 0.77 | 0.03 |
| gria3 | glutamate receptor, ionotropic, AMPA3 (alpha3) | 0.58 | <0.01 |
| gria4 | glutamate receptor, ionotropic, AMPA4 (alpha4) | 0.93 | 0.64 |
| myo5b | myosin VB | 0.44 | 0.07 |
| creb | cAMP responsive element binding protein | 0.98 | 0.94 |
| bdnf * | Brain derived neurotrophic factor | 0.19 | 0.01 |
| camkII | Calcium/calmodulin-dependent protein kinase II | 1.30 | 0.48 |
| ryr1 | ryanodine receptor 1 | 0.93 | 0.86 |
| ryr2 | ryanodine receptor 2 | 0.68 | 0.06 |
| ryr3 | ryanodine receptor 3 | 0.61 | 0.02 |
| nr2a | ionotropic glutamate receptor subunit NR2A | 1.00 | 0.56 |
| nr2b | ionotropic glutamate receptor subunit NR2B | 1.21 | 0.16 |
| pp2b/caln | calcineurin | 1.09 | 0.69 |
| kif17 * | Kinesin family 17 | 0.73 | 0.01 |
| stx17 | syntaxin 17 | 0.76 | 0.09 |
| kcnk1 | potassium channel, subfamily K, member 1 | 0.76 | 0.20 |
| xpo4 | exportin 4 | 0.93 | 0.76 |
| csnk2a | casein kinase 2, alpha 1 polypeptide | 1.01 | 0.97 |
| adrb1 | adrenergic receptor, beta 1 | 1.14 | 0.39 |
| pten | phosphatase and tensin homolog | 1.32 | 0.45 |

TABLE I-continued

| | | XBP1$^{Nes-/-}$ v/s XBP1$^{WT}$ | |
| Gene Name | | Fold change | P-value |
|---|---|---|---|
| map2k3 | mitogen-activated protein kinase kinase 3 | 1.14 | 0.30 |
| uqcr10 | ubiquinol-cytochrome c reductase, complex III subunitX | 1.94 | 0.22 |
| nipsnap1 | 4-nitrophenylphosphatase domain and non-neuronal SNAP25-like protein homolog 1 | 1.35 | 0.50 |

This table I shows the profile of the gene expression in the hippocampus of XBP1$^{Nes-/-}$ animals in comparison with animal control. The levels of mARN of genes associated to learning and memory processes are shown, evaluated in dissections of hippocampus as of male mice using PCR in real time (XBP1$^{Nes-/-}$ n=4, XBP1$^{f/f}$ n=5 to 6), the average and the standard error are indicated and the statistic Student's t-test was carried out to obtain the value of p. The genes that present a significant value of p are represented with darker letters.

The deficiency of XBP1 has led to notable reductions in the levels of mRNA of a subset of genes (FIG. 1/17). These alterations in the gene expression were specific for the hippocampus as they were not detected in the dissected amygdala of the same XBP1$^{Nes-/-}$ animals (FIG. 3/17).

To prove whether the increase of XBP1s in the SNC alters the learning and memory capacity of animals, a transgenic mouse model was generated that overexpresses the active form of XBP1s in neurons that the prion promotor uses to conduct their expression (Tg$^{XBP1s}$). These animals are viable, they are born according to the Mendelian coefficients and do not develop any visible phenotype. The restricted expression of the transgene in the CNS was confirmed by Western blot and analysis of PCR in real time (FIG. 8/17, left panel). Notably, the expression sustained of XBP1s in the CNS improves the performance of the animals in the memory flexibility tests (FIG. 8/17, right panel). According to these results, the slices of hippocampus derived from Tg$^{XBP1s}$ animals showed a sustained and superior amplitude of the LTP induced by theta-burst stimulation (FIG. 9/17), in comparison with control animals of the same litter.

After seeing the effect of the manipulation of XBP1s in transgenic mice and investigating the specific function in the hippocampus, an adeno-associated (AAV) virus was developed capable of introducing the XBP1 gene in different individuals.

With regard to the development of the adeno-associated virus (AAV), it includes the viral recombinant genome that consists of an expression cassette that includes a transcriptional regulatory region specific hippocampal tissue operatively linked to the polynucleotide of interest. According to this invention, the adeno-associated virus (AAV) includes any known serotype of the 42 types and are derived from the parvovirus. In general, the different serotypes of AAV are genomic sequences with a significant homology at amino acid and nucleic acid level, that provide identical genetic functions, provide vibrios that are essentially identical in functional and physical terms, and their replication, assembly uses practically the same mechanisms.

In this particular invention serotype 6 AAV was used (just as those mentioned, for example, in GenBank access number AF028704.1 (AAV 6), NC006260 (AAV7), NC006261 (AAV8) and AX753250.1 (AAV9)), as presented in Table II.

The genome of the AAV, according to this invention, normally includes an actuator in cis 5' and an inverted terminal repetition sequence in 3' and an expression cassette.

The ITR or LTR sequences have 141 pairs long. Preferably, the complete sequence of the LTRs is used in the molecule and only slight modification of the sequences are allowed. In a preferred form of this invention, the recombinant genome of the AAV comprises the 5' and 3' AAV LTRs. In another preferred form of this invention, the 5' and 3' AAV LTRs derives from the serotype 6 AAV. In another more preferred form of this invention, the recombinant genome of the AAV lack the Rep and Cap open reading frame.

On the other hand, the ITRs can originate from other serotypes of AAV.

The AAV of this invention comprises a capsid from any serotype. In particular, for this invention, the capsid derived from serotypes 6, 7, 8 and 9 is preferred. Although, preferably, the capsid of the AAV of serotype 6 is desired.

In some realizations, a cap of the AAV for use in the method of the invention can be generated by mutagenesis (that is, insertions, deletions or substitutions) of one of the AAV caps or of its codifying nucleic acids. In some realizations, the cap of AAV is at least 70%, 75%, 80%, 85%, 90%, 95%, 98% or 99% or more similar to one or more of the mentioned AAV caps.

In some realizations, the AAV cap is chimerical, includes the dominions of two, three, four or more of the mentioned AAV caps. In some realizations, the cap of the AAV is a mosaic of the monomers VP1, VP2, VP3 and proceeding from two or three different AAV or a recombinant AAV (rAAV). In some realizations, a composition of rAAV includes more than one of the mentioned CAPS.

In some realizations, a CAP AAV for its used in a composition of rAAV is designed to contain a heterologous sequence or other modification. For example, a peptide or protein sequence that confers selective focalization or the immune evasion can be by genetic engineering in a Cap protein. Alternatively, or furthermore, the Cap can be modified chemically so that the surface of the rAAV presents specific chemical modifications, for example, polyethylene glycol, which can facilitate immune evasion. The Cap protein can also be generated mutagenized (for example, to eliminate its natural binding receptor or to mask an immunogenic epitope.

In a realization, the vector of AAV contains a promotor with the addition of at least one target sequence of at least one sequence of XBP1 that can be selected in the following tables: Table IV (Xbp1s) and Table V (Xbp1u) (NCB1 reference sequence NM_001271730.1 and NM_013842.3 respectively).

The references of sequences were obtained from ncbi.nlm.nih.gov/nucleotide/
4111474450?report=genbank&log$=
nucltop&blast_rank=1&RID=7TM54X2201R (Xbp1s) and
ncbi.nlm.nih.gov/nucleotide/
411147449?report=genbank&log$=nucltop&blast_
rank=2&RID=7TM54X2201R (Xbp1u).

In a realization, the vector of AAV contains a promotor with the addition of at least one target sequence of Xbp1s that can be selected from table IV, remaining as presented in Table III.

In a realization, the vector of AAV contains a promotor with the addition of at least one target sequence of Xbp1u that can be selected in table V.

In a realization, the vector AAV contains a promotor with the addition of at least one target sequence that has a homology of 85% with a target sequence selected from the list mentioned previously, table IV and table V.

In a realization, the vector AAV contains a promotor with the addition of at least a second target sequence that has a homology of 70% with a target sequence selected from the tables mentioned previously.

In a realization, the vector AAV contains a promotor with the addition of at least one target sequence that is a functional equivalent with a target sequence selected from the tables mentioned.

The regulating region of the transcription can include a promotor and, optionally, an enhancer region. Preferably, the promotor is selected from this listing: PGK1, CAMKII, THY1, among others. The enhancer does not need to be specific for the neuronal tissue.

In a realization, the promotor is specific, for example, that of the protein phosphoglycerate kinase 1, also known as PGK1.

In a realization, the promotor is specific, for example, that of the Calcium calmodulin kinase 2, also known as CAM-KII.

In a realization, the promotor is specific, for example, also known as Thy1.

In another realization, the expression cassette that forms part of the AAV of the invention also includes a post-transcriptional regulatory element. In a preferred realization, the post-transcriptional regulatory element is the woodchuck hepatitis virus posttranscriptional regulatory element (WPRE) or functional variants and fragments of the same and the PPT-CTS or functional variants and fragments of the same. In a particular realization, the post-transcriptional regulatory element is WPRE.

The expression cassette that forms part of the AAV according to the invention comprises a "polynucleotide of interest". In a preferred realization, the polynucleotide of interest codifies a protein that acts systemically. In another realization, the polynucleotide of interest codifies a protein that acts within a neuron. In a preferred realization, the protein that acts within said neuron is XBP1s, including any of its isoenzymes that vary in subcellular localizations.

The size limit of the containers of the vector AAV is limited to the size of the wild-type genome AAV, that varies in size according to the serotype of AAV (that is, between 4087 and 4767). For example, native AAV-6 has a genome size of 4683. In some forms of realization, the ability to clone of the recombinant ARN vector can be limited and a desired codification sequence can imply the complete substitution of 4.8 kilobases the genome of the virus. Therefore, large size genes may not be adequate for use in a standard vector of recombinant AAV, in some cases. The average expert will appreciate that the options are available in the state of the art for overcoming a limited codification capacity. For example, the AAV IRT of two genomes can hybridize to form head to tail concatemers, nearly duplicating the capacity of the vector. The insertion of the splice sites permits the removal of the IRT after the transcription. Other options for overcoming a limited capacity to clone will be evident to the expert in the subject.

Routes of Administration

The routes of administration of the virus are conditional upon the virus being able to pass the haemato-encephalic barrier to infect the target neurons.

To achieve this purpose in this invention, two main routes of administration have been defined.

The first of these routes is the nasal (18). Generally, the medications administered by the nose can enter the blood through the general circulation, can penetrate the brain directly or, in some cases, can follow both routes. Nevertheless, many of the factors that control the flow of the drug through each one of these routes are not defined completely. In general, there are three routes through which a drug administered in the nasal cavity can travel. These routes (18) include the entrance in the systemic circulation directly from the nasal mucosa (19), the entrance in the olfactory bulb by the axonal transport through the neurons, and the direct entry in the brain (20). The evidence that supports the role of each one of these routes for a variety of model substrata is summarized below for different types of viruses.

Transport routes followed by various viral solutes through nasal administration

| Virus | Animal model | Means of Administration | Route followed |
|---|---|---|---|
| Hepatitis virus | Mice | Innoculation Nasal | Olfatory nerve |
| Herpes virus Simplex | Mice | Nasal drops | Direct, Systemic, Olfatory nerve |
| Encefalitis virus | Mice | Innoculation Nasal | Olfatory nerve |
| Neumococos | Mice | Nasal drops | Direct |

The nature of this table is not intended to be exhaustive but rather to highlight some of the solutes of different classes that have followed one or more routes.

Other means of administration to the cells in the CNS have included (19):

The direct injection in fluid spaces, such as the vitreous humor in the eye; or in the brain fluid of the spinal column through different routes, intraventricular or intrathecal (**) for its delivery to the choroid plexus, the ependymal/meningeal layers, and from there in the adjacent brain through processes that extend within these layers; and its passage through the blood-brain barrier or blood-tumor barriers by means of intra-arterial injection combined with an osmotic or temporary pharmacological interruption.

The term (**) Intrathecal (intra+theca, "within a pod") is an adjective that refers to something that occurs or is introduced in an anatomic space or potential space within a sheath, more commonly the arachnoids membrane of the brain or the spinal cord.

Calculation of Dose

According to Ulusoy et al (20), the titration of the vector requires a range between $10^9$ to $10^{13}$ copies of genome (CG) per ml with a tested dose between $10^{10}$-$10^{12}$ gc/ml. On the other hand, any dilution rate of the vectors to titre must have a low-medium range of $10^{11}$ gc/ml, which results in the disappearance of the toxicity.

Dose in Humans:

The dose range in humans lies in the range between $10^9$ to $10^{30}$ viral units/kilo of weight, without restricting this range to the application in different age groups or with distribution volumes modified by age or pathology.

The maximum concentration or level of a substance found experimentally or by observation, that does not cause detectable adverse alterations in the morphology, functional capacity, growth, development or duration of the life of the target organisms, distinguishable from those observed in normal organisms (control) of the same species and strain, under defined conditions of exposure.

Method of Application

The rAAV6 vectors were injected bilaterally in the SN using a 50 Hamilton syringe equipped with a glass capillary with a diameter at the point of about 60-80 microns. Two microliters of buffer that contain the appropriate concentrations of viral particles were injected at a speed of 0.4 μl/minute. The needle is withdrawn slowly 5 minutes after the finalization of the injection.

In this figure, an evaluation is made of the levels of expression of several genes related with the memory measured in the hippocampus, such as XBP1$^{f/f}$ (n=4 mice) and XBP1$^{Nes-/-}$ (n=5 to 6 mice) using PCR in real time.

FIG. 2/17

Figure 1:
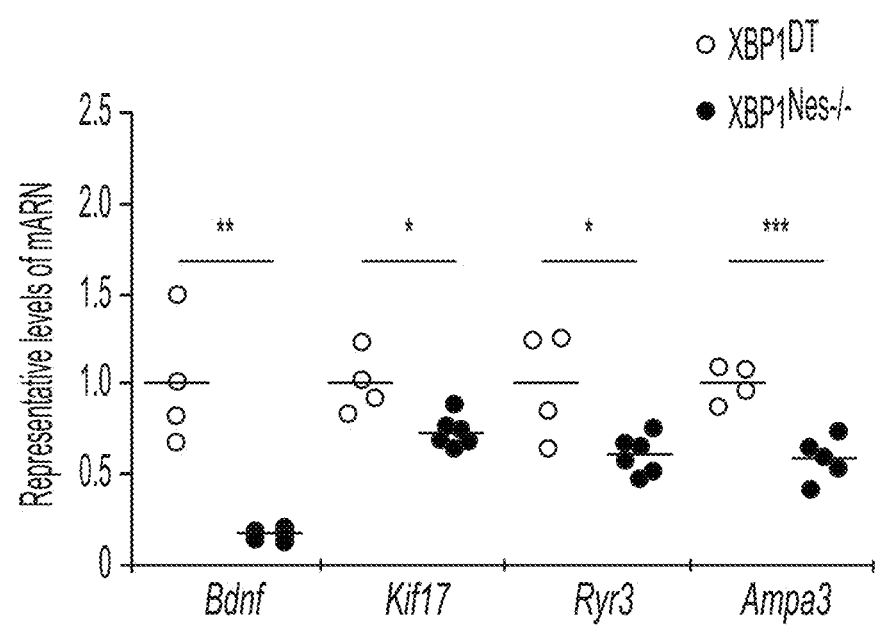
FIG. 1/17
Figure 2:
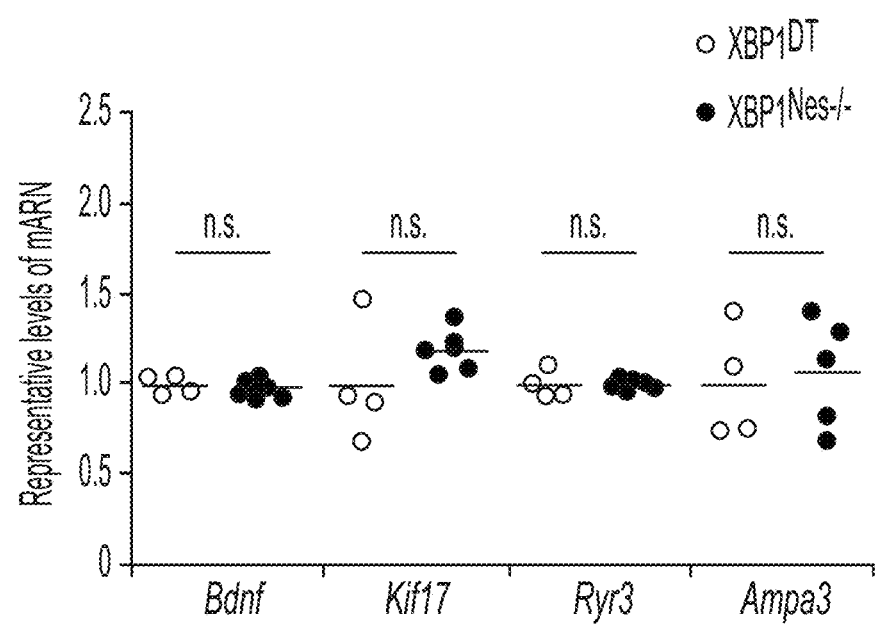
Figure 3:
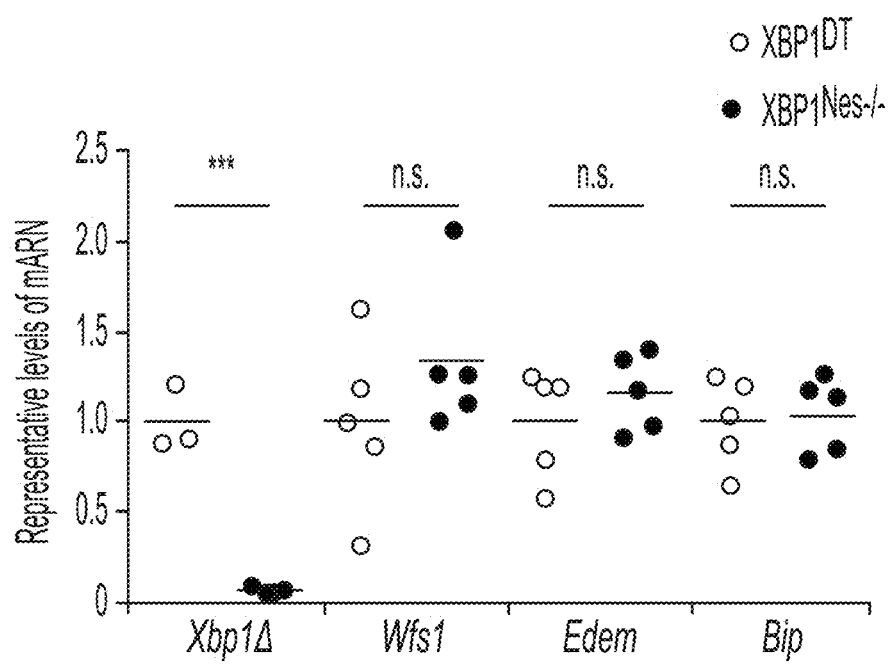
Figure 4:
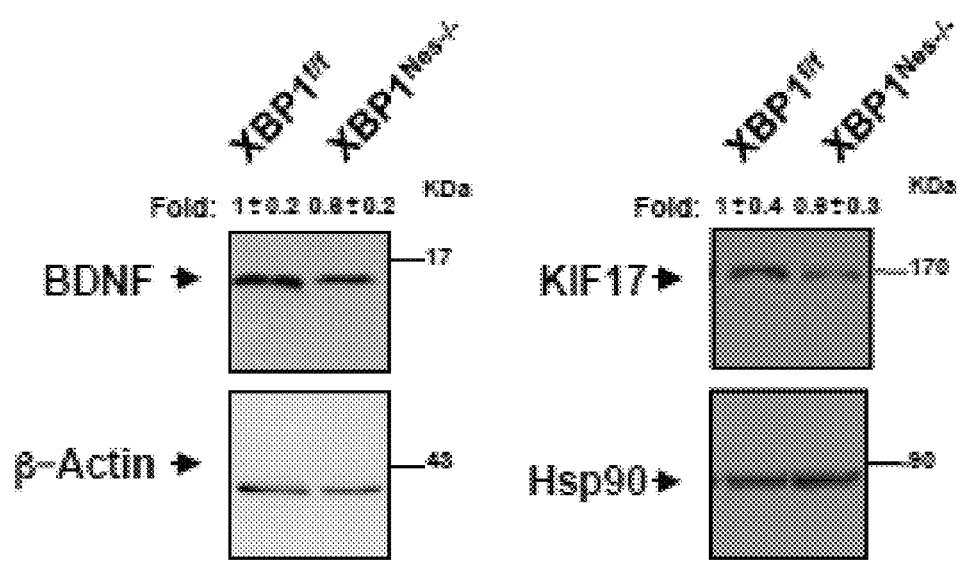
Figure 5:
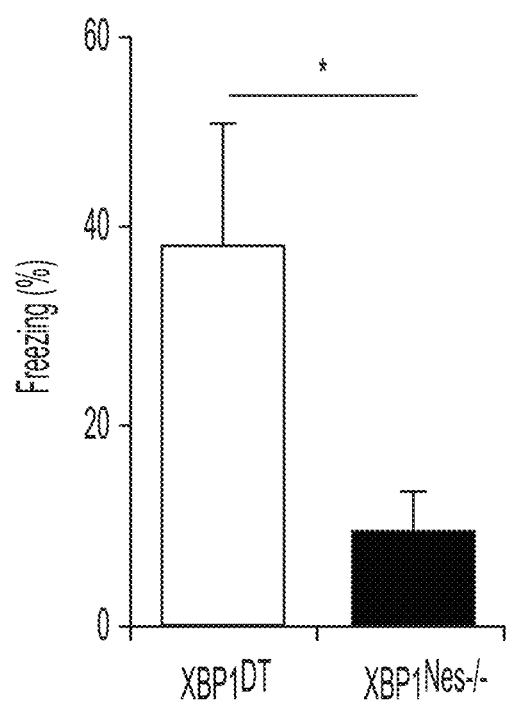
Figure 6:
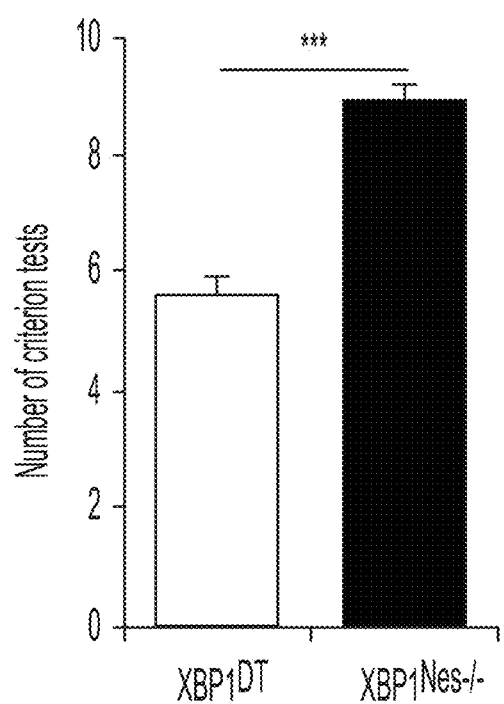
Figure 7:
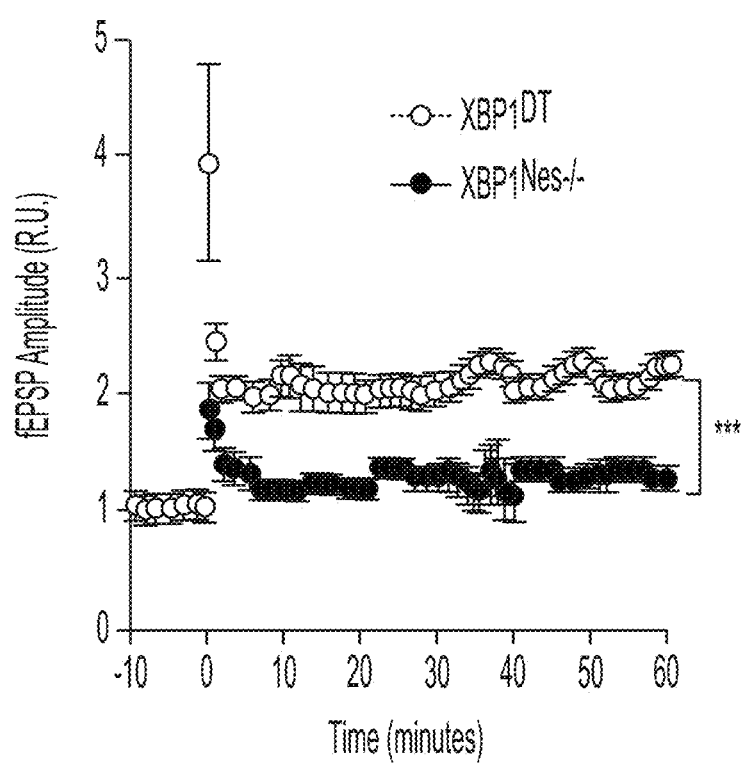
Figure 8:
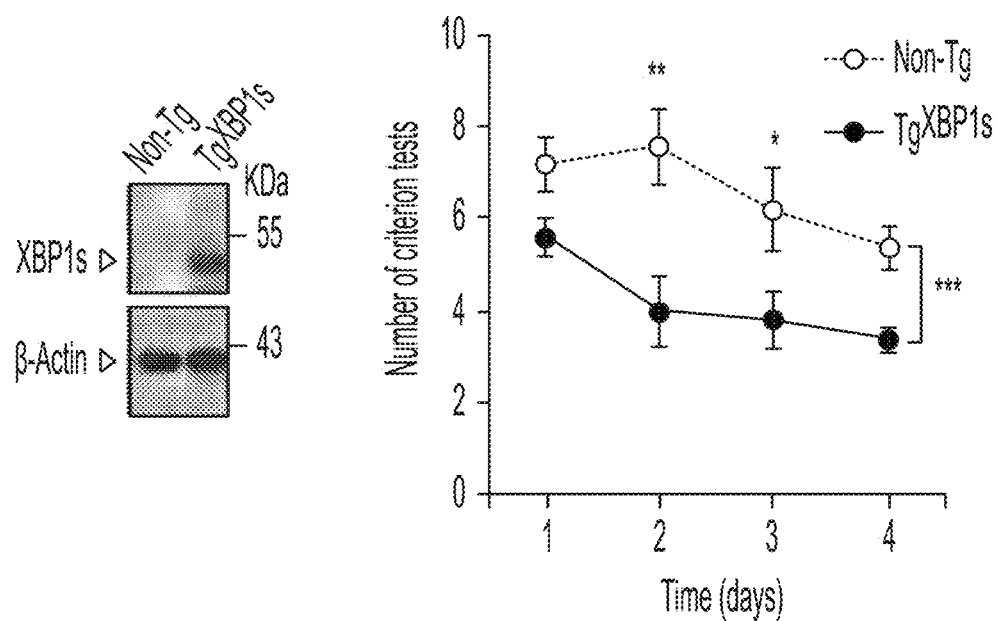
Figure 9:
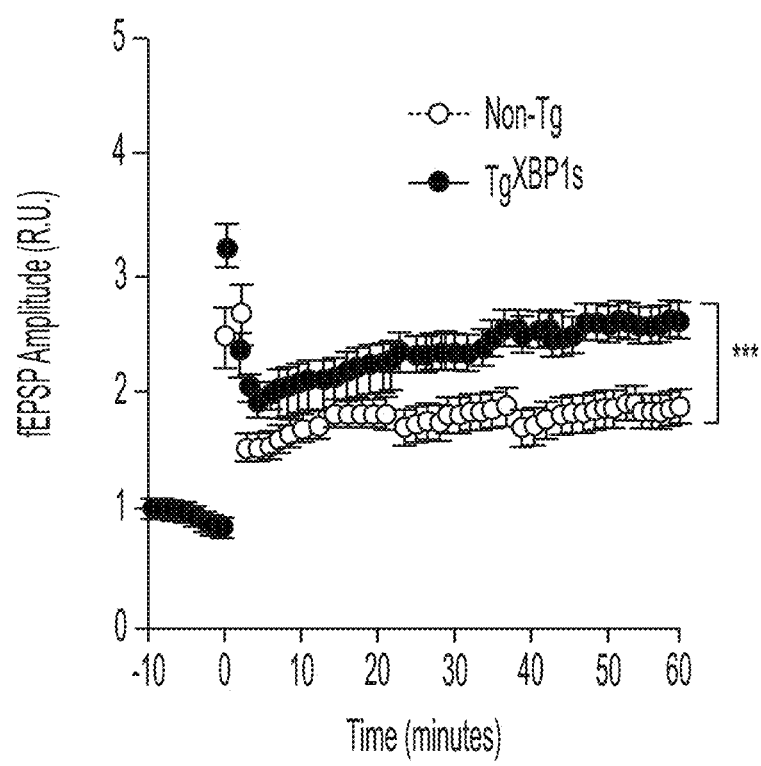

This figure presents the levels of mRNA of the genes related with the memory, indicated in FIG. 3/17, measured in the amygdala using PCR in real time. In c, d and f the averages are shown and a statistical analysis was carried out using Student's t-test (*: $p<0.05$, : $p<0.01$, * $p<0.001$, ns: not significant). All the samples were standardized with the levels of β-actin.

FIG. 3/17

This figure presents the levels of BDNF and KIF17 protein that were analyzed by Western blot using extracts of hippocampus obtained from 6-month old animals for XBP1$^{f/f}$ and XBP1$^{Nes-/-}$. The levels of β-actin or Hsp90 were used as load control. The average and the standard error are shown as the times of change in comparison with control animals (n=3). The bands were spliced from the same gel and their exposure to the film.

FIG. 4/17

This figure shows the levels of mRNA of the genes of the UPR indicated. These genes were measured in the dissected hippocampus of mice XBP1$^{Nes-/-}$ or of animals XBP1$^{f/f}$ using PCR in real time. The analysis was executed at 6 months of age (n=3 per group for Xbp1Δ and n=5 per group for Wfs1, Edem and Bip).

FIG. 5/17

This figure shows the alterations in the long-term memory and the long-term potentiation of XBP1 conditioned in knock-out mice. Here we see a bar graph where the XBP1$^{Nes-/-}$ mice are presented and the control of the same litter (XBP1$^{f/f}$) of male mice where conditioning to contextual fear was tested in the test. The percentage of events of immobility during the test was calculated (XBP1$^{f/f}$: n=4 and XBP1$^{Nes-/-}$: n=6 per group). A statistical analysis was made using the Student's t-test (*: $p<0.05$).

FIG. 6/17

Presented here in parallel, in another bar graph, is the result obtained when the animals were trained and evaluated using the paradigm of memory flexibility. The analysis shows the average number of tests to find the criteria of four consecutive days (n=4 per group). A statistical analysis was carried out using the Student's t-test (***: $P<0.001$).

FIG. 7/17

This figure presents the electrophysiological records of the LTP carried out on hippocampal slices derived from XBP1$^{Nes-/-}$ or XBP1$^{f/f}$ of the same litter of control mice (n=7 per group). Representative records of the fEPSP are shown after three stimulation trains with 100 Hz in the collateral circuit of Schaffer-CA1. The statistical analysis was carried out using two-way ANOVA (***: $p<0.001$).

FIG. 8/17

This figure shows that the overexpression of XBP1s in the neurons improves the long-term memory. In this figure, a specific neuronal transgenic strain of XBP1s is presented, created using the promotor of the prion to induce the expression in the CNS (Tg$^{XBP1s}$). In the left panel, we observe the levels of XBP1s in hippocampus analyzed by Western blot with the levels of β-actin as load monitor. In the right panel, the level of learning was evaluated comparing animals Tg$^{XBP1s}$ and the control litter, using the memory flexibility test. The number of tests to reach this criterion is presented (n=5 per group). The statistical analysis was carried out using a two-way ANOVA, followed by a Bonferroni post-test (*: $p<0.05$,  $p<0.01$, * $p<0.001$).

FIG. 9/17

The LTP was measured in hippocampus slices Tg$^{XBP1s}$ and in control animals by theta burst stimulation (n=7 per group). The records of the fEPSP are shown. A statistical analysis was made using a two-way ANOVA (***: $p<0.001$).

FIG. 10/17

This figure shows that the local expression of XBP1s in the hippocampus improves the long-term memory tests in three-month old mice that were injected with an adeno-associated virus (AAV) serotype 6 to deliver XBP1s-HA (AAV/XBP1s-HA) or the empty vector (AAV/MOCK) in the hippocampus using bilateral stereotaxis. Fourteen days after the injection, the animals were trained and evaluated in the memory flexibility test (n=6 per group). The statistical analysis was carried out via a two-way ANOVA followed by a Bonferroni post-test (*: $p<0.05$, : $p<0.01$, *: $p<0.001$).

FIG. 11/17

In this diagram, Xbp1s is presented in the left panel and Bdnf in the right panel. The mARN levels were measured by PCR in real time in the total of cADN obtained as of the hippocampus of wild-type mice injected with AAV/XBP1s or AAV/MOCK particles. The expression values were standardized with the levels of β-actin (n=6 per group). A statistical analysis was made using the Student's t-test (*: $p<0.05$).

FIG. 12/17

Figure 10:
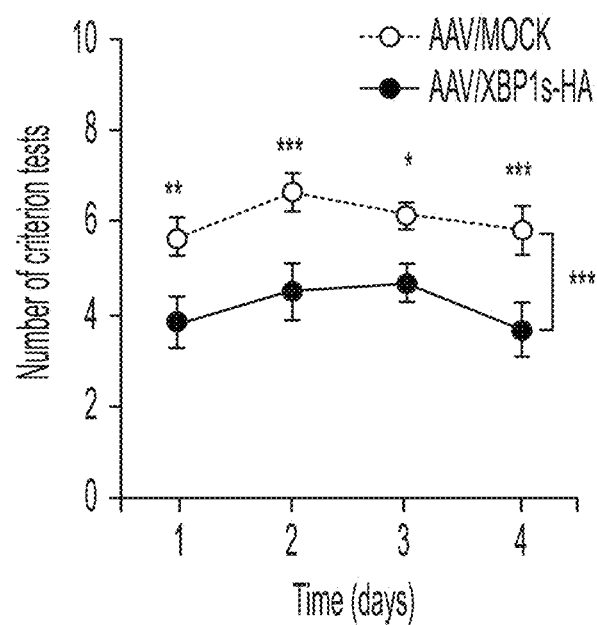

In these graphs, mice were evaluated that had been injected with particles of AAV, described in FIG. 10/17, in the hippocampus by means of two different virus titles (1×:1×10$^6$ Tus, 10×: 1×10$^7$ TUS) by means of bilateral cerebral stereotaxis. In the left panel, images representative of the immunohistochemistry of injected animals can be seen, where they are shown after the tincture with the anti-HA antibody where the arrowheads indicate the HA-positive neurons. The scale of the bar: 100 μm.

In the right-hand panel, the mice were trained for the oasis labyrinth test and the percentage of success in the task was measured over time (1× title: AAV/MOCK n=9; AAV/XBP1s-HA: n=10; 10× title: AAV/MOCK n=5; AAV/XBP1s-HA: n=5). A statistical analysis was carried out by means of a two-way ANOVA followed by a Bonferroni post-test (*: $p<0.05$, ***: $p<0.001$). The average and the standard error are presented in all the figures.

FIG. 13/17

This figure presents that the overexpression of XBP1s in the hippocampus of mice improves the performance in the Oasis test. The mice were injected by bilateral stereotaxis with the serotype 6 of the adeno-associated virus (AAV) to deliver XBP1s-HA (AAV/XBP1s-HA) or particles of an empty vector (AAV/MOCK) in the hippocampus of wild-type mice using the different titres of virus (1×: 1×10$^6$ TUs, 10×: 1×10⁷ TUs). The mice were trained in the oasis labyrinth (FIG. 12/17, right-hand panel), and in the test the ratio of distances was measured (observed versus expected). The average and the standard error were presented in the figure. The statistical analysis was carried out using a two-way ANOVA followed by a Bonferroni post-test (*: $p<0.05$, **: $p<0.01$).

FIG. 14/17

This figure presents a work model where one sees an interaction between the virus AAV/XBP1s-HA and/or the AAV/XBP1u-HA virus and a cell from the hippocampus and how the mARN of Xbp1s and Xbp1u act on the group of genes (Ryr2, Ampa 3, Bdnf and Kif17) in the regulating of learning and the memory. Where the expression of XBP1 in the neurons of the hippocampus directly or indirectly (dotted lines) controls the expression of different genes implied in the establishment of the memory and other cognitive processes. The direct regulation of the genes of the cluster and the expression that is produced through the bonding of XBP1 to a bonding site UPRE B located in the proximal promoter region of Bdnf.

FIG. 15/17

This figure shows an outline of the AAV genome.

REP: Genes involved in the AAV replication mechanism.

VP: Genes involved in the formation and assembly of the capsid.

ITR: It is the equivalent of LTR, repeated terminal inverted sequence.

FIG. 16/17

This figure presents the vector of the AAV virus with the insert Xbp1s with the following specific description according to table VI.

c) sense strand d) HA—antisense strand

17B) In the lower figure, the expression levels of HA were evaluated based on total extracts of proteins from HEK cells after 48 hours of transfection with the different constructs. The extracts of proteins were made in RIPA solution and 35 mg of proteins were analyzed using Western Blot in gels of acrylamide at 8%. The expression of HA was determined using a monoclonal primary antibody destined against HA (Dilution 1:1000, Covance, catalogue number MMS-101R) and the secondary antibody anti IgG of mice conjugated to peroxidase (dilution 1:3000). As load control, the expression of β-Actin was determined using a primary polyclonal antibody (dilution 1:1000, Santa Cruz, catalogue number sc-1616) and the secondary antibody anti-IgG of goat conjugated to peroxidase (dilution 1:3000).

EXAMPLE OF APPLICATION

Experimental Test 1

The transformed virus AAV/XBP1s-HA was applied locally in brains of wild mice to increase the expression of XBP1s and its activity. The selective expression in the hippocampus of adult mice was induced by bilateral stereotaxic injections of the AAV virus serotype 6 in order to free XBP1s and, on the other hand, a control vector AVV/MOCK, in the area of the hippocampal region CA1.

Two weeks after the injection, the rats were tested in memory flexibility tests. Results were observed similar to those observed in the Tg$^{XBP1s}$ animals, with the local expression of XBP1s in the hippocampus, resulting with an improved performance in the cognitive tasks (FIG. 10/17).

TABLE VI

| Type | Start | Stop | C Description |
|---|---|---|---|
| LTR | 1 | 141 | /note = L-ITR |
| promoter | 150 | >706 | /note = PGK1 promoter |
| frag | 151 | 708 | /note = 151 to 708 of #18 AAV-PGK1-MCS |
| intron | 721 | 1203 | /note = beta-globin intron |
| CDS | 1219 | 1248 | /note = /HA tag= |
| CDS | 1249 | 2364 | /note = /xbp-1= |
| frag | <2368 | 2970 | /note = 1 to 605 of WPRE |
| frag | <2378 | >2967 | /note = WPRE |
| frag | 2380 | >2967 | /note = 1094 to 1682 of WHV |
| frag | 2380 | >2967 | /note = 1 to 589 of WHV lentivirus |
| CDS | 2789 | >2967 | /codon_start = 1<br>/db_xref = PID: g336148<br>/note = X protein<br>/translation = MAARLCCHLDSARDVLLLRPFGPQSSGPSFPRPAAGSAASSASSPSPSDESDLPLGRLPACFASASGPCCLVFTCADLRTMDSTVNFVSWHANRQLGMPSKDLWTPYIKDQLLTKWEEGSIDPRLSIFVLGGCRHKCMRLL[Split] |
| polyA_site | 2976 | 3454 | /note = hGH polyA |
| LTR | 3494 | 3634 | /note = R-ITR |
| insertion_seq | 3726 | 4032 | /note = f1 origin |
| CDS | 4551 | 5408 | /note = Ampicillin resistance ORF |
| insertion_seq | 5559 | 6226 | /note = pUC origin |

FIG. 17A and 17B

This figure presents the generation of the adenoviral plasmid (pAAV) for XBP1s.

(17A) Description of the splitters used in the cloning of XBP1s with HA tag in the expression vector pAAV-PGK1-MCS. Splitters were designed that delimit the murine XBP1s sequence: the sense strand includes the sequence of the HA tag for the 5' end (left panel) and the antisense strand includes the sequence of the HA tag for the 3' end (right panel) indicated by the gray-colored box.

a) HA—sense strand b) antisense strand

Figure 11:
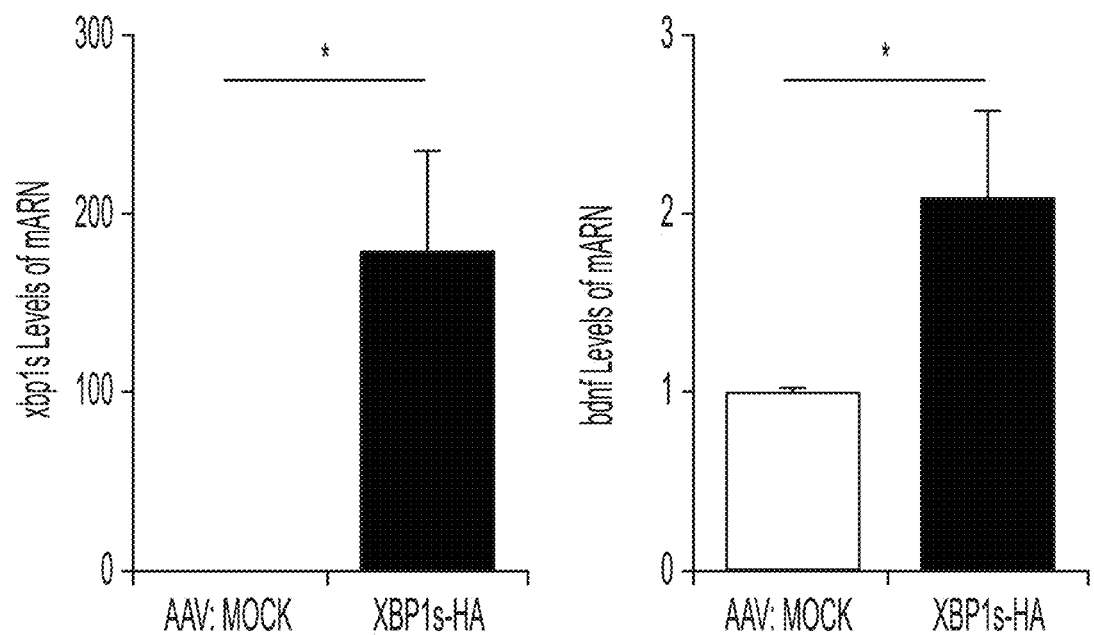

To see if the cognitive response is correlated with overexpression of any of the genes of the cluster (KIF 17, AMPA 3, BDNF, RYR3) related with the memory, the overexpression of the mARN of one of these genes in the hippocampus was evaluated. It was observed that a correlation exists between the increase of the mARN of the group of genes mentioned previously and the cognitive response (FIG. 11/17).

Experimental Test 2

To validate the results delivered in the experimental test 1, the virus was tested in another model of rodent using a cognitive test that evaluates the memory dependent on the hippocampus. Two different doses of AAV/XBP1s-HA (FIG. 12/17, right panel) were injected bilaterally in the CA3 region of the hippocampus of mice, and two weeks after the surgery their behavior was evaluated in the Oasis Maze (15) test.

Figure 12:
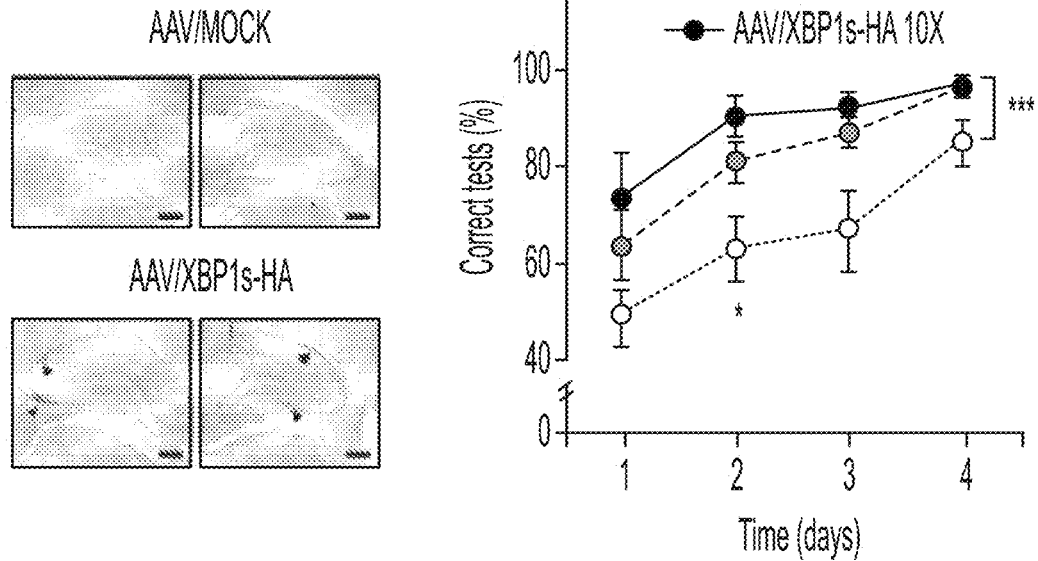
Figure 13:
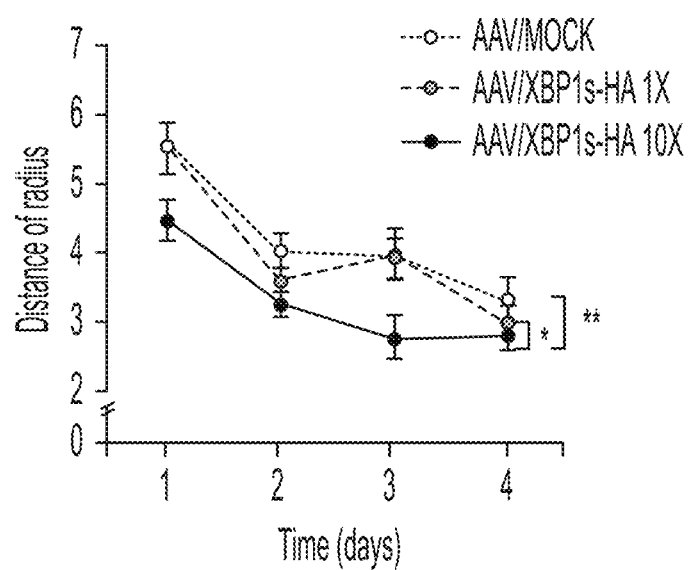
Figure 14:
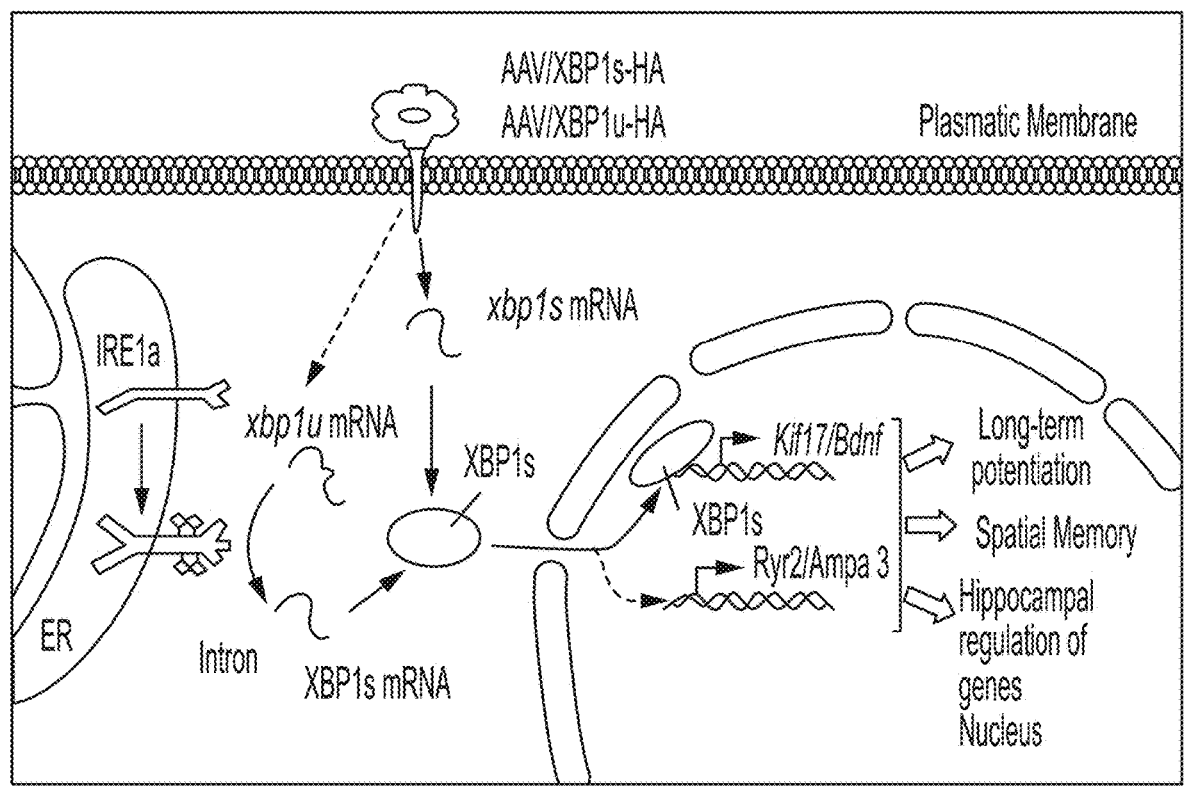
Figure 15:
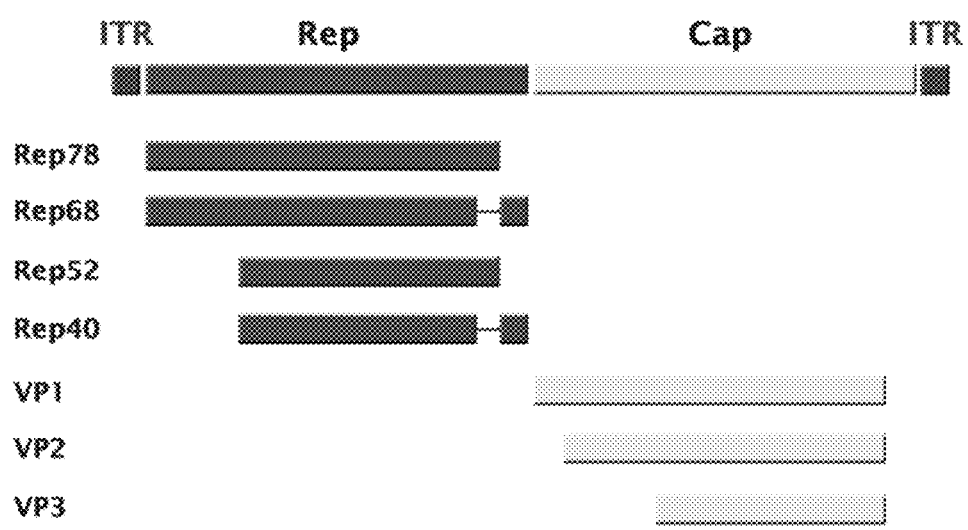
Figure 16:
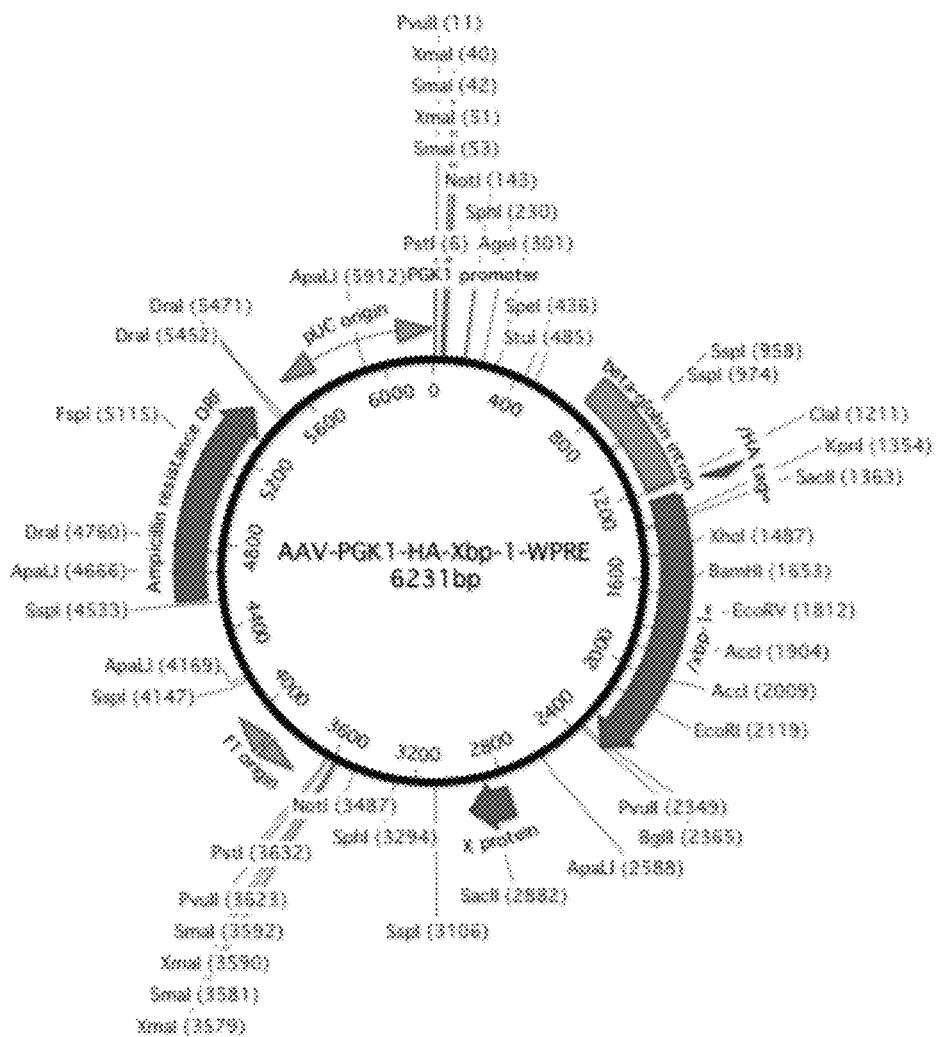

The mice that express XBP1s-HA in the hippocampus (FIG. 12/17, left panel) present a significant increase in the percentage of successful attempts to find food hidden in the labyrinth. Moreover, these effects were dependent on the dose (FIG. 12/17, right panel and FIG. 13/17).

Material and Methods

Animals and Surgical Procedures:

For all the experiments, male mice, 3-6 months old, were used for XBP1$^{Nes-/-}$, Tg$^{XBP1s}$ and mice of the wild type C57BL/6. The mice were maintained in a light-darkness cycle of 12:12 hours and they had free access to food and water, unless the experiment required it.

The guidelines established by the committee for the care and use of animals in the University of Chile, Chile were used for all the experiments in animals presented in this development.

Generation of Transgenic Mice XBP1s.

The cADN Xbp1s of mice was sub cloned in the Xho1 site of the vector[2] MoPrP.Xho to control the expression under the promotor PrP and the microinjection of cells CBA-C57BL/6 derived from pronuclei of mice of fertilized oocytes. The genetic state of the mice was confirmed by PCR of genomic DNA from tails of mice (3 weeks) using the splitters for XBP1s:

```
Sense strand:
5'-ACACGCTTGGGAATGGACAC-3'

Antisense strand:
5'-CCATGGGAAGATGTTCTGGG-3'
```

Behavioral Tests

All the experiments were performed blindly, and different cohorts of animals were used for each behavioral test.

Conditioning of contextual fear: In the first days, the animals were allowed to become accustomed in the chamber (Med Associates, Burlington, Vt.) for 2 minutes and then they were presented with a base noise (80 dB) for 30 seconds. After an interval of 2 seconds, the animals were exposed to an electric shock of 0.5 mA, which is known as an unconditioned stimulus (US). This procedure was repeated five times. Twenty-four hours after the training, the animals are placed in the original chamber once again and the immobility events are evaluated for 5 minutes to determine the associations of the US with the context. The immobility events are automated with the Med Associates software (Burlington, Vt.) designed to determine 30 observations in five minutes. This experiment was carried out at Case Western Reserve University (CWUR) Rodent Behavior Core and was then repeated at the Harvard Neurodiscovery Center.

The Flexibility of the Memory

The memory flexibility test was carried out according to the description of Chen et al (2000). The training is carried out up to ten tests per day, until the location of the platform is learned. Through a criterion a priori of three latent escapes of less than 20 seconds. After the finalization of the tests, the mouse was removed from the labyrinth, was dried and returned to his cubicle. The data related to the time spent in each quadrant of the pool was linked to a video tracking system of the water labyrinth (HVS Image, Hampton, United Kingdom).

Oasis Maze

A modified protocol of the Oasis Maze was used, that is a dry version equivalent to the water labyrinth in the requirement of hippocampal spatial navigation. The apparatus consisted of sand in an open field of 1.4 m in diameter, that is 50-cm above the floor with a 20-cm high wall, that is in an isolated room with constant distal visual signals. Twenty-one evenly spaced wells (4.5 cm in diameter, 2 cm high) were placed on the table and one of the wells is baited with 50 mg of food. Fourteen days after recovering from surgery, the task consisted in 15 tests of one minute each per session, one session per day, during four consecutive days. All the behavior of the animals was recorded on video, with the help of a video camera in zenithal position.

Startle Response

The mice were placed in a Plexiglas cylinder and were left at rest for five minutes. After the acclimatization, each subject was presented to 36 tests in one 9-minute test session. They are exposed to nine different levels of sound: 70, 74, 78, 82, 86, 90, 100, 110 and 120 (dB). Each stimulus was of 40 ms and was presented on four occasions with a pseudorandom purpose. The average interval between tests was of 15 s (it oscillated from 10 to 20 s). The startle response was registered during 65 ms (each measurement of the response of 1 ms) based on the appearance of the startle response. The maximum amplitude of the shock was registered during the 65 ms sampling window that was used as a dependent measure.

Rotarod

The mice were placed on a bar that rotates at 4 rpm during a minute of acclimation. The rod was accelerated at 0.1 rpm/s to 40.0 rpm. The test continued until all the mice fell off the rod. The latency in fallings and the rpm at the moment of the fall were registered for each mouse. Three tests were executed per mouse and an average calculated.

Hot Plate

The animal was placed on the plate at 55° C. The animal was observed until it showed a nociceptive response (for example, licking its rear legs, jumps or squeaks) or until the cut-off time is reached (30 seconds). The animal was removed and the latency of response was recorded. For the animals that do not respond before the cut-off time, the cut-off time was recorded.

Recognition of New Objects

The object recognition tests were carried out in the following manner. Twenty-four hours before the test the animals became accustomed to an open field for 15 minutes. The test wraps the presentation of two identical objects in an open field of 45×45 cm for ten minutes. The animals were allowed to explore freely and the frequency and duration of the explorations were quantified. One exploration was defined by direct visual contact at a distance of 1 cm or less, or a direct interaction with the object. After the training was concluded, the animals were placed again in their housecage for one hour. The level of the object recognition memory was measured by switching one of the objects in the open field and allowing the animal out to explore the two objects for five minutes. The novel object was different but its exploratory index was similar. The relationship of the total novelty to the exploration of the object was used to determine the exploratory discrimination relationship. The locomotor activity was measured and the exploration of both objects during the training and test sessions to identify any object side/preference or general differences in the locomotor/exploratory activity.

Open Field

The locomotor activity and the observations of behavior related to anxiety were made while the mouse was in an "open field". The open field consists of a 40-cm×40-cm box situated in a dimly lit room. The animals are placed in the open field and they are allowed to explore the enclosure freely for 15 minutes. During this period, the locomotor parameters such as the total distance of movement, speed, angular speed and the direction are measured to determine the basic locomotive activity and the presence of stereotypes.

Production of Adeno-Associated Vectors

The particles of the AAV serotype 6 (AAV2/6) virus were produced by the transfection of cells 293-AAV (Agilent Technologies, Santa Clara, Calif.) and they were purified in a gradient of iodixanol followed by affinity column chromatography. The number of particles of AAV that the genome contains in the suspension, as well as the infectivity of the vector's suspension in cells HEK293T were determined by means of TaqMan qPCR tests.

Preparation of the Adenoviral Plasmid (pAAV) for XBP1s.

For the development of this objective, the sequence of XBP1s murine was cloned in the adenoviral plasmid pAAV-PGK1-MCS, that expresses the transgene under the promotor PGK1. Due to the absence of antibodies that permit recognition of XBP1s in murine tissue, the sequence of the HA tag was included in the cloning strategy (FIG. 17/17 A), that will then allow us to identify the transduced cells and the expression of XBP1s (without excluding other epitope sequences such as Flag, Gfp, His and Myc, among others). Therefore, we generate the amplification of XBP1s with the sequence of the HA tag at the terminus 5' (left panel) and with the HA sequence in the terminus 3' (right panel). The clones obtained were confirmed by means of DNA sequencing. In this way, we generated the constructs pAAV PGK HA-XBP1s that codify for the fusion protein XBP1s with the HA tag at the end of the amino terminal and pAAV PGK XBP1s-HA with the HA tag at the end of the carboxyl terminal. The empty adenoviral plasmid pAAV PGK was utilized as a control.

To confirm the expression of the constructs generated we transfected HEK cells with the different constructs, after 48 hours of transfection we executed the extraction of proteins that were evaluated by means of WB using an anti-HA antibody.

Figure 17A:
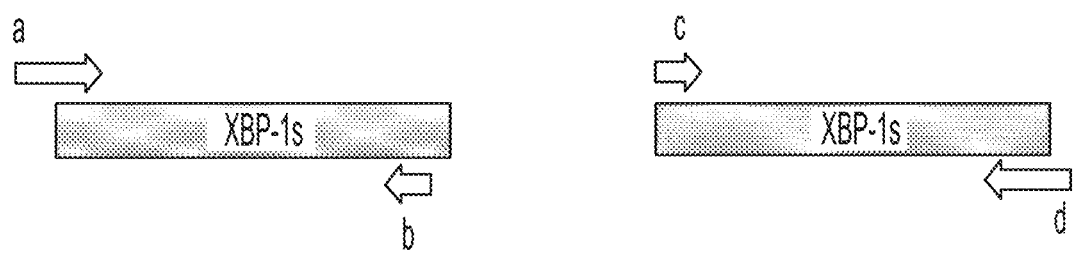
Figure 17B:
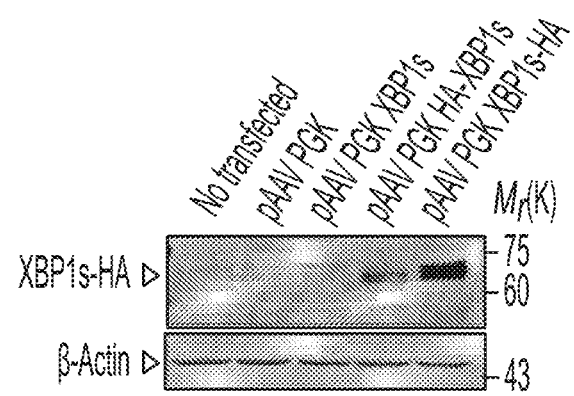

As can be seen in FIG. 17/17 B, we detected a band of the expected molecular weight for XBP1s (55 KDa) only in the cells transfected with the plasmid pAAV PGK HA-XBP1s and with pAAV PGK XBP1s-HA.

The cDNA XBP1s-HA that codifies C-terminal HA-labeled, the active form of XBP1 mice, was generated by amplifying by PCR of pCMVsport6-mXBP1s.

```
Sense strand
5'AGCTATCGATGAGATGATGGTGGTGGTGGCAGCGGCG3';

Anti-sense strand
5'ACGTAGATCTTTAGACGTAATCTGGAACATCGTATGGGTAGACACTAA
TCAGCTGGGGGAAAA 3'
```

And they were sub cloned in the expression vector pAAV-pgk1-MCS that is derived from the plasmid pAAV-CMV-MCS (Clontech).

Stereotaxic Injections

The mice were anesthetized using ketamine/xylazine anesthesia (Ketamine: 100 mg/kg, xylazine: 10 mg/kg, Vetcom, Chile) and were placed in a stereotaxic with bars in the nose and ear for the mice (David Kopf Instruments, U.S.A.). Bilateral injections of AAV/XBP1s-HA, AAV/MOCK, AAV/BDNF-GFP or AAV/GFP were executed with the following concentrations: $1\times10^6$ units of transduction/µl (TU) of AAV/XBP1s-HA and AAV/MOCK; $1\times10^9$ viral genomes/µl (VG) were injected for AAV/BDNF-GFP and AAV/GFP. The expression of EGFP was controlled by PCR in real time after the injection of the AAV to corroborate that the efficiency of the transduction was the same as that obtained in these experiments for both constructions (data not shown). The injection of AAV was executed in a single point, the injection of 2 or 3 µl in the CA1 region of the hippocampus using a 5 µl Hamilton syringe (Hamilton, U.S.A.) in the following coordinates: AP: −0.194 cm µl/min and the needle is left in its place for 5 minutes before the retraction of the needle.

For the stereotaxic injections in the mice, the animals were anesthetized using the isoflurane inhalation anesthetic (halogenated ether 2-chlorine-2-difluoromethoxy-1,1,1-trifluor-ethane) and they were maintained at 1.0-2.0% of isoflurane in oxygen at 100% and they are placed in a stereotaxic frame with the nose and ear with bars for mice. Bilateral injections of AAV/XBP1s-HA or AAV/MOCK were executed with the following concentrations: $1\times10^6$ TU (1×) or $1\times10^7$ TU (10×). The AAVs injection was placed at a single point, the injection of 2 µl in the CA3 region of the hippocampus using a 5 µl Hamilton syringe (Hamilton, U.S.A.) in the following coordinates: AP: −0.33 cm, ML: 0.36 cm, DV: −0.33 cm (according to the Paxinos and Watson atlas, 1998). The injection was carried out at a speed of 05 µl/min and the needle was left in place for 5 minutes before it was retracted.

Preparation of Tissues for the Biochemical Analysis.

The mice were sacrificed by narcosis of $CO_2$, the brains were removed, and the cortex, hippocampus, cerebellum and amygdala of both hemispheres were dissected rapidly in a plastic plate cooled with ice. The tissue was homogenized in 100 µl of phosphate buffered saline (PBS) (pH 7.4) supplemented with a mixture of protease inhibitors (Roche Applied Science, U.S.A.). The homogenized was divided to obtain mARN and the extraction of proteins was followed by standard purification and quantification protocols.

Extraction of ARN and PCR in Real Time.

The total ARN was isolated from the hippocampus, the amygdala, the cerebellum and the total brain. After the homogenization in PBS we have continued the ARN Trizol extraction protocol recommended by the manufacturer. The cDNA was synthesized with a kit of cDNA high capacity reverse transcription (Applied Biosystems). SYBR green and a System (Stratagene) Mx3005P QPCR were utilized for the quantitative RT-PCR. The relative amount of mARN was calculated by the comparative threshold cycle method with β-actin as control. The Primers of the sequences were obtained based on the PrimerBank (Table VII).

TABLE VII

| Target | Forward | Reverse |
|---|---|---|
| Ttr | 5'-TTGCCTCGCTGGACTGGTA-3' | 5'-TTACAGCCACGTCTACAGCAG-3' |
| Retn | 5'-CTGTGTCATACGCCAAGAACA-3' | 5'-GGGGAGGTACAGGATGTGGAT-3' |
| GRia1 | 5'-GTCCGCCCTGAGAAATCCAG-3' | 5'-CTCGCCCTTGTCGTACCAC-3' |
| Gria2 | 5'-GCCGAGGCGAAACGAATGA-3' | 5'-CACTCTCGATGCCATATCGTTG-3' |
| Gria3 | 5'-ACCATCAGCATAGGTGGACTT-3' | 5'-ACGTGGTAGTTCAAATGGAAGG-3' |
| Gria4 | 5'-GGGAGGTGACTCCAAGGACA-3' | 5'-CCAGTCATGGATAACCTGGCT-3' |
| Myo5b | 5'-CAGCAAGTGGTCAATGCACG-3' | 5'-TGGCGTAGTTGATACAAAACTGT-3' |
| Creb | 5'-AGCCGGGTACTACCATTCTAC-3' | 5'-GCAGCTTGAACAACAACTTGG-3' |
| Bdnf | 5'-CAGGTTCGAGAGGTCTGACGA-3' | 5'-CGCGTCCTTATGGTTTTCTTCG-3' |
| Camk1l | 5'-TGCCTGGTGTTGCTAACCC-3' | 5'-CCATTAACTGAACGCTGGAACT-3' |
| Ryr1 | 5'-CAGTTTTTGCGGACGGATGAT-3' | 5'-CACCGGCCTCCACAGTATTG-3' |
| Ryr2 | 5'-ATGCTTTAAGGCACAGCG-3' | 5'-CAGAGCCCGAATCATCCAGC-3' |
| Ryr3 | 5'-ACCAGCAGGAGCAAGTACG-3' | 5'-GGGGTCGTGTCAAAGTAGTCA-3' |
| Nr2a | 5'-ACGTGACAGAACGCGAACTT-3' | 5'-TCAGTGCGGTTCATCAATAACG-3' |
| Nr2b | 5'-GCCATGAACGAGACTGACCC-3' | 5'-GCTTCCTGGTCCGTGTCATC-3' |
| Pp2b/Caln | 5'-AAATGAGGCCAGCTACCAAAC-3' | 5'-CCCGATTTGTCCAAGTCCAG-3' |
| Kif17 | 5'-GGGGCATCATTCCCAGAGC-3' | 5'-TTGTGTACCGTGTGCATGGAC-3' |
| Stx17 | 5'-TCAAAGTGGCAGGAATTGCAG-3' | 5'-AATTTTCCACCTGTGAAGCCTAA-3' |
| Kcnk1 | 5'-GAGGAGCTGCCTTATGAGGAC-3' | 5'-TCCCAATTCCAATTTCCCGAG-3' |
| Xpo4 | 5'-CCCCCAGAAGTGATCGCTC-3' | 5'-TGGTTTCCAAAATATGCCTGCAA-3' |
| Csnk2a | 5'-AGGATAGCCAAGGTTCTGGGA-3' | 5'-CCATCGCTTACGGGAGTGTC-3' |
| Adb1 | 5'-GAACCCTGCAACTGTCGTC-3' | 5'-CCACGAGTAGGCCCATACC-3' |
| Pten | 5'-TGGATTCGACTTAGACTTGACCT-3' | 5'-GCGGTGTCATAATGTCTCTCAG-3' |
| Map2k3 | 5'-GCCTCAGACCAAAGGAAAATCC-3' | 5'-GGTGTGGGGTTGGACACAG-3' |
| Ucqr10 | 5'-ATCCCTTCGCGCCTGTACT-3' | 5'-GTGCTCGTAGATCGCGTCT-3' |
| Nipsnap1 | 5'-CACGGCGGCTATTCACGAA-3' | 5'-GAACGGAACCAGCTTCCTTCA-3' |
| Xbp1Δ | 5'-CCTGAGCCCCGGAGGAGAA-3' | 5'-CTCGAGCAGTCTGCGCTG-3' |
| Wfs1 | 5'-CCATCAACATGCTCCCGTTC-3' | 5'-GGGTAGGCCTCGCCAT-3' |
| Edem | 5'-AACCCAATGGCCTGTCTGG-3' | 5'-AAGCCCTCTGGAACTTGCG-3' |
| Bip | 5'-TCATCGGACGCACTTGGAA-3' | 5'-CAACCACCTTGAATGGCAAGA-3' |
| Actin | 5'-CTCAGGAGGAGCAATGATCTTGAT-3' | 5'-TACCACCATGTACCCAGGCA-3' |

Western Blot of Tissue.

The extraction of proteins based on the tissue of mice was carried out in RIPA Buffer (20 mM Tris pH 8.0, NaCl 150 mM, 0.1% of SDS, 0.5% deoxycholate, 0.5% of Triton X-100) that contains a mixture of inhibitors of the protease and a mixture of inhibitors of the phosphatase (Sigma, U.S.A.). An example of this quantification was executed with the BCA test kit (Pierce, U.S.A.). Total cellular extracts were separated by SDS-PAGE and were transferred to membranes of polyvinylidene difluoride. The following antibodies were used for the analysis of immunoblot: Hsp90 (1:3000 Santa Cruz), anti eIF2α phosphorylated, the total eIF2α and Hsp90 (1:1000, Cell Signaling), BDNF (1:1000, Alomone Labs), KIF17 (1:1000, Sigma), XBP1 (1:1000, Poly6195-BioLegend), β-actin and ATF4 (1:1000, Santa Cruz).

Preparation of the Tissue and the Histologic Analysis

The mice were anesthetized with the ketamine/xylazine mixture of anesthesia and they were fixed with paraformaldehyde at 4%. The mice were deeply anesthetized with 7% of chloral hydrate (350 mg/kg, ip) and they were fixed with paraformaldehyde at 4%. The brains were extracted, then fixed during the night at 4° C. in the same solution and subsequently placed at 30% of sucrose (Merck, U.S.A.) at 4° C. for 48 hours. The brains were frozen in an optimum compound for cutting coronal sections at an adequate temperature (Tissue Tek, U.S.A.): 25 μm for male mice and 50 μm for female mice that containing the hippocampus were cut in a cryostat (Leica, Germany) and then staining was executed in free-floating sections.

The immunostaining was executed via the universal kit plus ICQ LSAB (ABC Elite Kit, Vector Laboratories, U.S.A.). The sections were incubated with $H_2O_2$ at 3% in PBS for 30 minutes and were blocked for 2 hours with 0.5% of bovine serum albumin and 0.1% of Triton X-100. The sections were incubated during the night at 4° C. in a blocking solution with HA (1:800, Covance) as a primary antibody and they were washed three times with PBS and were incubated for one hour at room temperature with the biotinylated anti-mouse secondary antibody (1:1000). After rinsing three times, the sections were treated with avidin-biotin-peroxidase complex. The sections were developed using 3,3-diaminobenzidine for 5 minutes and they were visualized in an Olympus IX71 inverted microscope or in a DM5500 Leica for the digitalization of the complete sections.

Preparation and the Electrophysiology of the Slice of Hippocampus.

The slices of hippocampus were prepared according to standard procedures for mice aged 4-6 months. Transversal slices of 350 μm of the dorsal hippocampus were cut in artificial cold cephalorhachidian liquid (ACSF, in mM: 124 NaCl, 2.6 NaHCO3, 10 D-glucose, 2.69 KCl, 1.25 $KH_2PO_4$, $CaCl_2$ 2.5, 1.3 $MgSO_4$, and 2.60 $NaHPO_4$) using a vibratome (Leica VT 1000 s, Germany) and they were incubated in ACSF for more than one hour at room temperature. In all the experiments, picrotoxin was added (10 μM) to the ACSF perfusion means in order to suppress the inhibiting transmission GABAA. To evoke field excitatory postsynaptic potential (fEPSPs), Schaffer collateral fibers were activated for the bipolar cathodic stimulation, generated by a stimulator (Axon 700b, Molecular Devices, Sunnyvale, Calif.) connected to an isolation unit (Isoflex, AMPI, Jerusalem, Israel). To generate LTP, in mice $XBP1^{Nes-/-}$ that uses high frequency stimulation (HFS) that consists of three stimulus trains with an interval between trains of 20 s. Each train consisted of 100 Hz for 500 ms. In the $Tg^{XBP1s}$ mice we used the theta burst stimulation that consists of 5 stimulus trains with an interval between trains of 20 s. Each train consisted of 8 bursts at 5 Hz, each burst has 4 pulses at 100 Hz. The recordings were filtered at 2.0-3.0 kHz, sampling at 4.0 kHz using an A/D converter, and they are stored with a pClamp 10 computer (Molecular Devices).

Cultures and Neuronal Transfections.

The neuro2A cells and the HEK293T cells were obtained from the ATCC and were cultivated in a DMEM medium supplemented with 10% of bovine serum or 5%, respectively, and antibiotics (10000 U/ml of penicillin, 10 mg/ml of streptomycin) at 37° C. and 5% of $CO_2$. The cortical neurons and those of the hippocampus were obtained on the $18^{th}$ embryonic day described by Goslin and Banker (1991).

Statistics

The data is expressed as average and SEM. Depending on the experiments, the results were compared statistically using the Student's T test or the Mann-Whitney test, the two-way ANOVA followed by Holm-Sidack or Bonferroni as a post-hoc test or one-way Kruskal-Wallis ANOVA in ranges followed by the Dunn or Bonferroni Method as a post-hoc test.

REFERENCES

1.—Costa-Mattioli, M., Sossin, W. S., Klann, E. & Sonenberg, N. Translational control of long-lasting synaptic plasticity and memory. *Neuron* 61, 10-26, doi: 10.1016/j.neuron.2008.10.055 (2009).

2.—Park, H. & Poo, M. M. Neurotrophin regulation of neural circuit development and function. *Nat Rev Neurosci* 14, 7-23, doi:10.1038/nrn3379 (2013).

3.—Cirulli, F., Berry, A., Chiarotti, F. & Alleva, E. Intra-hippocampal administration of BDNF in adult rats affects short-term behavioral plasticity in the Morris water maze and performance in the elevated plus-maze. *Hippocampus* 14, 802-807, doi:10.1002/hipo.10220 (2004).

4.—Hall, J., Thomas, K. L. & Everitt, B. J. Rapid and selective induction of BDNF expression in the hippocampus during contextual learning. *Nat Neurosci* 3, 533-535, doi:10.1038/75698 (2000).

5.—Mizuno, M., Yamada, K., Olariu, A., Nawa, H. & Nabeshima, T. Involvement of brain-derived neurotrophic factor in spatial memory formation and maintenance in a radial arm maze test in rats. *J Neurosci* 20, 7116-7121 (2000).

6.—Rattiner, L. M., Davis, M. & Ressler, K. J. Differential regulation of brain-derived neurotrophic factor transcripts during the consolidation of fear learning. *Learn Mem* 11, 727-731, doi:10.1101/lm.83304 (2004).

7.—Mu, J. S., Li, W. P., Yao, Z. B. & Zhou, X. F. Deprivation of endogenous brain-derived neurotrophic factor results in impairment of spatial learning and memory in adult rats. *Brain Res* 835, 259-265 (1999).

8.—Patterson, S. L. et al. Recombinant BDNF rescues deficits in basal synaptic transmission and hippocampal LTP in BDNF knockout mice. *Neuron* 16, 1137-1145 (1996).

9.—Tao, X., Finkbeiner, S., Arnold, D. B., Shaywitz, A. J. & Greenberg, M. E. Ca2+ influx regulates BDNF transcription by a CREB family transcription factor dependent mechanism. *Neuron* 20, 709-726 (1998).

10.—Tao, X., West, A. E., Chen, W. G., Corfas, G. & Greenberg, M. E. A calcium responsive transcription factor, CaRF, that regulates neuronal activity-dependent expression of BDNF. *Neuron* 33, 383-395 (2002).

11. Carter B., adeno-associates for the delivery of genes, Lassic D. et al, Eds, "Gene" Therapy: Therapeutic mechanisms and strategies" . . . (Marcel Dekker, Inc., New York, N.Y., U.S.A., 2000) and Gao et al, J. Virol, 2004; 78 (12): 6381-6388.

12. Faulí Trillo C, "Tratado de Farmacia Galénica" (Ed Luzán 5, S A, Madrid, España, 1993). And Gennaro A, Ed. "Remington: The Science and Practice of Pharmacy", 20 ed. (Lippincott Williams Wilkins, Philadelphia, Pa., United States, 2003).

13. Shintani, A., Ono, Y., Kaisho, Y. & Igarashi, K. Characterization of the 5'-flanking region of the human brain-derived neurotrophic factor gene. *Biochem Biophys Res Commun* 182, 325-332 (1992).

14. Hetz, C. et al. Unfolded protein response transcription factor XBP-1 does not influence prion replication or pathogenesis. *Proceedings of the National Academy of Sciences of the United States of America* 105, 757-762, doi:10.1073/pnas.0711094105 (2008).

15. Lee, A. H., Iwakoshi, N. N. & Glimcher, L. H. XBP-1 regulates a subset of endoplasmic reticulum resident chaperone genes in the unfolded protein response. *Mol Cell Biol* 23, 7448-7459 (2003).

16. Product Data Sheet Paav-MCS Expression vector, Catalog Number: VPK-410.
17. Acosta-Alvear, D. et al. XBP1 controls diverse cell type- and condition-specific transcriptional regulatory networks. Molecular cell 27, 53-66, doi: 10.1016/j.molcel.2007.06.011 (2007).
18. Candace et al (2005) Journal of Pharmaceutical Sciences, volume 94 number (6), pages 1187-1195.
19. Constantini et al (2000) Gene Therapy volume 7, pages 93-10.
20. Ulusoy et al (1999) Molecular Therapy volume 17, no 9, pages 1574-1584.

TABLE II

Characteristics and sequence of the plasmid pAAV-MCS alone.
  1-130: left ITR 139-801: CMV Promotor 809-1301: Intron of human β-globin 1308-1383: MCS 1384-1862: PolyA 1902-2042: right ITR 2959-3819: Ampicillin resistance 5' cctgcaggcagctgcgcgctcgctcgctcactgaggccgccgggcg
tcgggcgacctttggtcgcccggcctcagtgagcgagcgagcgcgcagag
agggagtggccaactccatcactaggggttcctgcggccgcacgcgtgga
gctagttattaatagtaatcaattacgggtcattagttcatagcccata
tatggagttccgcgttacataacttacggtaaatggcccgcctggctgac
cgcccaacgaccccgcccattgacgtcaataatgacgtatgttcccata
gtaacgtcaatagggactttccattgacgtcaatgggtggagtatttacg
gtaaactgcccacttggcagtacatcaagtgtatcatatgccaagtacgc
ccctattgacgtcaatgacggtaaatggcccgcctggcattatgcccag
tacatgaccttatgggactttcctacttggcagtacatctacgtattagt
catcgctattaccatggtgatgcggttttggcagtacatcaatgggcgtg
gatagcggtttgactcacggggatttccaagtctccaccccattgacgtc
aatgggagtttgttttggcaccaaaatcaacgggactttccaaaatgtcgt
aacaactccgccccattgacgcaaatgggcggtaggcgtgtacggtggga
ggtctatataagcagagctcgatagtgaaccgtcagatcgcctggagacg
ccatccacgctgattgacctccatagaagacaccgggaccgatccagcct
ccgcggattcgaatcccggccgggaacggtgcattggaacgcggattccc
cgtgccaagagtgacgtaagtaccgcctatagagtctataggcccacaaa
aaatgctttcttcttttaatatactttttttgtttatcttatttctaatac
tttccctaatctctttcatcagggcaataatgatacaatgtatcatgcct
attgcaccattctaaagaataacagtgataatactgggttaaggcaatag
caatatactgcatataaatatactgcatataaattgtaactgatgtaaga
ggatcatattgctaatagcagctacaatccagctaccattctgcttttat
tttatggttgggataaggctggattattctgagtccaagctaggcccttt
tgctaatcatgttcatacctcttatcttcctcccacagctcctgggcaac
gtgctggtctgtgtgctggcccatcacttttggcaaagaattgggattcga
acatcgattgaattccccggggatcctctagagtcgacctgcagaagctt
gcctcgagcagcgctgctcgagagatctacgggtggcatccctgtgacc
ctccccagtgcctctcctggccctggaagttgccactccagtgcccacca
gccttgtcctaataaaattaagttgcatcatttttgtctgactaggtgtcc
ttctataatattatggggtggaggggggtggtatggagcaaggggcaagt
tgggaagacaacctgtagggcctgcggggtctattgggaaccaagctgga TABLE II-continued Characteristics and sequence of the plasmid gtgcagtggcacaatcttggctcactgcaatctccgcctcctgggttcaa
gcgattctcctgcctcagcctcccgagttgttgggattccaggcatgcat
gaccaggctcagctaattttttgtttttttggtagagacggggtttcacca
tattggccaggctggtctccaactcctaatctcaggtgatctacccacct
tggcctcccaaattgctgggattacaggcgtgaaccactgctcccttccc
tgtccttctgattttgtaggtaaccacgtgcggaccgagcggccgcagga
accctagtgatggagttggccactccctctctgcgcgctcgctcgctca
ctgaggccgggcgaccaaaggtcgcccgacgcccgggctttgcccgggcg
gcctcagtgagcgagcgagcgcgcagctgcctgcaggggcgcctgatgcg
gtattactccttacgcatctgtgcggtatttcacaccgcatacgtcaaag
caaccatagtacgcgccctgtagcggcgcattaagcgcggcgggtgtggt
ggttacgcgcagcgtgaccgctacacttgccagcgccctagcgcccgctc
catcgattcaccatccatctcgccacgacgccggcatcccgtcaagctc
taaatcgggggctccattagggaccgatttagtgctttacggcacctcga
ccccaaaaaacttgatttgggtgatggttcacgtagtgggccatcgccct
gatagacggttttcgccctttgacgaggagtccacgttattaatagtgg
actatgaccaaactggaacaacactcaaccctatctcgggctattcattg
atttataagggattttgccgatttcggcctattggttaaaaaatgagctg
atttaacaaaaatttaacgcgaatttttaacaaaatattaacgtttacaat
tttatggtgcactctcagtacaatctgctctgatgccgcatagttaagcc
agccccgacacccgccaacacccgctgacgcgccctgacgggcttgtctg
ctcccggcatccgcttacagacaagctgtgaccgtctccgggagctgcat
gtgtcagaggttttcaccgtcatcaccgaaacgcgcgagacgaaagggcc
tcgtgatacgcctatttttataggttaatgtcatgataataatggtttct
tagacgtcaggtggcactatcggggaaatgtgcgcggaacccctatttga
tattatctaaatacattcaaatatgtatccgctcatgagacaataaccct
gataaatgcttcaataatattgaaaaaggaagagtatgagtattcaacat
ttccgtgtcgcccttattcccttttttgcggcattttgccttcctgttat
gctcacccagaaacgctgtgaaagtaaaagatgctgaagatcagagggt
gcacgagtgggttacatcgaactggatctcaacagcggtaagatcatgag
agattcgccccgaagaacgattccaatgatgagcacattaaagactgcta
tgtggcgcggtattatcccgtattgacgccgggcaagagcaactcggtcg
ccgcatacactattctcagaatgacttggttgagtactcaccagtcacag
aaaagcatcttacggatggcatgacagtaagagaattatgcagtgctgcc
ataaccatgagtgataacactgcggccaacttacactgacaacgatcgga
ggaccgaaggagctaaccgcttttttgcacaacatgggggatcatgtaac
tcgccttgatcgttgggaaccggagctgaatgaagccataccaaacgacg
agcgtgacaccacgatgcctgtagcaatggcaacaacgttgcgcaaacta
ttaactggcgaactacttactctagcttcccggcaacaattaatagactg
gatggaggcggataaagttgcaggaccacttctgcgctcggcccttccgg
ctggctggttttattgctgataaatctggagccggtgagcgtgggtctcgc
ggtatcattgcagcactggggccagatggtaagccctcccgtatcgtagt
tatctacacgacggggagtcaggcaactatggatgaacgaaatagacaga
tcgctgagataggtgcctcactgattaagcattggtaactgtcagaccaa
gtttactcatatatactttagattgatttaaaacttcatttttaatttaa
aaggatctaggtgaagatcctttttgataatctcatgaccaaaatccctt
aacgtgagttttcgttccactgagcgtcagacccgctagaaaagatcaaa
ggatcttcttgagatccttttttttctgcgcgtaatctgctgcttgcaaac
aaaaaaaccaccgctaccagcggtggtttgtttgccggatcaagagctac
caactctttttccgaaggtaactggcttcagcagagcgcagataccaaat
actgtccttctagtgtagccgtagttaggccaccacttcaagaactctgt
agcaccgcctacatacctcgctctgctaatcctgttaccagtggctgctg
ccagtggcgataagtcgtgtcttaccgggttggactcaagacgatagtta
ccggataaggcgcagcggtcgggctgaacggggggttcgtgcacacagcc
cagcttggagcgaacgacctacaccgaactgagatacctacagcgtgagc
tatgagaaagcgccacgcttcccgaagggagaaaggcggacaggtatccg
gtaagcggcagggtcggaacaggagagcgcacgagggagcttccagggg
aaacgcctggtatctttatagtcctgtcgggtttcgccacctctgacttg
agcgtcgatttttgtgatgctcgtcaggggggcggagcctatggaaaaac
gccagcaacgcggcctttttacggttcctggccttttgctggccttttgc
tcacatgt 3'

TABLE III

Restriction map of AAV-PGK1-HA-Xbp-1-WPRE

PGK1    189 to  528 nt
Tag HA  1219 to 1248 nt
XBP1    1249 to 2367 nt
WPRE    2378 to 2967 nt

```
CCTGCAGGCAGCTGCGCGCTCGCTCGCTCACTGAGGCCGCCCGGGCAAAGCCCGGCGTCGGGCGACCTTTGGTCGCCCGGCCTCAGTGAGCGAGCGAGC    <100
GGAGCGTCCGTCGACGCGGCGAGCGAGCGAGCGAGCGAGTGACTTCCGGCAGCTCCGAATCCAGCGGCCCGCTTTCGGCGAAACCAGCGGCGAGTCACTCGCTCGCTCG
         10        20        30        40        50        60        70        80        90
GCGCAGAGAGGGAGTGGCCAACTCACTAGGGGTTCCTCGCGCCGCACGCGGATCACGAGACTAGCTCTGACGATGGTCGAGTAGGGA              <200
CGCGTCTCCTCCACCGGTTGAGTGATCCCCAAGGACGCGCCGGCGTGCGCCTAGTCTCTGATCGAGACGCTGCTACCAGCTCATGGCCATCCCCT
         110       120       130       140       150       160       170       180       190
GGGCGCTTTTCCCAAGGACATGCGCTTTAGCAGCCGCCCGCTGGGACACTTGGCGCTACACAAGTGGCCTCTGCCTCCACACATTCCACATCC        <300
CCCGCGAAAAGGGTTCCGTACGGCGAAATCGTCGGCGGCGCGGGCGACCCGTGAACCGCGATGTGTTCACCGGAGACCGAGCGTGTGTAAGTGTAGG
         210       220       230       240       250       260       270       280       290
                                                                                                    >mPGK Prom
ACCGGTAGGCGGAACCGGCTCCGTTCTTTGGTGGCCCCCTTCGCGCCACCTTCTACTCTCCCCTAGTCAGGAAGTTCCCCCCCGCAGCTCGCGT    <400
TGGCCATCCGCCTTGGCCGAGGCGAAGACCACCGGGGAAGCGCGGTGGAAGATGAGGAGGGATCAGTCAGTCCTTCGTCAAGGGGGGCGCCGTCGAGCGCA
         310       320       330       340       350       360       370       380       390
CGTGCAGGACGTGACAAATGGAAGTAGCACGTCTCACTAGTCTCTGCAGATGGCAGCAGCGGTGAGCAAATGGAAGCGGGTAGGCGTTTGGGAGCGG    <500
CACACGTCCTGCAGTTGTTTACCTTCATCGTGCAGAGTGATCAGAGACACGTGTACCTTCGTGGGACTCGTCTGTCGGACTCTTCGCCCATCCGAAACCCCGTCGC
         410       420       430       440       450       460       470       480       490
CCAATAGCAGCTTTGCTCTTCTGCGTTTCTGGGCTCAGAGGCTCAGAGAAGCCTCCGACCCTTCCCCACCCAGGCCTGGGCTCAGGGCGCGGCTCGCC    <600
GGTTATCGTCGAAACGAGGAAGCGCAAAGACCCGAGTCTCCGAGTCTCTTCGGAGGCTGGGAAGGAGGGTGGGTCCCACCCGAGACGGGTCCCGCCGCGCCGGGG
         510       520       530       540       550       560       570       580       590
CGAAGGTCTCCGGAGGCCCGGACCATTCTGCACGCTTCAAAAGCGGACGGCACAGCGGGCTCCAGGGCTGTTTCTCCTCCATCTCGGGCTTTCGACCTCTAGCGG    <700
GCTTCCAGGAGGCCTTCCGGGCCGTAAGACGTGCGAAGTTTTCGCGTGCAGCACGTGCGAAGAGGTAGGAGCTAGAGCCCGAAAGCTGGAGATCG
         610       620       630       640       650       660       670       680       690
GGATCGGATTCGAATCCCGGCCGAACGTGCATTGGAACCGGATTCCCGTGCCAAGAGTGACGTAAGTACCGCTATAGAGTCTTATAGGCCCACAA    <800
CCTAGCCTAAGCTTAGGGCCCGGCCTTGCCACGTAACCTTGCCTCAGGGGCACGGTTCTCATCATTCATGCGGATATCTCAGATATCCGGTGTT
         710       720       730       740       750       760       770       780       790
AAAATGCTTTCTTCTTTAATATACTTTTGTTTATCTTATTTCTAATACTTTCCCTAATCTCTTTCTTTCTTCAGGCAATAATGATAACAATGTATCATGC    <900
TTTTACGAAAGAAGAAAATTATATGAAAAAACAAATATGTATAAAAGATTATGAAGGGATTAGAGAAAGAAGTCCGTTATTACTATGTTACATAGTACG
         810       820       830       840       850       860       870       880       890
CTCTTTGCACCATTCTAAAGAATAACAGTGATAATTTCTGGGTTAAGGCAATAGCAAATATTTCTGCATATAAATATTTCTGCATATAAATTGTAACTGAT    <1000
GAGAAACGTGGTAAGATTCTTATTGTCACTATTAAAGACCCAATTCCGTTATCGTTTATATAAAGACGTATATTTATAAATTGACTA
         910       920       930       940       950       960       970       980       990
```

TABLE III-continued

Restriction map of AAV-PGK1-HA-Xbp-1-WPRE

```
GTAAGAGGTTTCATATTGCTAATAGCAGCTACAATTCCAGCTACCATTCTGCTTTTATTTTATGGTTGGATAAGGCTGATTATTCTGAGTCCAAGCTAG    <1100
CATTCTCCAAAGTTATAACGATTATCGTCGATTAGGTCATGGTTAAGACGAAAATAAAATACCAACCTATTCCGACCTAATAAGACTCAGGTTCGATC
        1010      1020      1030      1040      1050      1060      1070      1080      1090

GCCCTTTTGCTAATCATGTTCATATCCTCTATCTTCCTCCACAGTCTCCTGGGCAACGTGCTGGTCTGTGTGCCCATCACTTTGGCAAAGAATTGG     <1200
CGGGAAAACGATTAGTACAAGTATGGAGAATAGAAGGAGGTGTCGAGGACACCGACCAGACACACCGGGTAGTGAAACCGTTTCTTAACC
        1110      1120      1130      1140      1150      1160      1170      1180      1190
                                            >BA tag GATTCGAACATCGATGAGTGTACCCATACGATGTTCCAGATTACGAATGGTGGTGGCAGCGGCGGCCGAGCGCGGCCACGGCGCCCCAAAGTGC        <1300
CTAAGCTTGTACTCTTACATGGGATGCTACAAGGTCTAATGCTTACCACCACCGTCGCCGCCGGCTGCGCCGGTGCCGCCGGGGTTTCACG
        1210      1220      1230      1240      1250      1260      1270      1280      1290

TACTCTTATCTGGCCAGCCCGCTCCCGGCGGCCCGGCGGCTGCCTGCGCGCCGGCCAGGTCGGACAGGGTCGGAGGCGAGCGGGACACCGCAGGC       <1400
ATGAGAATAGACCGGTGGGCGAGGCCGCCGACGGACGCGCGGCCGGTCCAGCCTCCGCTCGCCAGCGTCCGGTCCG
        1310      1320      1330      1340      1350      1360      1370      1380      1390

TCGCAAGCGGCAGCGGCGCTCACGCACGACCCTGAGCCTGCGAGGAGAAAGCGCTGCGGAGGAGAAACTGAAAAACAGAGTAGCAGCGCAGACTGCTCAGAGATAGAAAG   <1500
AGCGTTCGCCGTCGCCGAGTGCGTGACTCGGAGCTCCTTTCGCGACGAGCGCTTGACTTTTGTCTCATCGCGTCGACGAGCTCTATCTTTC
        1410      1420      1430      1440      1450      1460      1470      1480      1490

AAAGCCCGGATGAGCGAGCTGGAGCAGCAGTGGTGATTGGAAGAAGAACAACTCCAGCTAGAAAATCAGCTTTTACGGAGAAACTCACG           <1600
TTTCGGGCCTACTCCGCTCGACCTCGTTCACCCATGGCTAAACCTTCTTGGTGTTTGAGGTCGATCTTTTAGTCGAAAATGCCCTCTTTTGAGTGC
        1510      1520      1530      1540      1550      1560      1570      1580      1590

GCCTTGTGTTGAAGACCAGGAGTTAAGAACCTTGGTCCTCAATTCTTGTGCAGAACACACGTTGAGCAGCTCTGATCCTGACGAGGTTCAGAGTGGAGGCCAAGGAGTGAGTAAG   <1700
CGGAACACCAACTCTTGGTCCTCAATTCTTGTGCAGAACACACGTTGAGCAGCTCTGATCCTGACGAGGTTCAGAGTGGAGGCCAAGGAGTGAGTAAG
        1610      1620      1630      1640      1650      1660      1670      1680      1690

GCTGTGGCCGGGTCTGCTGAGTCCGCAGCAGGTGCAGCCAGGTGCAGGCCAGTGTCACCTCCCCAGAACATCTTCCATGGACTCTGACACTGTTGCCTCTCTTCAGAT         <1800
CGACCGGCCAGACGGCCCCAGAGACGACTCAAGCGTCGCCACGTCCACGCTCCGGTCAACAGTGGAGGGGTCTTGTAGAAGGGTACCTGAGACTGTGACAACGGAGAAGTCTA
        1710      1720      1730      1740      1750      1760      1770      1780      1790

TCTGAGTCTGATATCCTTTTGGGCATTCTGGACAAGTTGACCCTGTCATGTTTTCAATGTCCTTCCCCAGAGTCTGCTAGTCTGGAGGAACTCCCAG        <1900
AGACTCAGACTATAGGAAAACCCGTTCAACCTGGACAGTCAAAAGTTTACAGGAAGGGGTCTTCAGACGATCAGACCTTCCTTGAGGGTC
        1810      1820      1830      1840      1850      1860      1870      1880      1890

AGGTCTACCCAGAAGGACTTCCTTACCAGCCTCCCTTTCTCTGTCAGTGGGACCTCATCAGCCAAGCTGGAAGCCATTAATGAACTCATTCGTTT         <2000
TCCAGATGGGTCTTCCTGGATCAAGGAATGGTCGGAGGGAAAAGAGACAGTCACCCCTGGAGTCGGTTCGACCTTCGGTAATTACTTGAGTAAGCAAA
        1910      1920      1930      1940      1950      1960      1970      1980      1990

TGACCATGTATACACCAAGCTCTAGTTTTAGAGATCCCCTCTGAGACAGAGAGTCAAACTAACGTGGTAGTGAAAATTGAGGAAGCACCTCTAAGCTCT         <2100
ACTGGTACATATGTGGTTCGGAGATCAAATCTCTAGGGGAGACTCTGTCTCTCAGTTTGATTGCACCATCACTTTAACTCCTTCGTGGAGATTCCGAG
        2010      2020      2030      2040      2050      2060      2070      2080      2090

TCAGAAGAGGATCACCCTGAATTCATTGTCAGTGAAGATGACTTCATCCCAGAGTCGGGCATCTCAAACCTGCTTTCATCCA             <2200
AGTCTTCTCCTAGTGGGACTTAAGTAACAGAGTCACTTCTTTCTCGGAAACCTTCACTGAAGTAGGGCTCGACCCGTAGAGTTTGGACGAAAGTAGGT
        2110      2120      2130      2140      2150      2160      2170      2180      2190
```

TABLE III-continued

Restriction map of AAV-PGK1-HA-Xbp-1-WPRE

```
GCCATTGTCTGAGACCACCTTCTGCCTGCTGACGCTCACAGTGACTGTGGATATGAGGGCTCCCCTTCAGTGACATGTCTTCTCCACTTGG        <2300
CGGTAACAGACTCTGGTGAAGAACGGACGACCTGCGAGTGCTCACTGACCATACTCCCGAGGGGAAGAGGAAGTCACTGTACAGAGAGTGAACC
  2210      2220      2230      2240      2250      2260      2270      2280      2290

TACAGACCACTCCTGGGAGGATACTTTTGCCAATGAACTTTTCCCCAGTGATTAGTGTCTAAAGATCTATTCCGATAATCAACCTCTGATTACAAAA        <2400
ATGTCTGGTGAGGACCCCTCCTATGAAAACGGTTACTTGAAAAGGGGTCGACTAATCACAGATTTCTAGATAAGGCTATTAGTTGAGACCTAATGTTTT
  2310      2320      2330      2340      2350      2360      2370      2380      2390

TTTGTGAAAGATTGACTGGTATTCTTAACTATGTTGCTCTTGTATGTGATACCTGCTTGTTGTATCATGCTATTGCTTCCCGTAT        <2500
AAACACTTTCTAACTGACCATAAGAATTGATACAACGAGGAAATGCGATACACCTATGCGACGAAATTACGGAACATAGTACGATAACGAAGGGCATA
  2410      2420      2430      2440      2450      2460      2470      2480      2490

GGCTTTCATTTCTCCTCCTTGTATAAATCCTGGTTGCTGTCTCTTTATGAGGAGTTGTGGCCCGTTGTCAGGCAACGTGGCGTGTGCACTGTGTTT        <2600
CCGAAAGTAAAGAGGAGAACATATTTAGGACCAACGACAGAGAAATACTCCTCAACACCGGGCAACAGTCCGTTGCACCGACCACGTGACACAAA
  2510      2520      2530      2540      2550      2560      2570      2580      2590

GCTGACGCAACCCCACTGTTGGGGCATTGCCACCACCTGTCAGCTCTTCGCTTCCGGGACTTTCGCTTTCCCCTCCTATTGCCACGGCGGAACTCATCG        <2700
CGACTCGCGTTGGGGTGACCAACCCCGTAACGGTGTGGACAGTCGAGGAAAGGCCCTGAAAAGCGAAAGGGAGGATAACGCTGCCGCCTTGAGTAGC
  2610      2620      2630      2640      2650      2660      2670      2680      2690

CCGCCTGCCTTGCCCGCTGCTGACAGGGGCTCGGCGTTGGGCACTGAAGTTCCGTGGTGTGTTGTCGGGGAAGCTGACGTCCTTTCCATGGCTGCTCGC        <2800
GGCGGACGGAACGGGCGACGACTGTCCCGAGCCGCACCGTGACTTGTTAAGGCACCACAACAGCCCTCGACTGCAGGAAGGTACCGACGAGCG
  2710      2720      2730      2740      2750      2760      2770      2780      2790

<FactorXa site
CTGTGTTGCCACCTGGATTCGCGGGGACGTCCTTCTGCTACGTCCCCTTCGGCCTGCCAATCCAGCGACCTTCCTTCCCGCGGCCTGCTGCCGGCTCTG        <2900
GACACAACGGTGGACCTAAGACGCCCCTGCAGGAAGACATGCGAGAAGACCGGAGTTAGGTCGCCTGGAAGGAGGGCGCCGGACGACGCGGCCGAGAC
  2810      2820      2830      2840      2850      2860      2870      2880      2890

CGGCCTCCTTCTTCCGTTCTTCCGCCTTCAGACGAGTTCGGATCTCCCTTTGGGCCGCCTCCCCGATGGATCTACGGGTGGCATCCGTGACCCCTC        <3000
GCCGGAAGGCAGAAGCGGAAGGCGGAAGTCTGCTCAGCCTAGAGGGAAACCCGGCGGAGGGCGTACCTAGATGCCACCGTAGGGACACTGGGAGG
  2910      2920      2930      2940      2950      2960      2970      2980      2990

CCCAGTGCCTTCTCGGGGCTGGAAGTTGCCACTCCAGTGCCCACCAGCCTTGTCTCCAACAGCCATGTGCATCATTTTGTGTGACTAGGTGGTTC        <3100
GGGTCAGGAGAGGACCCGGACCTTCAACGGTGAGGTCACGGGTGCTCGGGTTCCCAACCAAGACAGAGTTGTTAATTCAACGTAGTAAACAGACTGATCCAAGGAAG
  3010      3020      3030      3040      3050      3060      3070      3080      3090

TATAATATATTAGGGTGGACCGGGGTGGTATGGAGCAAGGGCAAGTTGGGAAGACAAGCTGTAGGGCCCTTATTGCCAACCAAGCTGGAGTG        <3200
ATATTATATAATACCCCACTCCGCCCCCACCATAACCTCGTTCAACCCTTCGTTGGACATCGGGGACTTCAACCGTAACCGCTAAGCTCGACCTCAC
  3110      3120      3130      3140      3150      3160      3170      3180      3190

>hGE polyA signal
CAGTGCCCACAATCTTGGCTCAGTGCAATCTCCGCCTTCCTGGGTTCAAGCGATTCTCCTGCCTCAGCCTCCGGAGTTGTTGGGATTCCAGCCATGATGAC        <3300
GTCACGGGTGTTAGAACCGAGTGGCCTTAGAGGCGGAGGACCCAAGTTCGCTAAGAGGACGGAGAAGGACTCGGAGGCTCAACAACCGTAAGGTCGTACTGAA
  3210      3220      3230      3240      3250      3260      3270      3280      3290

CAGGGTGCTAATTTTGTTTTTTGTAGAGACGGGGTTTCACCATATTGGCCAGGCTGGTCTCCAACTCGTAATCTCAGGTGATCTACCCGACCTTTG        <3400
GTCCCAGTCGATTAAAACAAAAACATCTCTGCCCCAAAGTGGTATACCGGTCCGACCAGAGATTGAGGATTAGAGTCCACTAGAGTCCCAACC
  3310      3320      3330      3340      3350      3360      3370      3380      3390
```

TABLE III-continued

Restriction map of AAV-PGK1-HA-Xbp-1-WPRE

```
CCTCCCAAATTGCTGGGATTACAGGCGTGAACCACTGCTCCCTTGCCTCTTCTTGATTTTGTAGGTAACCACGTGCGACCCAGCGCCGGCGAACC    <3500
GGACGGTTTAACGACCCTAATGTCCGACATTCGTGACGAGGAAGGACATGAACACTAAAAACATTCCATTGGTGCACGCCGCTGGCTCGCCGGCGTCCTTGG
       3410      3420      3430      3440      3450      3460      3470      3480      3490

CCTAGTGATGGAGTTGGCCACTCCCTCTTCTGCCGCGTCGCTCGCCGCTGCCGCGCGCCGCCGCAGCGGAGCGGCGCCAAAAGGTCGCCCACGCCCGGGCTTTGCCCGGGCGGCCC    <3600
GGATCACTACCTCAACGGTGAGGAGAGACGCCGCGGCCAGCGAGTGACTTCCGCCGTGGTTTCAGCGGCGCTGCCGCGCTGCCCAAACGGCGCCCGCGGGCCCGGG
       3510      3520      3530      3540      3550      3560      3570      3580      3590

TCAGTGAGCCAGCGAGCGCGCCAGGGCGCCTGCCTGCAGGGGCGCCCTGATGCGGTATTTCTCCTTACGCATCTGTGCGGTATTTCACACGCCATACGTCAAAGCA    <3700
AGTCACTCGGCTCGCTCGCGCGCGCTCGACGGTCGACGACTCCCCGCCGGACACGCCGGACTACGCCATAAAGAGGAATGCGTAGACACGCCATAAAGTGTGGCGTATGCAGTTTCGT
       3610      3620      3630      3640      3650      3660      3670      3680      3690

ACCATAGTACGCGCCCTGTAGCGGCCGCATTAAGCCGGGCCGGTGTGGTTACGGCAGCGTGACCGCTACACTTGCCAGCGCCCTACGGCGCCCCGCTCCT    <3800
TGGTATCATGCGCGGGACATCGCGCCGGTAATTCGCGCCGCCACACAACCGCCATCGCCTCGCACTGGCGATGTGAACGGTCGCGGGATCGCGGGAGGA
       3710      3720      3730      3740      3750      3760      3770      3780      3790

TTCGCTTCTTCCCTTCTCGCCACGTTCGCCGGCTTTCCCGTCAAGCTCTAAATCGGGGGACTCTCCCTTTAGGGTTCCGATTTAGTCTTTACGGCC    <3900
AAGCGAAGAAGGGAAGAGCGGTGCAAGCGCGCGAAAAGAGGAAATCAGCCCGAAATCACGAAATGCG
       3810      3820      3830      3840      3850      3860      3870      3880      3890

>M13 origin
                    <F1 ori

ACCTCGACCCCAAAAAACTTGATTGGGTCGATGGTTCACGTAGGTCGATGGGCCATCGCCCTGATAGACGTTTTTCGCCCTTTGACGTTGGAGTCCACGTTCTTT    <4000
TGGAGCTGGGTTTTTGAACTAAACCACTAGTGCATCACCAAGTGCATACCGGTACGGGACTATCTGCAAAAAGCGCAACCTCAGTGCAAGAAA
       3910      3920      3930      3940      3950      3960      3970      3980      3990

TAATAGTGGACTCTTGTTCCAAACTGGAACAACTACCCTATCTCGGGCTATTCTTTTGATTTATAAGGGATTTTGCCGATTTGCCGTATTGGTTA    <4100
ATTATCACCTGAGAACAAGGTTTGACTTGTTGTGAGTTGGGATAGAGCCCGATAAGAAACTAAATATATTCCCTAAACGGCTAAAGCCCGGATAACCAAT
       4010      4020      4030      4040      4050      4060      4070      4080      4090

AAAAATGAGCTGATTTAACAAAAATTTAACGCGAATTTTAACAAAATATTAACGTTTACAATTTTATGTGCACTCTCAGTACAATCTGCTCTGATGCCG    <4200
TTTTTACTCGACTAAATTGTTTTTAAATGTCGCTTAAAATGCACACCGTGAGAGTCATGTTAGACGAGACTACGGC
       4110      4120      4130      4140      4150      4160      4170      4180      4190

CATAGTTAAGCACCAGCCCGACACCCGCCAACACCCCGCCGCTCGAGCGGCCTTGTCTGCTGCCGAACGAGAGGGCCTAGGCGAATGTCTGTTCGACACTGCAGAG    <4300
GTATCAATTCGGTCGGGCGGTCGGGCGGTTGGGCGCAGTTGTGGGGCAGTAGCGCAGTGGGCGTGGGCACTTGCTCCTTACAGACAAGCTGTGACCGTCTC
       4210      4220      4230      4240      4250      4260      4270      4280      4290

CGGGAGCTGCATGTGTCAGAGGTTTCACCGTCATCATCACCGAAACGCCGAGAGCAAAGGCCCTCGATACGCCCTATTTTTATAGGTTAATGTCATGATAAA    <4400
GCCCCTCGACGACTACACAGTCTCCAAAGTGGCAGTAGGTCGTTGCCTTTCCGGAGACACTATGCGGATAAAAAATATCCAATTACAGTACTA
       4310      4320      4330      4340      4350      4360      4370      4380      4390

>Amp prom

ATAATGGTTTCTTAGACGTCAGGTGGCACTTTTCGGGGAAATGTGCGCGGAACCCCTATTTGTTTATTTTTCTAAATACATTCAAATATGTATCCGCTCA    <4500
TATTACCAAAGAATCTGCAGTCCACCGTGAAAAGCCCCTTTACACGCGCCTTGGGGATAAACAAATAAAAGATTTATCTGAAGTTTATAGATAGGCGAGT
       4410      4420      4430      4440      4450      4460      4470      4480      4490
```

TABLE III-continued

Restriction map of AAV-PGK1-HA-Xbp-1-WPRE

```
TGAGACAATAACCCTGATAAATGCTTCAATAATATTGAAAAAGGAAGAGTATGAGTATTCAACATTTCCGTCGCCCTTATTCCCTTTTTGCGACATT      <4600
ACTCTGTTATTGGGACTATTTACGAAGTTATTATAGAACTTTTCCTTCGTAGAAGTTGTAAAGCACAGCGGAATAAGGGAAAAAACGCCGTAA
        4510      4520      4530      4540      4550      4560      4570      4580      4590

TTGCCTTCCTGTTTTGCTCACCCAGAAACGCTGTGAAAGCTGTGAAAGATCGTGAAGATCAGTTGGGTGCACGAGTCAGTTGGGTTACATCGAACTGGATCTCAAC      <4700
AACGGAAGACAAAAACGAGTGGGTCTTTGCGACCACTTCATTTTCATCATTCTACGACTTCTAGTCAACTTCAACCCACCTGCTCACCCAATGTAGCTTGACCTAGAGTTG
        4610      4620      4630      4640      4650      4660      4670      4680      4690

AGCGGTAAGATCCTTGAGAGTTTTCGCCCCGAAGAACGTTTCCAATGATGAGCACTTTAAAGTTCTGCTATGTCGCGCGGTATTATCCCGTATTGACG      <4800
TCGCCATTCTAGGAACTCTCAAAAGCGGGGCTTCTTGCAAAGGTTACTACTCGTGAAAATTTCAAGACGATACAGCGCCATAATAGGGCATAACTGG
        4710      4720      4730      4740      4750      4760      4770      4780      4790

CCGGGCAAGGGCAACTCGGTCGCCCGCATCACACTATTCTCAGAATGACTTGGTTGAGTACTCACCAGTCACAGAAAAGCATCTTACGATGCATGACAAGT      <4900
GGCCCGTTCCGTTGAGCCAGCGGGCCGTATGTGATAAGAGTCTTACTGAACCAACTCATGAGTCCAGTGTCAGTCTGTTTTCGTAGAATGCTACCGTACTGTCA
        4810      4820      4830      4840      4850      4860      4870      4880      4890

AAGAGAATTATGCAGTGCTGCCATAACCATGAGTGATAACACTGCGCGCCAACTTACTTCTGACAACGATCGGAGGACCGAAGGAGCTAACCGCTTTTTG      <5000
TTCTCTTAATACGTCACGACGGTATTGGTACTCACTATTGTGACACGCGTTGCTAGCCTCCTGGCTTCCTCGATTGGCGAAAAAC
        4910      4920      4930      4940      4950      4960      4970      4980      4990

CACAACACATGGGCGATCATGTAACTCGCCTTGATCGTTGGGAACCGAGCTGAATGAACCATACCAAACGACGAGCTGACACCACGATGCCTGTAGTGCAA      <5100
GTGTTGTACCCGCTAGTACATTGAGCGGAACTAGCAACTCCTTGGCTCGACTTACTTGGCTCTGCAGTGTGGTGCTACGGACATCGTT
>AmpR
        5010      5020      5030      5040      5050      5060      5070      5080      5090

TGGCAACAACGTTGCGCAAACTATTAACTCGCGAACTACTTACTCTAGCTTCCCGGCAACAATTAATAGACTGCGATGGAGGCGGATAAAGTTGCAGGACC      <5200
ACCGTTGTTGCAACGCGTTTGATAATTGAGCGCTTGATGAGATCGAAGGGCCGTTGTTAATTATCTGACGCTACCTCGCCTATTTCAACGTGCTGG
        5110      5120      5130      5140      5150      5160      5170      5180      5190

ACTTCTGCGCTCGGCCCCTTCGGCTGGTTTATTGGTGATAAATCTGGAGCCGGTGACCGTGGGTCTCCACCCAGAGCCCATAGTAACGTCGTGACCGCGGTCTA      <5300
TGAAGACGCGAGCCGGAGGCCGACCGACCAAATAACGACTATTTAGACCTCGGCCACTGGCACCCAGAGGTGGGTCTCGGTATCATTGCAGACTGGGGCCAGAT
        5210      5220      5230      5240      5250      5260      5270      5280      5290

GGTAAAGCCCGTCCCGTATCGTACTTATTCTACACGACGGGAGTCAGGCAGTCCCAGTGCCCCTGGAGTCCCCAGTCCGTTGATACCTCGTTGCTTTATCTGTCCATCCACGGAGTGACTAAT      <5400
CCATTCGGAGGGCATACCATCAATAGATGTGCTGCCCTCAGTCGGGGGACCTCAGGGGTCACGGGGACCTCAGGGGTCAGGCAACTATGGAGCAACTATGGAGCAACGATT
        5310      5320      5330      5340      5350      5360      5370      5380      5390

AGCATTGGTAACTGCTCAGACCAAGTTACTCATATATCTTTAGATTGATTTAAAACTTCATTTTAATTTAAAAAGGATCTAGGTGAAGATCCTTTTGA      <5500
TCGTAACCATTGACAGTCTGGTTCAAATGAGTAATATATAATCTAACTAAATTTTGAAGTAAAAAATTAAATTTTCCTAGATCCACTTCTAGGAAAAACT
        5410      5420      5430      5440      5450      5460      5470      5480      5490

TAATCTCATGACCAAAATCCCTTAACTGTCGTTTCGTTCACTGAGCGTCAGACCCCGTAGAAAAGATCAAAGATCTCTTGAGATCCTTTTTTTCTG      <5600
ATTAGAGTACTGGTTTTAGGGAATTGCACTCAAAAGCAAGGTGACTCGCAGTCTGGGGCATCTTCTAGTAAAGAACTCTAGGAAAAAAAAAGAC
        5510      5520      5530      5540      5550      5560      5570      5580      5590

CGCGTAATCTGCTGCTTGCAAACAAAAAAACCACCGCTACCAGCGGTGGTTTGTTTGCCGGATCAAGAGCTACCAACTCTTTTTCCGAAGGTAACTGGCT      <5700
GCGCATTAGACGACGAACGTTGTTTTTTTGGTGGCGATGGTCGCCACCAAACAAACGGCTCAGTTCTGCATGGTCGTCGAAAAAACGGCTTCCATTGACCGA
        5610      5620      5630      5640      5650      5660      5670      5680      5690
```

TABLE III-continued

Restriction map of AAV-PGK1-HA-Xbp-1-WPRE

```
TCAGCAGAGCGCAGATACCAAATACTGTCCTTCTTAGTGTAGCCGTAGTTAGGCCACCACTTCAAGAACTCTGTAGCACCCGCCTACACCTCGCTCTGCT    <5800
AGTCGTCTCCGTCTATGGTTTATGACAGGAAGATCACATCGGCATCAATCCGGTGGTGAAGTTCTTGAGACATCGTGGCGATGTATGGAGCCGAGCGA
     5710      5720      5730      5740      5750      5760      5770      5780      5790

>ColE1 origin
                                                                |
AATCCTGTTACCAGTGGCTGCTGCCAGTGGCGATAAGTCGTGTCTTACCGGGTTGGACTCAAGACGATTGTTACCGGATAAGGCGCAGCGGTCGGGCTGA    <5900
     5810      5820      5830      5840      5850      5860      5870      5880      5890

ACGGGGGGTTCGTGCACACAGCCCAGCTTGGAGCGAACGACCTACACCGAACTGAGATACGTACAGCGTGAGCTATGAGAAAGCGCCACCTTCCCGAAGA    <6000
TGCCCCCCAAGCACGTGTGTCGGGTCGAACCTCGCTTGCTGGATGTGGCTTGACTCTATGATGTCGCACTCGATACTCTTTCGCGGTGCGAAGGGCTTC
     5910      5920      5930      5940      5950      5960      5970      5980      5990

GGAGAAAGGCCGGACAGGTATCCGGTAAGCGGCAGGGTCGGAACAGGAGAGCGCACGAGGGAGCTTTCCAGGGGGGAAACGCCTGGTATCTTTATAGTCCTGT    <6100
CCTCTTTCCGCCTGTCCATAGGCCATTCGCCGTCCCAGCTTGCCCGTGTCCTCGCCAGCAGTCTCCCTTTGCGGACCATAGAAAATATCAGGAC
     6010      6020      6030      6040      6050      6060      6070      6080      6090

CGGGTTTCGGCCACCTTCGACTTGAGCGTCGATTTTTGTGATGCTCGTCAGGGGCGGAGCCTATGGAAAAACGCCAGCAACGCGGCCTTTTTACGGTTC    <6200
GCCCAAAGCCGTGGAAGCTGAACTCGCAGCTAAAAACACTACGAGCAGTCCCCCCGCCTCGGATACCTTTTGCGGTCGTTGCGCCGGAAAAATGCCAAG
     6110      6120      6130      6140      6150      6160      6170      6180      6190

CTGGCCCTTTTGCTGGCCTTTTGCTCACATGT    <6231
GACCGGGAAAACGACCGGAAAACGAGTGTACA
     6210      6220      6230

Features:
ColE1: [5560:6183]
F1 ori: [4154:3714]
M13 origin [3709:4161]
AmpR: [4749:5408]
hGE polyA signal: [2977:3257]
mPGK Prom: [189:528]
Amp prom: [4481:4509]
BA tag:[1222:1248]
FactorXa Site: [2861:2850]
```

TABLE IV

```
Xbp1s (Mouse)
ORIGIN
    1   ctagggtaaa accgtgagac tcggtctgga aatctggcct gagaggacag cctggcaatc
   61   ctcagccggg gtggggacgt ctgccgaaga tccttggact ccagcaacca gtggtcgcca
  121   ccgtccatcc accctaaggc ccagtttgca cggcggagaa cagctgtgca gccacgctgg
  181   acactcaccc cgcccgagtt gagcccgccc cgggactac aggaccaata agtgatgaat
  241   atacccgcgc gtcacggagc accggccaat cgcggacggc acgaccccta gaaaggctgg
  301   gcgcggcagg aggccacggg gcggtggcgg cgctggcgta gacgtttcct ggctatggtg
  361   gtggtggcag cggcgccgag cgcggccacg gcggccccca aagtgctact cttatctggc
  421   cagcccgcct ccggcggccg ggcgctgccg ctcatggtac ccggtccgcg ggcagcaggg
  481   tcggaggcga gcgggacacc gcaggctcgc aagcggcagc ggctcacgca cctgagcccg
  541   gaggagaaag cgctgcggag gaaactgaaa aacagagtag cagcgcagac tgctcgagat
  601   agaaagaaag cccggatgag cgagctggag cagcaagtgg tggatttgga agaagagaac
  661   cacaaactcc agctagaaaa tcagctttta cgggagaaaa ctcacggcct tgtggttgag
  721   aaccaggagt taagaacacg cttgggaatg gacacgctgg atcctgacga ggttccagag
  781   gtggaggcca aggggagtgg agtaaggctg gtggccgggt ctgctgagtc cgcagcaggt
  841   gcaggcccag ttgtcacctc cccagaacat cttcccatgg actctgacac tgttgcctct
  901   tcagattctg agtctgatat ccttttgggc attctggaca agttggaccc tgtcatgttt
  961   ttcaaatgtc cttccccaga gtctgctagt ctggaggaac tcccagaggt ctacccagaa
 1021   ggacctagtt ccttaccagc ctcccttcct ctgtcagtgg ggacctcatc agccaagctg
 1081   gaagccatta atgaactcat tcgttttgac catgtataca ccaagcctct agttttagag
 1141   atcccctctg agacagagag tcaaactaac gtggtagtga aaattgagga agcacctcta
 1201   agctcttcag aagaggatca ccctgaattc attgtctcag tgaagaaaga gcctttggaa
 1261   gatgacttca tcccagagct gggcatctca aacctgcttt catccagcca ttgtctgaga
 1321   ccaccttctt gcctgctgga cgctcacagt gactgtggat atgagggctc cccttctccc
 1381   ttcagtgaca tgtcttctcc acttggtaca gaccactcct gggaggatac ttttgccaat
 1441   gaacttttcc cccagctgat tagtgtctaa agagccacat aacactgggc cccttcccct
 1501   gaccatcaca ttgcctagag gatagcatag gcctgtctct ttcgttaaaa gccaaagtag
 1561   aggctgtctg gccttagaag aattcctcta aagtatttca aatctcatag atgacttcca
 1621   agtattgtcg tttgacactc agctgtctaa ggtattcaaa ggtattccag tactacagct
 1681   tttgagattc tagtttatct taaaggtggt agtatactct aaatcgcagg gagggtcatt
 1741   tgacagtttt ttcccagcct ggcttcaaac tatgtagccg aggctaggca gaaacttctg
 1801   accctcttga ccccacctcc caagtgctgg gcttcaccag gtgtgcacct ccacacctgc
 1861   ccccccgaca tgtcaggtgg acatgggatt catgaatggc ccttagcatt tctttctcca
 1921   ctctctgctt cccaggtttc gtaacctgag ggggcttgtt ttcccttatg tgcatttttaa
 1981   atgaagatca agaatctttg taaaatgatg aaaatttact atgtaaatgc ttgatggatc
 2041   ttcttgctag tgtagcttct agaaggtgct ttctccattt atttaaaact accccttgcaa
 2101   ttaaaaaaaa agcaacacag cgtcctgttc tgtgatttct agggctgttg taatttctct
 2161   ttattgttgg ctaaaggagt aatttatcca actaaagtga gcataccact tttaaagtc
 2221   aaaaaaaaaa aaaaaaaa
```

TABLE V

Xbp1u (Mouse)
ORIGIN

```
   1 ctagggtaaa accgtgagac tcggtctgga aatctggcct gagaggacag cctggcaatc
  61 ctcagccggg gtggggacgt ctgccgaaga tccttggact ccagcaacca gtggtcgcca
 121 ccgtccatcc accctaaggc ccagtttgca cggcggagaa cagctgtgca gccacgctgg
 181 acactcaccc cgcccgagtt gagcccgccc ccgggactac aggaccaata agtgatgaat
 241 atcccgcgc gtcacggagc accggccaat cgcggacggc cacgacccta gaaaggctgg
 301 gcgcggcagg aggccacggg gcggtggcgg cgctggcgta gacgtttcct ggctatggtg
 361 gtggtggcag cggcgccgag cgcggccacg gcggccccca aagtgctact cttatctggc
 421 cagcccgcct ccggcggccg ggcgctgccg ctcatggtac ccggtccgcg ggcagcaggg
 481 tcggaggcga gcgggacacc gcaggctcgc aagcggcagc ggctcacgca cctgagcccg
 541 gaggagaaag cgctgcggag gaaactgaaa aacagagtag cagcgcagac tgctcgagat
 601 agaaagaaag cccggatgag cgagctggac cagcaagtgg tggatttgga agaagagaac
 661 cacaaactcc agctagaaaa tcagctttta cgggagaaaa ctcacggcct tgtggttgag
 721 aaccaggagt taagaacacg cttgggaatg gacacgctgg atcctgacga ggttccagag
 781 gtggaggcca aggggagtgg agtaaggctg gtggccgggt ctgctgagtc cgcagcactc
 841 agactatgtg cacctctgca gcaggtgcag gcccagttgt cacctcccca gaacatcttc
 901 ccatggactc tgacactgtt gcctcttcag attctgagtc tgatatcctt ttgggcattc
 961 tggacaagtt ggaccctgtc atgttttttca aatgtccttc cccagagtct gctagtctgg
1021 aggaactccc agaggtctac ccagaaggac ctagttcctt accagcctcc ctttctctgt
1081 cagtggggac ctcatcagcc aagctggaag ccattaatga actcattcgt tttgaccatg
1141 tatacaccaa gcctctagtt ttagagatcc cctctgagac agagagtcaa actaacgtgg
1201 tagtgaaaat tgaggaagca cctctaagct cttcagaaga ggatcaccct gaattcattg
1261 tctcagtgaa gaaagagcct ttggaagatg acttcatccc agagctgggc atctcaaacc
1321 tgctttcatc cagccattgt ctgagaccac cttcttgcct gctggacgct cacagtgact
1381 gtggatatga gggctcccct tctcccttca gtgacatgtc ttctccactt ggtacagacc
1441 actcctggga ggatactttt gccaatgaac ttttccccca gctgattagt gtctaaagag
1501 ccacataaca ctgggcccct ttccctgacc atcacattgc ctagaggata gcataggcct
1561 gtctctttcg ttaaaagcca agtagaggc tgtctggcct tagaagaatt cctctaaagt
1621 atttcaaatc tcatagatga cttccaagta ttgtcgtttg acactcagct gtctaaggta
1681 ttcaaaggta ttccagtact acagcttttg agattctagt ttatcttaaa ggtggtagta
1741 tactctaaat cgcagggagg gtcatttgac agttttttcc cagcctggct tcaaactatg
1801 tagccgaggc taggcagaaa cttctgaccc tcttgacccc acctcccaag tgctgggctt
1861 caccaggtgt gcacctccac acctgccccc ccgacatgtc aggtggacat gggattcatg
1921 aatggcccctt agcatttctt tctccactct ctgcttccca ggtttcgtaa cctgaggggg
1981 cttgttttcc cttatgtgca tttttaaatga agatcaagaa tctttgtaaa atgatgaaaa
2041 tttactatgt aaatgcttga tggatcttct tgctagtgta gcttctagaa ggtgctttct
2101 ccatttattt aaaactaccc ttgcaattaa aaaaaaagca acacagcgtc ctgttctgtg
2161 atttctaggg ctgttgtaat ttctctttat tgttggctaa aggagtaatt tatccaacta
2221 aagtgagcat accactttt aaagtcaaaa aaaaaaaaaa aaaa
```

TABLE VIII

Xbp1s (Human)
ORIGIN
```
   1 ggcgctgggc ggctgcggcg cgcggtgcgc ggtgcgtagt ctggagctat ggtggtggtg
  61 gcagccgcgc cgaacccggc cgacgggacc cctaaagttc tgcttctgtc ggggcagccc
 121 gcctccgccg ccggagcccc ggccggccag gccctgccgc tcatggtgcc agcccagaga
 181 ggggccagcc cggaggcagc gagcggggg ctgccccagg cgcgcaagcg acagcgcctc
 241 acgcacctga gccccgagga gaaggcgctg aggaggaaac tgaaaaacag agtagcagct
 301 cagactgcca gagatcgaaa gaaggctcga atgagtgagc tggaacagca agtggtagat
 361 ttagaagaag agaaccaaaa acttttgcta gaaaatcagc ttttacgaga gaaaactcat
 421 ggccttgtag ttgagaacca ggagttaaga cagcgcttgg ggatggatgc cctggttgct
 481 gaagaggagg cggaagccaa ggggaatgaa gtgaggccag tggccgggtc tgctgagtcc
 541 gcagcaggtg caggcccagt tgtcaccccct ccagaacatc tccccatgga ttctggcggt
 601 attgactctt cagattcaga gtctgatatc ctgttgggca ttctggacaa cttggaccca
 661 gtcatgttct tcaaatgccc ttccccagag cctgccagcc tggaggagct cccagaggtc
 721 tacccagaag gacccagttc cttaccagcc tccctttctc tgtcagtggg gacgtcatca
 781 gccaagctgg aagccattaa tgaactaatt cgttttgacc acatatatac caagcccta
 841 gtcttagaga taccctctga cacagagagc caagctaatg tggtagtgaa aatcgaggaa
 901 gcacctctca gccctcaga gaatgatcac cctgaattca ttgtctcagt gaaggaagaa
 961 cctgtagaag atgacctcgt tccggagctg gtatctcaa atctgctttc atccagccac
1021 tgcccaaagc catcttcctg cctactggat gcttacagtg actgtggata cggggggttcc
1081 cttttcccat tcagtgacat gtcctctctg cttggtgtaa accattcttg ggaggacact
1141 tttgccaatg aactcttttcc ccagctgatt agtgtctaag gaatgatcca atactgttgc
1201 ccttttcctt gactattaca ctgcctggag gatagcagag aagcctgtct gtacttcatt
1261 caaaaagcca aaatagagag tatacagtcc tagagaattc ctctatttgt tcagatctca
1321 tagatgaccc ccaggtattg tcttttgaca tccagcagtc caaggtattg agacatatta
1381 ctggaagtaa gaaatattac tataattgag aactacagct tttaagattg tacttttatc
1441 ttaaagggt ggtagttttc cctaaaatac ttattatgta agggtcatta gacaaatgtc
1501 ttgaagtaga catggaattt atgaatggtt ctttatcatt tctcttcccc cttttttggca
1561 tcctggcttg cctccagttt taggtccttt agtttgcttc tgtaagcaac gggaacacct
1621 gctgagggg ctctttccct catgtatact tcaagtaaga tcaagaatct tttgtgaaat
1681 tatagaaatt tactatgtaa atgcttgatg gaattttttc ctgctagtgt agcttctgaa
1741 aggtgctttc tccatttatt taaaactacc catgcaatta aaaggtacaa tgcaaaaaaa
1801 aaaaaaaaa
```

TABLE IX

Xbp1u (Human)
ORIGIN
```
   1 ggcgctgggc ggctgcggcg cgcggtgcgc ggtgcgtagt ctggagctat ggtggtggtg
  61 gcagccgcgc cgaacccggc cgacgggacc cctaaagttc tgcttctgtc ggggcagccc
 121 gcctccgccg ccggagcccc ggccggccag gccctgccgc tcatggtgcc agcccagaga
 181 ggggccagcc cggaggcagc gagcggggg ctgccccagg cgcgcaagcg acagcgcctc
 241 acgcacctga gccccgagga gaaggcgctg aggaggaaac tgaaaaacag agtagcagct
```

TABLE IX-continued

```
 301  cagactgcca gagatcgaaa gaaggctcga atgagtgagc tggaacagca agtggtagat
 361  ttagaagaag agaaccaaaa acttttgcta gaaaatcagc ttttacgaga gaaaactcat
 421  ggccttgtag ttgagaacca ggagttaaga cagcgcttgg ggatggatgc cctggttgct
 481  gaagaggagg cggaagccaa ggggaatgaa gtgaggccag tggccgggtc tgctgagtcc
 541  gcagcactca gactacgtgc acctctgcag caggtgcagg cccagttgtc acccctccag
 601  aacatctccc catggattct ggcggtattg actcttcaga ttcagagtct gatatcctgt
 661  tgggcattct ggacaacttg gacccagtca tgttcttcaa atgcccttcc ccagagcctg
 721  ccagcctgga ggagctccca gaggtctacc cagaaggacc cagttcctta ccagcctccc
 781  tttctctgtc agtggggacg tcatcagcca agctggaagc cattaatgaa ctaattcgtt
 841  ttgaccacat atataccaag cccctagtct tagagatacc ctctgagaca gagagccaag
 901  ctaatgtggt agtgaaaatc gaggaagcac ctctcagccc ctcagagaat gatcaccctg
 961  aattcattgt ctcagtgaag gaagaacctg tagaagatga cctcgttccg gagctgggta
1021  tctcaaatct gctttcatcc agccactgcc caaagccatc ttcctgccta ctggatgctt
1081  acagtgactg tggatacggg ggttcccttt ccccattcag tgacatgtcc tctctgcttg
1141  gtgtaaacca ttcttgggag gacactttg ccaatgaact ctttccccag ctgattagtg
1201  tctaaggaat gatccaatac tgttgccctt ttccttgact attacactgc ctggaggata
1261  gcagagaagc ctgtctgtac ttcattcaaa agccaaaat agagagtata cagtcctaga
1321  gaattcctct atttgttcag atctcataga tgaccccag gtattgtctt ttgacatcca
1381  gcagtccaag gtattgagac atattactgg aagtaagaaa tattactata attgagaact
1441  acagctttta agattgtact tttatcttaa aagggtggta gttttcccta aaatacttat
1501  tatgtaaggg tcattagaca aatgtcttga agtagacatg gaatttatga atggttcttt
1561  atcatttctc ttccccttt ttggcatcct ggcttgcctc cagtttagg tcctttagtt
1621  tgcttctgta agcaacggga acacctgctg aggggctct ttccctcatg tatacttcaa
1681  gtaagatcaa gaatcttttg tgaaattata gaaatttact atgtaaatgc ttgatggaat
1741  ttttcctgc tagtgtagct tctgaaaggt gctttctcca tttatttaaa actacccatg
1801  caattaaaag gtacaatgca
```

TABLE X

Restriction map of AAV-PGK1-HA-Xbp-1(human)-WPREggcggatccaattgcctaggcccaagggcgaattgtcacgactccacccc
tccaggaaccctagtgatggagttggccactccctctctgcgcgctcg
ctcgctcactgaggccgcccgggcaaagcccgggcgtcgggcgacctttg
gtcgcccggcctcagtgagcgagcgagcgcgcagagagggagtggccag
atctgatatcatcgatgaattcaagcttcagctgctcgagttctatagtg
tcacctaaatcgtatgtgtatgatcataaggttatgtattaattgtagc
gcgttctaacgacaatatgtccatatggtgcactctcagtacaatctgc
tctgatgccgcatagttaagccagcccgacacccgccaacacccgctga
cgcgccctgacgggcttgtctgctcccggcatccgcttacagacaagct
tgaccgtctccgggagctgcatgtgtcagaggttttcaccgtcatcaccg
aaacgcgcgagacgaaagggcctcgtgatacgcctatttttatggttaa
tgtcatgataataatggtttcttagacgtcaggtggcacttttcggggaa
atgtgcgcggaaccccctatttgttttattttctaaatacattcaaatatg
tatccgctcatgagacaataaccctgataaatgcttcaataatattgaaa
aaggaagagtatgagtattcaactttcgtgtcgcccttattccctttt
ttgcggcattttgccttcctgtttttgctcacccagaaacgctggtgaaa
gtaaaagatgctgaagatcagttgggtgcacgagtgggttacatcgaact
ggatctcaacagcggtaagatcttgagagttttcgccccgaagaacgtt
ttccaatgatgagcacttttaaagttctgctatgtggcgcggtattatcc
cgtattgacgccgggcaagagcaactcggtcgccgcatacactattctca
gaatgacttggttgagtactcaccagtcacagaaaagcatcttacggatg TABLE X-continued Restriction map of AAV-PGK1-HA-Xbp-1(human)-WPREgcatgacagtaagagaattatgcagtgctgccataaccatgagtgataac
actgcggccaacttacttctgacaacgatcggaggaccgaaggagctaac
cgcttttttgcacaacatgggggatcatgtaactcgccttgatcgttggg
aaccggagctgaatgaagccataccaaacgacgagcgtgacaccacgatg
cctgtagcaatggcaacaacgttgcgcaaactattaactggcgaactact
tactctagcttcccggcaacaattaatagactggatggaggcggataaag
ttgcaggaccacttctgcgctcggcccttccggctggctggtttattgct
gataaatctggagccggtgagcgtgggtctcgcggtatcattgcagcact
ggggccagatggtaagccctcccgtatcgtagttatctacacgacgggga
gtcaggcaactatggatgaacgaaatagacagatcgctgagataggtgcc
tcactgattaagcattggtaactgtcagaccaagtttactcatatatact
ttagattgatttaaaacttcatttttaatttaaaaggatctaggtgaaga
tcctttttgataatctcatgaccaaaatcccttaacgtgagttttcgttc
cactgagcgtcagaccccgtagaaaagatcaaaggatcttcttgagatcc
ttttttttctgcgcgtaatctgctgcttgcaaacaaaaaaaccaccgctac
cagcggtggtttgtttgccggatcaagagctaccaactctttttccgaag
gtaactggcttcagcagagcgcagataccaaatactgtccttctagtgta
gccgtagttaggccaccacttcaagaactctgtagcaccgcctacatacc
tcgctctgctaatcctgttaccagtggctgctgccagtggcgataagtcg
tgtcttaccgggttggactcagacgatagttaccggataaggcgcagcgg
tcgggctgaacggggggttcgtgcacacagcccagcttggagcgaacgac

TABLE X-continued

Restriction map of AAV-PGK1-HA-Xbp-1(human)-WPREctacaccgaactgagatacctacagcgtgagcattgagaaagcgccacgc
ttcccgaagggagaaaggcggacaggtatccggtaagcggcagggtcgg
aacaggagagcgcacgagggagcttccaggggggaaacgcctggtatcttt
atagtcctgtcgggtttcgccacctctgacttgagcgtcgatttttgtga
tgctcgtcagggggcggagcctatggaaaaacgccagcaacgcggcctt
tttacggttcctggccttttgctggcctttgccacatgttctttcctgc
gttatcccctgattctgtggataaccgtattaccgcctttgagtgagctg
atatccgctcgccgcagccgaacgaccgagcgcagcgagtcagtgagcgag
gaagcggaagagcgcccaatacgcaaaccgcctctccccgcgcgttggcc
gattcattaatgcaggttaacctggctttatcgaaattaatacgactcact
ataggggagaccggcagatctgtccctctctgcgcgctcgctcgctcactg
aggccgcccgggcaaagcccgggcgtcgggcgacctttggtcgcccggcc
tcagtgagcgagcgagcgcgcagagagggagtggccaactccatcactag
gggttccttgtagttaatgattaaccccgccatgctacttatctacaattc
gcccttcggacgcgtggcttcgaactaggcaattgcatgaagaatctgct
tagggttaggcgttttgcgctgcttcgcgatgtacgggccagatatacgc
gttgacattgattattgactagttattaatagtaatcaattacgggtca
ttagttcatagcccatatatggagttccgcgttacataacttacggtaaa
tggccggctggctgaccgcccaacgaccccccgcccattgacgtcaataa
tgacgtatgttcccatagtaacgccaatagggactttccattgacgtcaa
tgggtggagtatttacggtaaactgcccacttggcagtacatcaagtgta
tcatatgccaagtacgccccctattgacgtcaatgacggtaaatggcccg
cctgcattatgcccagtacatgacctatgggactttcctacttggcag
tacatctacgtattagtcatcgctattaccatggtgatgcggttttggca
gtacatcaatgggcgtggatagcggtttgactcacggggatttccaagtc
tccaccccattgacgtcaatgggagtttgttttggcaccaaaatcaacgg
gactttccaaaatgtcgtaacaactccgccccattgacgcaaatgggcgg
taggcgtgtacggtgggaggtctatataagcagagctctctggctaacta
gagaacccactgcttactggcttatcgaaattaatacgactcactatagg
gagacccaagctggctagcgtttaaacttaagcttcctggctatggtggt
ggtggcagccgcgccgaacccggccgacgggacccctaaagttctgcttc
tgtcggggcagcccgcctccgccgccggagcccggccggcaggccctg
ccgctcatggtgccagcccagagaggggccagcccggaggcagcgagcgg
ggggctgccccaggcgcgcaagcgacagcgcctcacgcacctgagccccg
aggagaaggcgctgaggaggaaactgaaaaacagagtagcagctcagact
gccagagatcgaaagaaggctcgaatgagtgagctggaacagcaagtggt
agatttagaagaagagaaccaaaaactttgctagaaatcagcttttac
gagagaaaactcatggccttgtagttgagaaccaggagttaagacagcgc
ttggggatggatgccctggttgctgaagaggaggcggaagccaagggaa
tgaagtgaggccagtggccgggtctgctgagtccgcagcaggtgcaggcc
cagttgtcaccctccagaacatctccccatggattctggcggtattgac
tcttcagattcagagtctgatatcctgttgggcattctggacaacttgga
cccagtcatgttcttcaaatgcccttccccagagcctgccagcctggagg
agctcccagaggtctacccagaaggacccagttccttaccagcctccctt
tctctgtcagtggggacgtcatcagccaagctggaagccattaatgaact
aattcgttttgaccacatatataccaagccccagtcttagatacccct
ctgagacagagagccaagctaatgtggtagtgaaaatcgaggaagccct
ctcagccctcagagaatgatcaccctgaattcattgtctcagtgaagga
agaacctgtagaagatgacctcgttccggagctgggtatctcaaatctgc
tttcatccagccactgcccaaagccatcttcctgcctactggatgcttac
agtgactgtggatacggggggttcccttttccccattcagtgacatgtcctc
tctgcttggtgtaaaccattcttgggaggacacttttgccaatgaactct
ttccccagctgattagtgtctacccatacgatgttccagattacgcaatg
taaagagccacataacactgggcccctttccctgaccatcacattgccta
gaggatagcataggcctgaagggcgaattccagcacactggcggccgtta
ctagagggcccgtttaaacccgctgatcacctcgactgtgccttctagtt
gccagccatctgttgtttgccctcccccgtgccttccttgaccctggaa
ggtgccactccactgtccttttcctaataaaatgaggaaattgcatcgca
ttgtctgagtaggtgtcattctattctggggggtggggtggggcaggaca

TABLE X-continued

Restriction map of AAV-PGK1-HA-Xbp-1(human)-WPREgcaaggggggaggattgggaagacaatagcaggcatgctgcagcggtccg
gtcgactctagaggatccgaaaaaacctcccacacctcccccctgaacctg
aaacataaaatgaatgcaattgttgttgttaacttgtttattgcagctta
taatggttacaaataaagcaatagcatcacaaatttcacaaataaagcat
ttttttcactgcattctagttgtggtttgtccaaactcatcaatgtatct
tatcatgtctggatccccgcggtggcggccgcactagtcccgggttaatt
aagctagcagatcttgatcacctaggcgtacgattggccgctttacatg
gtggcgaccggggatcctctagtaccaagctaattcctcacgacacctga
aatggaagaaaaaaactttgaaccactgtctgaggcttgagaatgaacca
agatccaaactcaaaagggcaaattccaaggagaattacatcaagtgcc
aagctggcctaacttcagtctccacccactcagtgtggggaaactccatc
gcataaaacccctccccccaacctaaagacgacgtactccaaaagctcga
gaactaatcgaggtgcctggacggcgcccggtactccgtggagtcacatg
aagcgacggctgaggacggaaaggccccttttcctttgtgtgggtgactca
cccgcccgctctcccgagcgccggtcctccattttgagctccctgcagc
agggccggggaagcggccatctttccgctcacgcaactggtgccgaccggg
ccagccttgccgcccagggcggggcgatacacggcggcgcgaggccaggc
accagagcaggccggccagcttgagactacccccgtccgattctcggtgg
ccgcgctccgaggccccgcctcgccgaacatgtgcgctgggacgcacggg
cccgtcgccgccgcggccccaaaaaccgaaataccagtgtgcagatct
tggcccgcatttacaagactatcttgccagaaaaaaagcgtcgcagcagg
tcatcaaaaatttaaatggctagagacttatcgaaagcagcgagacagg
cgcgaaggtgccaccagattcgcacgcggcggccccagcgccaggccag
gcctcaactcaagcacgaggcgaagggctccttaagcgcaaggcctcga
actctcccaccacttccaacccgaagctcgggatcaagaatcacgtact
gcagccaggtggaagtaattcaaggcacgcaagggccataacccgtaaag
aggccaggcccgcgggaaccacacacggcacttacctgtgttctggcggc
aaaccgttgcgaaaaagaacgttcacggcgactactgcacttatatacg
gttctccccaccctcgggaaaaaggcggagccagtacacgacatcactt
tcccagtttaccccgcgccaccttctctaggcaccgg Features:
XBP1s: [3257:5917-CW]

cdd XBP1s: [3593:4720-CW]

HA: [4721:4750-CW]

L-ITR: [89:196-CW]

R-ITR: [2629:2736-CW]

T7: [2587:2606-CW]

T7: [2532:3551-CW]

SP6: [259:242-CCW]

ColE1 origin: [1719:2347-CW]

Amp: [908:1567-CW]

SV40 late polyA: [5311:5120-CCW]

Amp prom: [640:668-CW]

HA tag: [4721:4747-CW]

The invention claimed is:

1. An adeno-associated vector (AAV) comprising an expression cassette that comprises a neuron-specific promoter operatively joined to a polynucleotide encoding X-box protein 1 (XBP1) in the brain of a mammal, wherein the expression cassette induces overexpression of XBP1 in the brain and thereby improves a cognitive process selected from learning and memory in the mammal as compared to the mammal without overexpression of XBP1.

2. The AAV according to claim 1, wherein the XBP1 is XBP1s or XBP1u.

3. A pharmaceutical composition, comprising an adeno-associated vector of claim 1 and a pharmaceutically acceptable excipient.

4. A pharmaceutical composition according to claim 3, wherein the composition comprises a dose of the virus in a range between $10^9$ to $10^{13}$ copies of genome (CG) per ml of composition.

5. A method to obtain the adeno-associated viral vector of claim 1, comprising the steps of:
  maintaining a cell comprising a polynucleotide comprising a neuron-specific promoter operatively joined to an X-box protein 1 (XBP1), and comprising an AAV Cap, an AAV Rep and viral replication factors on which AAV depends for its replication under adequate conditions for the assembly of the AAV; and
  purifying the adeno-associated viral vector produced by the cell.

6. A method according to claim 5, wherein the viral replication factors on which AAV depends for replication are derived from an adenovirus.

7. A method according to claim 5, wherein the proteins Cap and Rep of the adeno-associated virus are derived from an AAV selected from the serotypes AAV2, AAV6, AAV7, AAV8 and AAV9.

8. A method according to claim 7, wherein the proteins Cap and Rep of the adeno-associated virus are derived from the serotype AAV6.

9. The AAV according to claim 1, wherein the AAV comprises a Cap derived from AAV2, AAV6, AAV7, AAV8, AAV9.

10. The AAV according to claim 1, wherein the AAV comprises a coding region for an immune response selected from Ha, Flag, Gfp, His, and Myc.

11. The AAV according to claim 1, wherein the expression cassette comprises a regulatory post-transcriptional region.

12. The AAV according to claim 1, wherein the cognitive process is a hippocampus-dependent process.

13. The AAV according to claim 1, wherein the cognitive process in the mammal is improved after inducing overexpression of XBP1, as compared to the cognitive process in the same mammal prior to inducing overexpression of XBP1.

14. The AAV according to claim 1, wherein the overexpression of XBP1 is an increase in XBP1 expression relative to XBP1 expression in the absence of the AAV.

* * * * *